(12) United States Patent
Spiekerkoetter et al.

(10) Patent No.: US 11,413,280 B2
(45) Date of Patent: Aug. 16, 2022

(54) ENZASTAURIN AND FRAGILE HISTIDINE TRIAD (FHIT)-INCREASING AGENTS FOR THE TREATMENT OF PULMONARY HYPERTENSION

(71) Applicant: The Board of Trustees of the Leland Stanford Junior University, Palo Alto, CA (US)

(72) Inventors: Edda Spiekerkoetter, Redwood City, CA (US); Svenja Dannewitz Prosseda, Graevenwiesbach (DE); Xuefei Tian, Fremont, CA (US); Purvesh Khatri, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 16/614,778

(22) PCT Filed: May 18, 2018

(86) PCT No.: PCT/US2018/033533
§ 371 (c)(1),
(2) Date: Nov. 18, 2019

(87) PCT Pub. No.: WO2018/213800
PCT Pub. Date: Nov. 22, 2018

(65) Prior Publication Data
US 2020/0206214 A1    Jul. 2, 2020

Related U.S. Application Data

(60) Provisional application No. 62/508,881, filed on May 19, 2017.

(51) Int. Cl.
| | | |
|---|---|---|
| A61K 31/4545 | (2006.01) | |
| A61P 9/12 | (2006.01) | |
| A61P 11/00 | (2006.01) | |
| A61K 45/06 | (2006.01) | |

(52) U.S. Cl.
CPC .......... *A61K 31/4545* (2013.01); *A61K 45/06* (2013.01); *A61P 9/12* (2018.01); *A61P 11/00* (2018.01)

(58) Field of Classification Search
CPC ......... A61K 31/4545; A61P 9/12; A61P 11/00
See application file for complete search history.

(56) References Cited

U.S. PATENT DOCUMENTS

| | | | |
|---|---|---|---|
| 8,741,861 B2* | 6/2014 | Mann | A61K 38/4886 514/44 A |
| 9,499,816 B2* | 11/2016 | Mann | A61K 31/7048 |
| 2002/0137086 A1 | 9/2002 | Olek | |
| 2005/0119330 A1 | 6/2005 | Kao et al. | |
| 2007/0265294 A1 | 11/2007 | Kleinman | |
| 2011/0091421 A1 | 4/2011 | Mann | |
| 2011/0311995 A1 | 12/2011 | Mouthon et al. | |
| 2014/0135358 A1 | 5/2014 | Spiekerkoetter et al. | |
| 2015/0323550 A1 | 11/2015 | Mouthon et al. | |
| 2016/0296588 A1 | 10/2016 | Hill | |
| 2017/0007585 A1 | 1/2017 | Spiekerkoetter et al. | |
| 2018/0185340 A1 | 7/2018 | Spiekerkoetter et al. | |
| 2019/0091208 A1 | 3/2019 | Spiekerkoetter et al. | |

FOREIGN PATENT DOCUMENTS

WO    2015/116735 A1    8/2015

OTHER PUBLICATIONS

Extended European Search Report, EP Application No. 18801557.2, dated Dec. 18, 2020, 9 pgs.
PCT/US2018/033533 International Search Report and Written Opinion of the International Searching Authority, dated Aug. 9, 2018 4 pages.
Andruska, A., et al., Targeting BMPR2 Trafficking with Chaperones: An Important Step toward Precision Medicine in Pulmonary Arterial Hypertension, Amer Jour. Respiratory Cell and Molec Bio, Aug. 2020, 63(2):137-138.
Andruska, A. et al., Consequences of BMPR2 Deficiency in the Pulmonary Vasculature and Beyond: Contributions to Pulmonary Arterial Hypertension, Int'l J. Mol. Sci, 2018, 19, 2499, 24 pages.
Dannewitz Prosseda, S., et al., FHIT, a Novel Nodifier Gene in Pulmonary Arterial Hypertension, American Jour Respiratory and Critical Care Med., Jan. 1, 2019, 199 (1): 83-98.
Grinnan, D., et al., Drug repositioning in pulmonary arterial hypertension: challenges and opportunities, Pulmonary Circulation, 2019; 9(1): 1-18.
Koerner, A., et al., Enzastaurin inhibits invasion and metastasis in lung cancer by diverse molecules, British Jour. Cancer, 2010, 103(6): 802-811.
Prosseda et al., A4228: Enzastaurin Reverses Pulmonary Arterial Hypertension By Targeting The Novel Mnpr2 Modifier Fhit, Am J Respir Crit Care Med, May 22, 2017, p. 1, vol. 195.
Spiekerkoetter, E., et al, FK506 activates BMPR2, rescues endothelial dysfunction, and reverses pulmonary hypertension. Jour. Clinical Investigation, Aug. 2013, 123(8):3600-3613.
Spiekerkoetter, E., et al., New and Emerging Therapies for Pulmonary Arterial Hypertension, Annu Rev Med. Jan. 27, 2019; 70:45-59.

(Continued)

*Primary Examiner* — Kevin E Weddington
(74) *Attorney, Agent, or Firm* — Eleanor Musick; Torrey Pines Law Group, PC

(57) ABSTRACT

The present invention provides methods for treatment or prevention of pulmonary hypertension and emphysema using agents that increase activity of FHIT, such as Enzastaurin. Included are methods for using levels of FHIT and/or BMPR2, and checking for mutations in FHIT and/or BMPR2, to select patients for treatment or to monitor effectiveness of treatment. The invention is based on evidence that Enzastaurin prevents and reverses pulmonary hypertension induced in animal model systems, and that it acts by up-regulation of FHIT and/or BMPR2.

13 Claims, 56 Drawing Sheets

(56) References Cited

OTHER PUBLICATIONS

Sudheendra et al., A3875: Targeting a Novel BMPR2 Modified Gene, FHIT, with a Repurposed Drug to Improve Pulmonary Hypertension, American Journal of Respiratory and Critical Care Medicine, May 16, 2016 p. 1, vol. 193.
Sung, et al. Novel Approaches to Pulmonary Arterial Hypertension Drug Discovery, Expert Opin Drug Discovery, Feb. 27, 2016, pp. 407-414, vol. 11.

* cited by examiner

Female

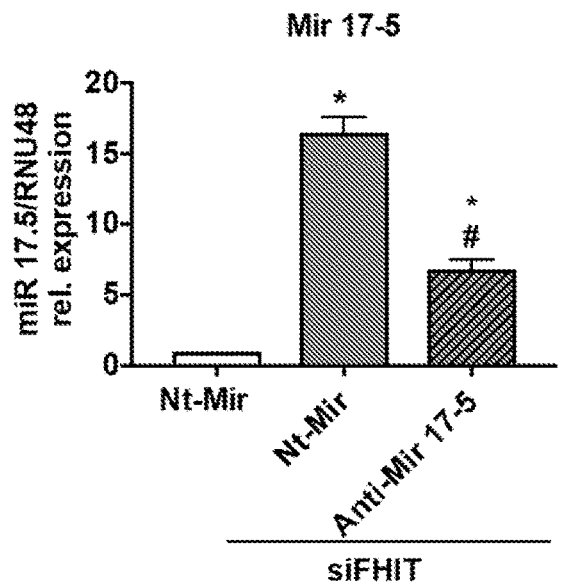 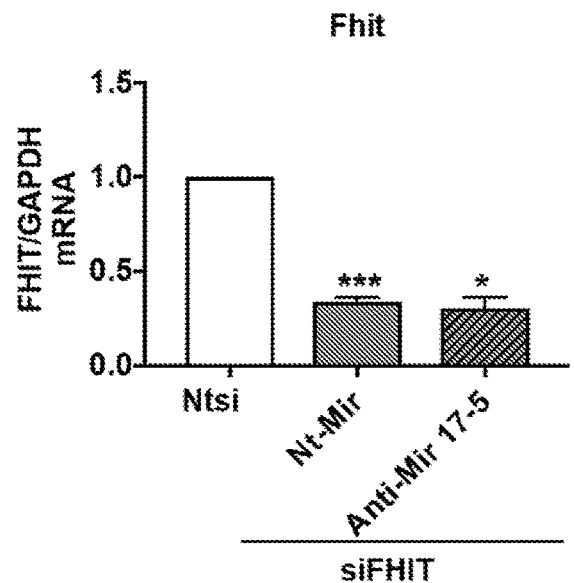
FIG. 21A  FIG. 21B
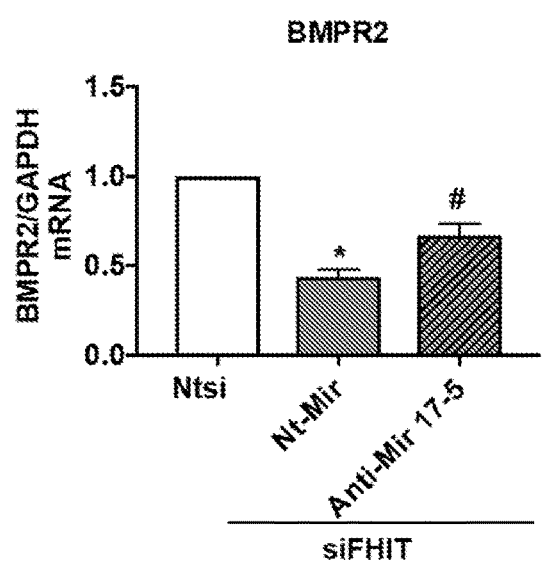 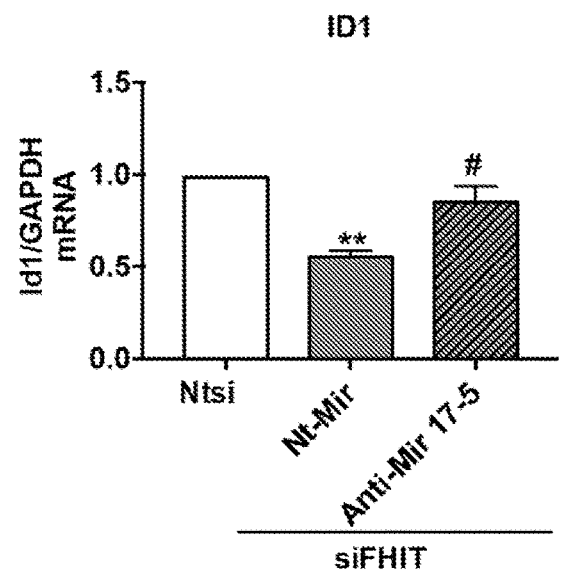
FIG. 21C  FIG. 21D

ENZASTAURIN AND FRAGILE HISTIDINE TRIAD (FHIT)-INCREASING AGENTS FOR THE TREATMENT OF PULMONARY HYPERTENSION

CROSS REFERENCE TO RELATED APPLICATIONS

This application is a U.S. national phase filing of International Patent Application Serial No. PCT/US2018/033533, entitled "ENZASTAURIN AND FRAGILE HISTIDINE TRIAD (FHIT)-INCREASING AGENTS FOR THE TREATMENT OF PULMONARY HYPERTENSION," which claims benefit of priority to U.S. Provisional Patent Application Serial No. 62/508,881, filed May 19, 2017, the contents of the above applications are incorporated herein by reference in their entireties for all purposes.

GOVERNMENT RIGHTS

This invention was made with Government support under contracts K08HL107450-01 and R01 HL128734-01A1 awarded by the National Heart Lung and Blood Institute, and contracts 1U19AI109662, U19AI057229, and U54I117925 awarded by the National Institute of Allergy and Infectious Diseases. The Government has certain rights in the invention.

TECHNICAL FIELD

The present invention relates to the field of pharmacogenomics, which applies one or more genomic biomarkers and the related diagnostic methods, devices, reagents, systems, and kits, for predicting varied individual responses such as, for example, efficacy or adverse effect, to the selection and use of therapeutic agents for treating certain conditions including pulmonary hypertension. It relates to the use of enzastaurin and other agents that elevate or induce the Fragile Histidine Triad (FHIT) for treating conditions in which FHIT is deficient. In particular, it relates to biomarkers useful in connection with treatment of pulmonary hypertension, emphysema, and other conditions associated with reduced or insufficient FHIT, using enzastaurin and other FHIT-elevating agents. These FHIT-elevating agents are useful in treating diseases that present with elevated right ventricle systolic pressure (RVSP), right ventricle hypertrophy, cardiac fibrosis, pulmonary vasculature remodeling (i.e., blood vessel loss and vessel muscularization) or emphysema, found in diseases covered by the WHO classifications for Pulmonary Hypertension, such as (but not limited to) Pulmonary Hypertension (PH), Pulmonary Arterial Hypertension (PAH), Chronic Obstructive Pulmonary Disease (COPD) and emphysema.

BACKGROUND

Pulmonary Arterial Hypertension (PAH) is a devastating disease, characterized by progressive, occlusive pulmonary vasculopathy, ultimately leading to right-side heart failure and a considerably shortened life-span. Mutations in the Bone Morphogenetic Receptor 2 (BMPR2) gene are present in ~75% of familial PAH (FPAH) patients (1), clearly linking BMPR2 to the pathogenesis of the disease. Although BMPR2 mutations and reduced BMPR2 expression were reported in many idiopathic PAH (IPAH) and FPAH patients (2-4), surprisingly only a relatively small proportion (~20%) of BMPR2 mutation carriers develop a clinical PAH phenotype, suggesting additional environmental or genetic factors or 'second hits' involved in disease development, by either reducing BMPR2 signaling below a critical threshold or targeting BMPR2-independent pathways relevant for PAH pathogenesis.

Current PAH treatments are inadequate, as most approved PAH drugs primarily function as vasodilators or potential RV stabilizers(5), leaving the pulmonary vasculopathy to progress unchecked. There is a need for new therapeutic methods for treating pulmonary hypertension, including PAH, and emphysema. The present invention provides improved methods that are believed, without being bound by theory, to operate by increasing the level of FHIT. Therapeutic targeting of BMPR2 signaling is considered an attractive strategy to improve PAH (6-9), independent of the BMPR2 mutational status, as it has been shown effective with the repurposed drug FK506 that increases BMPR2 signaling(10-12). Our goal was therefore to identify and pharmaceutically target BMPR2 modifier genes to increase BMPR2 signaling or expression in FPAH and IPAH patients and others with reduced FHIT expression or activity.

The data provided herein combines a systematic High Throughput siRNA Screen (HTS) of genes that regulate BMPR2 signaling with a novel multi-cohort and multi-tissue analysis approach of publicly available PAH RNA expression. The siRNA screen identified BMPR2 activating genes that—when knocked down—reduced BMPR2 signaling as assessed by ID1 expression. Cross-validating these genes with genes consistently downregulated in the publicly available PAH gene expression dataset, showed that BMPR2 modifier genes are clinically relevant in PAH. The results indicate that upregulation of these genes would improve clinical outcomes for subjects with pulmonary hypertension and similar disorders, and show that Fragile Histidine Triad (FHIT) is a potential modifier gene in PAH, and that reduced FHIT expression was associated with reduced BMPR2 signaling and endothelial cell (EC) dysfunction in vitro and in vivo.

FHIT is a member of the histidine triad family, located on chromosome 3, overlapping the FRA3B locus(13), the human common fragile site most susceptible to replication stress and associated deletions. The tumor suppressor gene FHIT is readily lost after exposure to carcinogens or stressors, such as cigarette smoke and UV irradiation(14, 15). FHIT is highly expressed in the lung(16), and is commonly lost in lung cancer and other malignancies(17, 18). Moreover, FHIT is implicated in apoptosis and proliferation in various cell types(19, 20), potentially linking it to the abnormal proliferative phenotype observed in PAH endothelial and smooth muscle cells (PASMC). FHIT and BMPR2 expression were up-regulated by Enzastaurin, a safe and well tolerated drug tested in a phase III clinical trial to prevent lymphoma relapse(21). It has surprisingly been shown herein that increasing FHIT by Enzastaurin prevented and reversed experimental PH progression. This demonstrates that FHIT is mechanistically important in PH pathogenesis, and that Enzastaurin or other FHIT-enhancing agents would be useful for clinical treatment of PAH and similar FHIT-deficient conditions. abstract (22).

The following summary is not intended to be used to limit the scope of the claimed subject matter. Other features, details, utilities, and advantages of the claimed subject matter will be apparent from the detailed description including those aspects disclosed in the accompanying drawings and in the appended claims.

SUMMARY OF ASPECTS OF THE INVENTION

One embodiment of the present invention comprises the use of FHIT as a biomarker for the prediction of PH disease status. Another embodiment of the present invention comprises the use of FHIT-elevating agent Enzastaurin, or other FHIT-elevating agents due to their function as FHIT-elevating agents, independent of PKC inhibition, as a preventative or ameliorating therapeutic strategy in mammals with risk factors for the development of pulmonary hypertension or symptoms thereof. Another embodiment of the present invention comprises a method of reducing pulmonary hypertension in a mammal exhibiting symptoms of pulmonary hypertension that employs FHIT-elevating agent Enzastaurin or other FHIT-elevating agents to elevate FHIT levels. In certain embodiments, the method comprises administering FHIT-elevating agent Enzastaurin or other FHIT-elevating agents to a mammal having pulmonary arterial hypertension at a dosage sufficient to reduce blood pressure and elevate FHIT levels. In some cases, the mammal may be a mouse, a rat or a human. In particular cases, the mammal has hereditary pulmonary arterial hypertension (e.g., FPAH) caused by a one allele knockout of the BMPR2 gene. In particular cases, pulmonary hypertension was caused by a homozygous knockout of the FHIT gene on both alleles. In particular cases, the pulmonary hypertension was caused by the induction of FHIT, for example by inducing experimental pulmonary hypertension after administering Sugen5416 and exposure to chronic hypoxia. In particular cases, the FHIT-elevating agent Enzastaurin or other FHIT-elevating agents may be administered orally at a dose sufficient to achieve a reduction in right ventricle size and right ventricle systolic pressure.

In one aspect, the invention provides a method for preventing and/or treating pulmonary hypertension and/or emphysema in a subject in need of prevention and/or treatment, which method comprises administering an effective amount of:
  1) an agent that provides for or enhances level and/or an activity of Fragile Histidine Triad (FHIT); and/or
  2) Enzastaurin, to said subject.
This aspect includes the use of Enzastaurin in therapy, and particularly the use of Enzastaurin for treating pulmonary hypertension or emphysema. It also includes the use of Enzastaurin for the manufacture of a medicament, particularly a medicament for treating pulmonary hypertension or emphysema.

In another aspect, the invention provides a combination with therapeutic utility that comprises:
  1) an agent that provides for or enhances level and/or an activity of Fragile Histidine Triad (FHIT) in a subject and/or Enzastaurin; and
  2) a second prophylactic or therapeutic agent for preventing and/or treating pulmonary hypertension and/or emphysema.

In another aspect, the invention provides a pharmaceutical composition, which comprises an effective amount of enzastaurin, or a combination comprising enzastaurin such as those described above, and a pharmaceutically acceptable carrier or excipient. This aspect includes use of an agent that increases activity of FHIT, such as enzastaurin, for the manufacture of a medicament, that preferably includes a pharmaceutically acceptable carrier or excipient. It further provides the use in therapy of a combination comprising an agent that increases activity of FHIT, such as enzastaurin, and at least one pharmaceutically acceptable carrier or excipient, where the use in therapy is use to treat pulmonary hypertension or emphysema, including forms of these conditions described herein, such as FPAH, PAH, and/or iPAH.

In another aspect, the invention provides a method for preventing and/or treating pulmonary hypertension and/or emphysema in a subject in need of such prevention and/or treatment, which method comprises administering an effective amount of enzastaurin, or a combination comprising enzastaurin such as those described above, a pharmaceutical composition comprising an effective amount of enzastaurin, including a combination comprising enzastaurin such as those described above, to said subject.

In yet another aspect, the invention provides a method for assessing pulmonary hypertension and/or emphysema in a subject, which method comprises:
  a) providing a sample from a subject;
  b) assessing FHIT and/or BMPR2 level and/or activity in said sample to assess pulmonary hypertension and/or emphysema in said subject.

In yet another aspect, the invention provides a method for selecting a subject having pulmonary hypertension for treatment with enzastaurin or a composition comprising enzastaurin, which method comprises:
  a) providing a sample from a subject;
  b) assessing FHIT and/or BMPR2 level and/or activity in said sample to assess suitability of enzastaurin for treating pulmonary hypertension and/or emphysema in said subject. A subject is deemed suitable for treatment with Enzastaurin or other FHIT-elevating agents if the level of FHIT and/or BMPR2 is low (e.g., at least 50% below, or at least 80% below a normal level) or is undetectable.

In yet another aspect, the invention provides a method of reducing pulmonary hypertension or emphysema in a mammal, comprising: administering an effective amount of Fragile Histidine Triad (FHIT)-elevating agent Enzastaurin or other FHIT-elevating agents to the mammal having pulmonary hypertension or emphysema, wherein the administered dosage is below 1000 mg/day and is sufficient to reduce blood pressure of said mammal.

In yet another aspect, the invention provides a method of reducing pulmonary hypertension or emphysema in a mammal with low or undetectable levels of FHIT, comprising:
  obtaining a blood sample from the mammal;
  determining the level of FHIT in the blood sample; and
  administering an effective amount of FHIT-elevating agent Enzastaurin or other FHIT-elevating agents to the mammal having pulmonary hypertension or emphysema, if the sample has a low or undetectable level of FHIT.

In yet another aspect, the invention provides a method of reducing pulmonary hypertension or emphysema in a mammal with low or undetectable levels of FHIT, comprising:
  a. obtaining a tissue sample from the mammal;
  b. determining the level of FHIT in the tissue sample; and
  c. administering an effective amount of FHIT-elevating agent Enzastaurin or other FHIT-elevating agents to the mammal having pulmonary hypertension or emphysema, if the sample has a low or undetectable level of FHIT.

In yet another aspect, the invention provides a method of reducing pulmonary hypertension or emphysema in a mammal with low or undetectable levels of BMPR2, comprising:
  a. obtaining a blood sample from the mammal;
  b. determining the level of BMPR2 in the blood sample; and
  c. administering an effective amount of FHIT-elevating agent Enzastaurin or other FHIT-elevating agents to the mammal having pulmonary hypertension or emphysema, if the sample has a low or undetectable level of BMPR2.

In yet another aspect, the invention provides a method of reducing pulmonary hypertension or emphysema in a mammal with low or undetectable levels of BMPR2, comprising:
 a. obtaining a tissue sample from the mammal;
 b. determining the level of BMPR2 in the tissue sample; and
 c. administering an effective amount of FHIT-elevating agent Enzastaurin or other FHIT-elevating agents to the mammal having pulmonary hypertension or emphysema, if the sample has a low or undetectable level of BMPR2.

In yet another aspect, the invention provides a method of reducing pulmonary hypertension or emphysema in a mammal with a mutation of BMPR2, comprising:
 a. obtaining a tissue sample from the mammal;
 b. analyzing the tissue sample for a BMPR2 mutation; and
 c. administering an effective amount of FHIT-elevating agent Enzastaurin or other FHIT-elevating agents to the mammal having pulmonary hypertension or emphysema, if a BMPR2 mutation was detected.

In yet another aspect, the invention provides a method of reducing pulmonary hypertension or emphysema in a mammal with a mutation of BMPR2, comprising:
 a. obtaining a blood sample from the mammal;
 b. analyzing the blood sample for a BMPR2 mutation; and
 c. administering an effective amount of FHIT-elevating agent Enzastaurin or other FHIT-elevating agents to the mammal having pulmonary hypertension or emphysema, if a BMPR2 mutation was detected.

In yet another aspect, the invention provides a method of reducing pulmonary hypertension or emphysema in a mammal with a mutation of FHIT, comprising:
 a. obtaining a tissue sample from the mammal;
 b. analyzing the tissue sample for a FHIT mutation; and
 c. administering an effective amount of FHIT-elevating agent Enzastaurin or other FHIT-elevating agents to the mammal having pulmonary hypertension or emphysema, if a FHIT mutation was detected.

In yet another aspect, the invention provides a method of reducing pulmonary hypertension or emphysema in a mammal with a FHIT mutation, comprising:
 a. obtaining a blood sample from the mammal;
 b. analyzing the blood sample for a FHIT mutation; and
 c. administering an effective amount of FHIT-elevating agent Enzastaurin or other FHIT-elevating agents to the mammal having pulmonary hypertension or emphysema, if a FHIT mutation was detected.

In any of the preceding embodiments, the treatment can comprise administering to a subject in need thereof a pharmaceutically effective amount of a bisindolylmaleimide or an analogue or derivative thereof having activity that elevates FHIT levels or activity. In one embodiment, the bisindolylmaleimide or analogue or derivative is Enzastaurin or an analogue or derivative thereof: in particular, the bisindolylmaleimide is Enzastaurin, which can be administered as a neutral compound or a pharmaceutically acceptable salt of Enzastaurin Further aspects and specific embodiments of the invention are described and enabled herein.

BRIEF DESCRIPTION OF THE DRAWINGS

FIGS. 14A-14C 24 h treatment with Enzastaurin increases FHIT, BMPR2 and Id1 expression in PAECs in which FHIT is reduced by siRNA.

FIGS. 21A-21D: Reduction of BMPR2 and ID1 in PAEC by FHIT knockdown is in part miR17-5 dependent.

DETAILED DESCRIPTION OF ASPECTS OF THE INVENTION

Figure 1A:
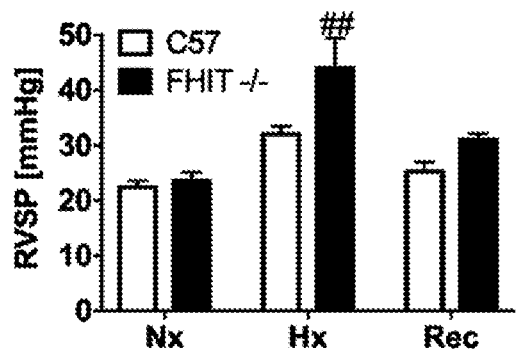
FIGS. 1A-1K: Male FHIT−/− C57BL/6 mice develop experimental PAH after chronic exposure to Hypoxia.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can be applied alone or in some combination to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications referred to in this application are incorporated by reference in their entireties for all purposes to the same extent as if each individual publication were individually incorporated by reference.

All headings are for the convenience of the reader and should not be used to limit the meaning of the text that follows the heading, unless so specified.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

The method described herein is for treating pulmonary hypertension in patients with any of the following: elevated right ventricle systolic pressure, right ventricle hypertrophy, pulmonary vessel neo-muscularization of previously unmuscularized vessels and the increase in their circumference, pulmonary vessel loss, elevated pulmonary vessel neointima formation, elevated pulmonary vessel media hypertrophy.

The present invention relates to methods of using FHIT as a biological marker in conjunction with the treatment of pulmonary arterial hypertension using FHIT-elevating agent Enzastaurin or other FHIT-elevating agents. The present invention relates to the treatment of pulmonary arterial hypertension using FHIT-elevating agent Enzastaurin or other FHIT-elevating agents in familial and idiopathic Pulmonary arterial hypertension. The present invention also relates to the use of FHIT-elevating agent Enzastaurin or other FHIT-elevating agents alone or in conjunction with previously prescribed medications in order to ameliorate the vascular occlusive phenotype, pulmonary vessel loss, elevated right ventricle systolic pressure, emphysema, cardiac fibrosis and right ventricle hypertrophy present in pulmonary arterial hypertension.

Fragile Histidine Triad (FHIT) is a member of the histidine triad family, and is implicated in apoptosis and proliferation in various cell types (Accornero et al., 1999; Toledo et al., 2004), potentially linking it to the abnormal proliferative phenotype observed in PAH endothelial and smooth muscle cells. FHIT is thought to be degraded following its dephosphorylation by Src kinase (Pekarsky et al., 2004, Proc Natl Acad Sci USA, 101(11): 3775-3779).

FHIT-elevating agent Enzastaurin has the chemical name 3-(1-methyl-1H-indol-3-yl)-4-[1-[1-(pyridin-2-ylmethyl)piperidin-4-yl]-1H-indol-3-yl]-1H-pyrrole-2,5-dione and is disclosed in U.S. Pat. No. 5,668,152, where it is described as an inhibitor of Protein Kinase C (PKC). The biological function of Enzastaurin thus reportedly arises from its inhibition of protein phosphorylation by PKC. Its main target is in the inhibition of PKC beta activation; however, it furthermore inhibits further proteins involved in cell proliferation and cell survival pathways (Gescher, 1998, Gen Pharmacol., 31: 721-728; Jarvis, Grant, 1999. Invest New Drugs, 17:227-240; Parker, 1999, Pharmacol. Ther., 82:263-267). FHIT-elevating agent Enzastaurin or other FHIT-elevating agents suppresses cell growth, proliferation and induces apoptosis in various cell types.

In a Phase II trial, Enzastaurin showed tolerability for 6 months in the duration of the study (Gray et al., Cancer 2013 119(5): 1023-1032). Reported side-effects included rash, abdominal distension, hyponatremia, DVT and hypotension. Due to the high tolerability, minimal toxicity and low amount and severity of side-effects achieved with this drug, it's use as a treatment for pulmonary hypertension and the prevention of the development of familial pulmonary hypertension in at-risk individuals, such as a positive mutation status of BMPR2, is suggested here. The pulmonary hypertension disease reversal achieved with Enzastaurin is unprecedented and it, or other FHIT-elevating agents, is thus believed useful as a treatment strategy for pulmonary hypertension.

The FHIT-elevating agent Enzastaurin or other FHIT-elevating agents may be administered alone or in combination with other active compounds that treat or prevent PH, including PAH. The other active compound may be administered at a different time or at the same time as the FHIT-elevating agent Enzastaurin or other FHIT-elevating agents, and in certain embodiments the FHIT-elevating agent Enzastaurin or other FHIT-elevating agents and the other active compound may be present in the same formulation, or as separate formulations in the same kit. Exemplary other active compounds that treat PH include, e.g., prostacyclin analogues, endothelin receptor antagonists, phosphodiesterase-5 inhibitors, high-dose calcium channel blockers, anticoagulants, diuretics or antiproliferative agents. In particular cases, the other active compound may be, for example, Isordil (isosorbide dinitrate), Revatio (sildenafil), Tracleer (bosentan), Letairis (amrbrisentan), Flolan (epoprostenol), Adcirca (tadalafil), Remodulin (treprostinil) Ventavis (iloprost), Tyvaso (treprostinil), Dilatrate-SR (isosorbide dinitrate), Isordil Titradose (isosorbide dinitrate), IsoDitrate (isosorbide dinitrate) or Isochron (isosorbide dinitrate).

A. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

B. Definitions

Unless defined otherwise, all technical and scientific terms used herein have the same meaning as is commonly understood by one of ordinary skill in the art to which this invention belongs. All patients, applications, published applications and other publications referred to herein are incorporated by reference in their entireties. If a definition set forth in this section is contrary to or otherwise inconsistent with a definition set forth in the patients, applications, published applications and other publications that are herein incorporated by reference, the definition set forth in this section prevails over the definition that is incorporated herein by reference.

As used herein, the singular forms "a", "an", and "the" include plural references unless indicated otherwise. For example, "a" dimer includes one or more dimers.

The term "biomarker" or "marker" as used herein refers generally to a molecule, including a gene, protein, carbohydrate structure, or glycolipid, the expression of which in or on a mammalian tissue or cell or secreted can be detected by known methods (or methods disclosed herein) and is predictive or can be used to predict (or aid prediction) for a mammalian cell's or tissue's sensitivity to, and in some embodiments, to predict (or aid prediction) an individual's responsiveness to treatment regimens.

As used herein, a "pharmacogenomic biomarker" is an objective biomarker which correlates with a specific clinical drug response or susceptibility in a subject (see, e.g., McLeod et al., *Eur. J. Cancer* (1999) 35:1650-1652). It may be a biochemical biomarker, or a clinical sign or symptom. The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of DNA, RNA, or protein for specific tumor markers in a subject, a drug or course of treatment may be selected that is optimized for the treatment of the specific tumor likely to be present in the subject. Similarly, the presence or absence of a specific sequence mutation or polymorphism may correlate with drug response. The use of pharmacogenomic biomarkers therefore permits the application of the most appropriate treatment for each subject without having to administer the therapy.

As used herein, the term "polymorphic locus" refers to a region in a nucleic acid at which two or more alternative nucleotide sequences are observed in a significant number of nucleic acid samples from a population of individuals. A polymorphic locus may be a nucleotide sequence of two or more nucleotides, an inserted nucleotide or nucleotide sequence, a deleted nucleotide or nucleotide sequence, or a microsatellite, for example. A polymorphic locus that is two or more nucleotides in length may be 3, 4, 5, 6, 7, 8, 9, 10, 11, 12, 13, 14, 15 or more, 20 or more, 30 or more, 50 or more, 75 or more, 100 or more, 500 or more, or about 1000 nucleotides in length, where all or some of the nucleotide sequences differ within the region. A polymorphic locus is often one nucleotide in length, which is referred to herein as a "single nucleotide polymorphism" or a "SNP." In some embodiments, the high-density genotyping may be conducted by using SNPs. In some embodiments, about 1,000-5,000,000 or more SNPs, may be used. In some embodiments, the high-density genotyping may be array-based. In some embodiments, the high-density genotyping may be conducted by using sequencing, such as high-throughput sequencing.

Where there are two, three, or four alternative nucleotide sequences at a polymorphic locus, each nucleotide sequence is referred to as a "polymorphic variant" or "nucleic acid variant." Where two polymorphic variants exist, for example, the polymorphic variant represented in a minority of samples from a population is sometimes referred to as a "minor allele" and the polymorphic variant that is more prevalently represented is sometimes referred to as a "major allele." Many organisms possess a copy of each chromosome (e.g., humans), and those individuals who possess two major alleles or two minor alleles are often referred to as being "homozygous" with respect to the polymorphism, and those individuals who possess one major allele and one minor allele are normally referred to as being "heterozygous" with respect to the polymorphism. Individuals who are homozygous with respect to one allele are sometimes predisposed to a different phenotype as compared to individuals who are heterozygous or homozygous with respect to another allele.

Single-nucleotide polymorphisms may fall within coding sequences of genes, non-coding regions of genes, or in the intergenic regions (regions between genes). SNPs within a coding sequence do not necessarily change the amino acid sequence of the protein that is produced, due to degeneracy of the genetic code.

SNPs in the coding region are of two types, synonymous and nonsynonymous SNPs. Synonymous SNPs do not affect the protein sequence while nonsynonymous SNPs change the amino acid sequence of protein. The nonsynonymous SNPs are of two types: missense and nonsense.

SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene.

In genetic analysis that identifies one or more pharmacogenomic biomarkers, samples from individuals having different values in a relevant phenotype often are allelotyped and/or genotyped. The term "allelotype" as used herein refers to a process for determining the allele frequency for a polymorphic variant in pooled DNA samples from cases and controls, and/or in separate DNA samples from each individual subject. By genotyping DNA from each group, an allele frequency for each locus in each group is calculated. These allele frequencies are then compared to one another. In some embodiments, DNA samples are genotyped using whole genome SNP arrays, such as those manufactured by Affymetrix (Santa Clara, Calif.) and/or Illumina (San Diego, Calif.), such as the Affymetrix 500K array. In addition to Affymetrix arrays, Illumina chips and Sequenom MassArray can also be used. Any suitable genotype calling algorithm(s) may be used. In some embodiments, the genotype calls are generated using the Robust Linear Model with the Mahalanobis Distance Classifier (RLMM) algorithm, the RLMM with a Bayesian step (BRLMM) algorithm, the Axiom™ GT1 algorithm, the BRLMM using perfect-match probes (BRLMM-P) algorithm, or the Birdseed algorithm (Rabbee et al., *Bioinformatics* (2006) 22:7-12; Korn et al., *Nat Genet* (2008) 40:1253-60).

A genotype or polymorphic variant may be expressed in terms of a "haplotype," which as used herein refers to a set of DNA variations, or polymorphisms, that tend to be inherited together. A haplotype can refer to a combination of alleles or to a set of SNPs found on the same chromosome. For example, two SNPs may exist within a gene where each SNP position includes a cytosine variation and an adenine variation. Certain individuals in a population may carry one allele (heterozygous) or two alleles (homozygous) having the gene with a cytosine at each SNP position. As the two cytosines corresponding to each SNP in the gene travel together on one or both alleles in these individuals, the individuals can be characterized as having a cytosine/cytosine haplotype with respect to the two SNPs in the gene.

Sometimes, a polymorphic variant is reported in a database without determining whether the variant is represented in a significant fraction of a population. Because a subset of these reported polymorphic variants are not represented in a statistically significant portion of the population, some of them are sequencing errors and/or not biologically relevant. Thus, it is often not known whether a reported polymorphic variant is statistically significant or biologically relevant until the presence of the variant is detected in a population of individuals and the frequency of the variant is determined. A polymorphic variant is statistically significant (and optionally often biologically relevant) if it is represented in 1% or more of a population, sometimes 5% or more, 10% or more, 15% or more, or 20% or more of a population, and often 25% or more, 30% or more, 35% or more, 40% or more, 45% or more, or 50% or more of a population. For certain genetic diseases and/or rare diseases, however, a variant may represent a very small percentage of a population and yet is still biologically relevant.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "clinical sample" or "disease sample" and variations thereof refer to any sample obtained from a subject of interest that would be expected or is known to contain the cellular and/or molecular entity that is to be characterized.

The term "tissue or cell sample" refers to a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds that are not naturally intermixed with the tissue in nature such as preservatives, anticoagulants, buffers, fixatives, nutrients, antibiotics, or the like.

The biological sample herein can be a plasma, serum, whole blood, or dried blood spot sample. "Plasma," or "blood plasma," as used herein, refers to the intravascular fluid part of extracellular fluid (all body fluid outside of cells). It is mostly water and contains dissolved proteins, glucose, clotting factors, mineral ions, hormones and carbon dioxide (plasma being the main medium for excretory product transportation). Blood plasma is prepared by spinning a tube of fresh blood containing an anti-coagulant in a centrifuge until the blood cells fall to the bottom of the tube. The blood plasma is then poured or drawn off. "Blood serum" is blood plasma without fibrinogen or the other clotting factors (i.e., whole blood minus both the cells and the clotting factors).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR 2 ("amidate"), P(O)R, P(O)OR', CO or CH 2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Amplification," as used herein, generally refers to the process of producing multiple copies of a desired sequence. "Multiple copies" means at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The term "array" or "microarray", as used herein refers to an ordered arrangement of hybridizable array elements, such as polynucleotide probes (e.g., oligonucleotides), beads, or binding reagents (e.g., antibodies), on a substrate. The substrate can be a solid substrate, such as a glass or silica slide, a fiber optic binder, or a semi-solid substrate, such as nitrocellulose membrane. The nucleotide sequences can be DNA, RNA, or any permutations thereof.

As used herein, the term "phenotype" refers to a trait which can be compared between individuals, such as presence or absence of a condition, a visually observable difference in appearance between individuals, metabolic variations, physiological variations, variations in the function of biological molecules, and the like. A phenotype can be qualitative or quantitative. An example of a phenotype is responsiveness to a treatment, such as a drug.

"Responsiveness" can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e., reduction, slowing down or complete stopping) of disease spread; (6) relief, to some extent, of one or more symptoms associated with the disorder; (7) increase in the length of disease-free presentation following treatment; (8) decreased mortality at a given point of time following treatment; and/or (9) lack of adverse effects following treatment. Responsiveness can also be assessed using any endpoint indicating side effect and/or toxicity to the patient.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. For example, significant reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

The term "prediction" or "prognosis" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will survive or improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc.

As used herein, the term "specifically binds" refers to the binding specificity of a specific binding pair. Recognition by an antibody of a particular target in the presence of other potential targets is one characteristic of such binding. Specific binding involves two different molecules wherein one of the molecules specifically binds with the second molecule through chemical or physical means. The two molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like. A molecule may also be an SBP member for an aggregation of molecules; for example, an antibody raised against an immune complex of a second antibody and its corresponding antigen may be considered to be an SBP member for the immune complex.

As used herein, the term "homologue" is used to refer to a nucleic acid which differs from a naturally occurring nucleic acid (i.e., the "prototype" or "wild-type" nucleic acid) by minor modifications to the naturally occurring nucleic acid, but which maintains the basic nucleotide structure of the naturally occurring form. Such changes include but are not limited to: changes in one or a few nucleotides, including deletions (e.g., a truncated version of the nucleic acid) insertions and/or substitutions. A homologue can have enhanced, decreased, or substantially similar properties as compared to the naturally occurring nucleic acid. A homologue can be complementary or matched to the naturally occurring nucleic acid. Homologues can be produced using techniques known in the art for the production of nucleic acids including, but not limited to, recombinant DNA techniques, chemical synthesis, etc.

As used herein, "complementary" or "matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C.

Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

As used herein, the term "output" refers to a value or score generated from a computer algorithm. The output may be generated based on assay results using the biomarkers disclosed herein as inputs to the computer algorithm. An "output" can be either quantitative or qualitative, and can be used for determining the likely responsiveness of a subject to a treatment in a companion diagnostic test.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

C. Enumerated Embodiments

The following enumerated embodiments are representative of some aspects of the invention.

In a first embodiment, (1) the invention provides a method for preventing and/or treating pulmonary hypertension and/or emphysema in a subject in need of prevention and/or treatment, which method comprises administering an effective amount of:
  a) an agent that provides for or enhances level and/or an activity of Fragile Histidine Triad (FHIT); and/or
  b) Enzastaurin,
to said subject.

2. The method of embodiment 1, which is used to prevent emphysema in a subject.

3. The method of embodiment 1, which is used to treat emphysema in a subject.

4. The method of embodiment 1, which is used to prevent pulmonary hypertension in a subject.

5. The method of embodiment 1, which is used to treat pulmonary hypertension in a subject.

6. The method of embodiment 4 or 5, wherein the pulmonary hypertension belongs to WHO Group 1, pulmonary arterial hypertension (PAH); WHO) Group I', pulmonary veno-occlusive disease (PVOD) or pulmonary capillary hemangiomatosis (PCH); WHO Group 1", persistent pulmonary hypertension of the newborn; WHO(Group II, pulmonary hypertension secondary to left heart disease; WHO Group III, pulmonary hypertension due to lung disease or chronic hypoxia, WHO Group IV, chronic arterial obstruction; or WHO Group V, pulmonary hypertension with unclear or multifactorial mechanisms.

7. The method of embodiment 6, wherein the subject has elevated right ventricle systolic pressure (RVSP), right ventricle hypertrophy, cardiac fibrosis, pulmonary vasculature remodeling, e.g., blood vessel loss, vessel muscularization and/or neointima formation, or emphysema.

8. The method of embodiment 6, wherein the pulmonary hypertension is pulmonary hypertension (PH), pulmonary arterial hypertension (PAH), chronic obstructive pulmonary disease (COPD) or emphysema.

9. The method of any one of embodiments 1-8, wherein the pulmonary hypertension or emphysema develops spontaneously (e.g., idiopathic PH) in a subject.

10. The method of any one of embodiments 1-8, wherein the pulmonary hypertension or emphysema develops based on the genetic background (e.g., familial PH) of a subject.

11. The method of any one of embodiments 1-8, wherein the pulmonary hypertension or emphysema develops due to or in association with another disease or disorder, such as secondary to chronic obstructive pulmonary disease (COPD).

12. The method of any one of embodiments 1-11, wherein an effective amount of an agent that provides for production of FHIT, or a functional fragment thereof, is administered to a subject.

13. The method of embodiment 12, wherein the agent comprises a polynucleotide that is configured to produce FHIT, or a functional fragment thereof, in the subject.

14. The method of embodiment 13, wherein the polynucleotide is a DNA molecule that encodes FHIT, or a functional fragment thereof.

15. The method of embodiment 13, wherein the polynucleotide is an RNA molecule that encodes FHIT, or a functional fragment thereof.

16. The method of embodiment 12, wherein the agent comprises a polypeptide comprising FHIT, or a functional fragment thereof.

17. The method of any one of embodiments 1-11, wherein an effective amount of an agent, e.g., a microRNA such as miRNA17-5, microRNA24a, a microRNA mimic or a microRNA antagomir, or a demethylation agent such as decitabine, that enhances the level of FHIT, or a functional fragment thereof, is administered to a subject.

18. The method of embodiment 17, wherein the agent, e.g., Enzastaurin, enhances expression of a DNA molecule that encodes FHIT, or a functional fragment thereof, in the subject.

19. The method of embodiment 17, wherein the agent enhances translation of an RNA molecule that encodes FHIT, or a functional fragment thereof, in the subject.

20. The method of embodiment 17, wherein the agent enhances stability of FHIT, or a functional fragment thereof, in the subject.

21. The method of embodiment 20, wherein the agent comprises activated Gαq or an agonist binding to Gq-coupled receptor that leads to Gαq activation and dissociation with Gβy complex. [see Hao et al., Cell Communication and Signaling, 11(1):59, August 2013]

22. The method of embodiment 21, wherein the agent blocks or reduces degradation of FHIT, or a functional fragment thereof, in the subject.

23. The method of embodiment 22, wherein the agent blocks or reduces phosphorylation of FHIT, or a functional fragment thereof, e.g., Src-mediated phosphorylation of FHIT at the Tyr114 site, in the subject.

24. The method of any one of embodiments 1-11, wherein an effective amount of an agent that enhances an activity of FHIT is administered to a subject.

25. The method of any one of embodiments 1-11, wherein an effective amount of Enzastaurin is administered to a subject.

26. The method of embodiment 25, wherein an effective amount of Enzastaurin is administered to a subject to prevent emphysema in the subject.

27. The method of embodiment 25, wherein an effective amount of Enzastaurin is administered to a subject to treat emphysema in the subject.

28. The method of embodiment 25, wherein an effective amount of Enzastaurin is administered to a subject to prevent pulmonary hypertension in the subject.

29. The method of embodiment 25, wherein an effective amount of Enzastaurin is administered to a subject to treat pulmonary hypertension in the subject.

30. The method of any one of embodiments 1-29, wherein the agent and/or Enzastaurin upregulates FHIT and/or bone morphogenetic protein receptor type-2 (BMPR2) in a subject.

31. The method of embodiment 30, wherein the agent and/or Enzastaurin upregulates FHIT and/or BMPR2 via a microRNA, e.g., miR17-5 and/or miR27a, in the subject.

32. The method of embodiment 30 or 31, wherein the agent and/or Enzastaurin upregulates FHIT and BMPR2 in the subject.

33. The method of any one of embodiments 30-32, wherein the agent and/or Enzastaurin upregulates BMPR2 independent of the agent and/or Enzastaurin upregulation of FHIT in a subject.

34. The method of any one of embodiments 1-33, wherein the agent and/or Enzastaurin prevents and/or treats pulmonary hypertension and/or emphysema independent of PKC inhibition in a subject.

35. The method of any one of embodiments 1-34, wherein the agent and/or Enzastaurin prevents and/or treats pulmonary hypertension and/or emphysema by improving right ventricular systolic pressure (RVSP), RV hypertrophy, cardiac fibrosis and/or vascular remodeling in a subject.

36. The method of any one of embodiments 1-35, wherein the agent and/or Enzastaurin prevents and/or treats pulmonary hypertension and/or emphysema by preventing or reducing RVSP increase, RVH increase, vascular rarefaction, muscularization and/or neointima formation of distal vessels in a subject.

37. The method of any one of embodiments 1-36, wherein an effective amount of an agent and/or Enzastaurin is administered to a subject having or suspected of having an end-stage PH.

38. The method of embodiment 37, wherein the end-stage PH is characterized by pulmonary vascular obliteration, increased RVSP, e.g., RVSP>100 mmHg, increased mean PAP and/or PVR, right heart failure, increased RVH, reduced RV function and RV dilatation, and/or increased interstitial fibrosis.

39. The method of embodiment 37 or 38, wherein the treatment with the agent and/or Enzastaurin increases FHIT and/or BMPR2 expression in whole lung, reducing or reversing pulmonary vascular occlusion(s), and/or reducing at least one of muscularization of small and large vessels, RVH, RV fibrosis, RV dilatation and RVSP, mean PAP, PVR as well as increasing RV function.

40. The method of embodiment 39, wherein the pulmonary artery mean pressure (PAPm) and the pulmonary vascular resistance (PVR) are reduced, and the cardiac output (CO) is increased in the treated subject.

41. The method of any one of embodiments 1-40, wherein the subject having or suspected of having a low level of BMPR2 or having or suspected of having a BMPR2 mutation.

42. The method of embodiment 41, wherein the subject has a BMPR2 level at or below a BMPR2 level of a subject that does not have pulmonary hypertension and/or emphysema.

43. The method of embodiment 41, wherein the subject has a point mutation, addition and/or deletion in BMPR2 gene, e.g., a point mutation in the ligand binding, kinase and/or tail region of BMPR2.

44. The method of any one of embodiments 1-43, wherein the subject having or suspected of having a low level of FHIT or having or suspected of having a FHIT mutation.

45. The method of embodiment 44, wherein the subject has a FHIT level at or below a FHIT level of a subject that does not have pulmonary hypertension and/or emphysema.

46. The method of embodiment 44, wherein the subject has a point mutation, addition and/or deletion in FHIT gene, and/or abnormal methylation status of FHIT gene.

47. The method of any one of embodiments 1-46, wherein the agent and/or Enzastaurin is administered at a dosage ranging from about 5 mg/day to about 1,000 mg/day.

48. The method of any one of embodiments 1-47, wherein the agent and/or Enzastaurin is administered at a dosage to obtain an in vivo level, e.g., serum or plasma concentration, ranging from about 20 nmol/L to about 6,000 nmol/L. In certain of these embodiments, the in vivo level is a plasma concentration from about 20 nmol/L to about 6000 nmol/L. In some of these embodiments, the in vivo level is a plasma concentration from about 500 nmol/L to about 2500 nmol/L, or from about 100 nmol/L to about 500 nmol/L, or from about 20 nmol/L to about 100 nmol/L.

49. The method of any one of embodiments 1-48, which further comprises administering a pharmaceutically acceptable carrier or excipient to a subject.

50. The method of any one of embodiments 1-49, which further comprises administering an effective amount of a second prophylactic or therapeutic agent for preventing and/or treating pulmonary hypertension and/or emphysema in a subject.

51. The method of embodiment 50, wherein the second prophylactic or therapeutic agent for preventing and/or treating pulmonary hypertension is a vasoactive substance, a prostaglandin, an endothelin receptor antagonist, a phosphodiesterase type 5 inhibitor or an activator of soluble guanylate cyclase.

52. The method of embodiment 50 or 51, wherein the second prophylactic or therapeutic agent for preventing and/or treating emphysema is a bronchodilating medication, a steroid medication or an antibiotic.

53. The method of any one of embodiments 1-52, wherein the agent and/or Enzastaurin is administered via an oral, nasal, inhalational, parental, intravenous, intraperitoneal, subcutaneous, intramuscular, intradermal, topical, or rectal route.

54. The method of any one of embodiments 1-53, wherein an effective amount of the agent and/or Enzastaurin is administered to a subject to reduce systemic blood pressure of the subject.

55. The method of any one of embodiments 1-54, wherein the treatment results in improving at least one parameter that is symptomatic of PAH in the treated subject. In some embodiments, this means the treatment reduces mean PAP pulmonary artery pressure (PAPm) below 25 mm Hg and preferably below 20 mmHg, reduces PVR below 3 WU, and/or increases PAWP (pulmonary artery wedge pressure) above 15 in the subject. In some embodiments, improving at least one parameter symptomatic of PAH refers to measurably improving right ventricular systolic pressure (RVSP) or pulmonary artery systolic pressure (PASP) measured, or both, measured via electrocardiograph. In some embodiments, improving at least one parameter symptomatic of PAH refers to measurably improving mean pulmonary artery pressure (PAPm), pulmonary artery wedge pressure (PAWP), cardiac output (CO), and/or pulmonary vascular resistance (PVR), which can be measured, e.g., by right heart catherization. In one such embodiment, a subject having PAPm>25 mm Hg before treatment exhibits PAPm<25 mm Hg and preferably <20 mm Hg after treatment. In another embodiment, a subject having Group 1 PAH and exhibiting PAPm>25, and PVR>3 WU, and PAWP<15 before treatment has at least one parameter improved, e.g., PAPm<25, and/or PVR>3 WU, and/or PAWP>15, after treatment.

56. The method of any one of embodiments 1-55, wherein the subject is a mammal.

57. The method of embodiment 56, wherein the mammal is a human.

58. The method of embodiment 56, wherein the mammal is a non-human mammal.

59. Use of an effective amount of an agent that provides for or enhances level and/or an activity of Fragile Histidine Triad (FHIT) in a subject and/or Enzastaurin for the manufacture of a medicament for preventing and/or treating pulmonary hypertension and/or emphysema in said subject.

60. A combination, which combination comprises:
1) an agent that provides for or enhances level and/or an activity of Fragile Histidine Triad (FHIT) in a subject and/or Enzastaurin; and
2) a second prophylactic or therapeutic agent for preventing and/or treating pulmonary hypertension and/or emphysema.

In some such embodiments, the second prophylactic or therapeutic agent is selected from Isordil (isosorbide dinitrate), Revatio (sildenafil), Tracleer (bosentan), Letairis (ambrisentan), Flolan (epoprostenol), Adcirca (tadalafil), Remodulin (treprostinil) Ventavis (iloprost), Tyvaso (treprostinil), Dilatrate-SR (isosorbide dinitrate), Isordil Titradose (isosorbide dinitrate), IsoDitrate (isosorbide dinitrate), and Isochron (isosorbide dinitrate). Typically, the combination comprises at least one and preferably two or more pharmaceutically acceptable excipients.

61. A pharmaceutical composition, which comprises an effective amount of a combination of embodiment 60, and a pharmaceutically acceptable carrier or excipient.

62. A method for preventing and/or treating pulmonary hypertension and/or emphysema in a subject in need of prevention and/or treatment, which method comprises administering an effective amount of a combination of embodiment 60 or a pharmaceutical composition of embodiment 61 to said subject.

63. A method for assessing pulmonary hypertension and/or emphysema in a subject, which method comprises:
a) providing a sample from a subject;
b) assessing FHIT and/or BMPR2 level and/or activity in said sample to assess pulmonary hypertension and/or emphysema in said subject.

64. The method of embodiment 63, wherein the sample is a blood, serum, plasma, or body fluid sample, or any combination thereof.

65. The method of embodiment 63 or 64, wherein the subject is a mammal.

66. The method of embodiment 65, wherein the mammal is a non-human mammal, e.g., a pet, a farm animal, a companion animal or an experimental animal.

67. The method of embodiment 65, wherein the mammal is a human.

68. The method of any one of embodiments 63-67, which further comprises comparing the FHIT and/or BMPR2 level and/or activity assessed in b) with a threshold or reference value, e.g., FHIT and/or BMPR2 level and/or activity from a comparable subject that has normal blood pressure, and the FHIT and/or BMPR2 level and/or activity assessed in b) lower than the threshold or reference value indicates that said subject has or has a higher risk of having pulmonary hypertension and/or emphysema.

69. The method of any one of embodiments 63-68, wherein a level of a polynucleotide that encodes FHIT and/or BMPR2 in a sample is assessed.

70. The method of embodiment 69, wherein the polynucleotide is a DNA molecule that encodes FHIT and/or BMPR2.

71. The method of embodiment 69, wherein the polynucleotide is an RNA molecule that encodes FHIT and/or BMPR2.

72. The method of any one of embodiments 63-71, wherein a level of a polynucleotide that encodes FHIT and/or BMPR2 in a sample is assessed using a procedure that comprises amplifying, ligating, hybridizing and/or sequencing said polynucleotide.

73. The method of embodiment 72, wherein the polynucleotide is amplified using a procedure selected from the group consisting of polymerase chain reaction (PCR), strand displacement amplification (SDA), transcription mediated amplification (TMA), ligase chain reaction (LCR), nucleic acid sequence based amplification (NASBA), primer extension, rolling circle amplification (RCA), self sustained sequence replication (3SR), and loop-mediated isothermal amplification (LAMP).

74. The method of embodiment 72, wherein the sequencing is conducted with a format selected from the group consisting of Maxam-Gilbert sequencing, a chain-termination method, shotgun sequencing, bridge PCR, single-molecule real-time sequencing, ion semiconductor (ion torrent sequencing), sequencing by synthesis, sequencing by ligation (SOLiD sequencing), chain termination (Sanger sequencing), massively parallel signature sequencing (MPSS), polony sequencing, 454 pyrosequencing, Illumina (Solexa) sequencing, DNA nanoball sequencing, heliscope single molecule sequencing, single molecule real time (SMRT) sequencing, nanopore DNA sequencing, tunnelling currents DNA sequencing, sequencing by hybridization, sequencing with mass spectrometry, microfluidic Sanger sequencing, a microscopy-based technique, RNAP sequencing, and in vitro virus high-throughput sequencing.

75. The method of any one of embodiments 63-74, wherein a level of a polypeptide that comprises FHIT and/or BMPR2 in a sample is assessed.

76. The method of embodiment 75, wherein the level of a polypeptide that comprises FHIT and/or BMPR2 in a sample is assessed using an immunoassay.

77. The method of embodiment 76, wherein the immunoassay is selected from the group consisting of an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (IFA), nephelometry, flow cytometry assay, surface plasmon resonance (SPR), chemiluminescence assay, lateral flow immunoassay, u-capture assay, inhibition assay and avidity assay.

78. The method of any of embodiments 63-77, which is used for diagnosis, prognosis, stratification, risk assessment, or treatment monitoring of pulmonary hypertension and/or emphysema in a subject.

79. The method of any one of embodiments 63-78, which has sensitivity of at least 50%.

80. The method of any one of embodiments 63-79, which has specificity of at least 50%.

81. The method of any one of embodiments 63-80, which further comprises treating a subject or altering treatment of a subject based on the assessment of pulmonary hypertension and/or emphysema in the subject.

82. The method of embodiment 81, which comprises treating a human patient or altering treatment of a human patient based on the assessment of pulmonary hypertension and/or emphysema in the human patient.

83. A method of reducing pulmonary hypertension and emphysema in a mammal, comprising: administering an effective amount of Fragile Histidine Triad (FHIT)-elevating agent Enzastaurin or other FHIT-elevating agents to the mammal having pulmonary hypertension or emphysema, wherein the administered dosage is below 1000 mg/day and is sufficient to reduce blood pressure of said mammal.

84. The method of embodiment 83, wherein said mammal is human.

85. The method of embodiment 83, wherein said dosage provides a predicted FHIT-elevating agent Enzastaurin or other FHIT-elevating agents serum concentration of or below 3500 nmol/L.

86. The method of embodiment 83, wherein said administering is oral.

87. A method of reducing pulmonary hypertension or emphysema in a mammal with low or undetectable levels of FHIT, comprising:
 a. obtaining a blood sample from the mammal;
 b. determining the level of FHIT in the blood sample; and
 c. administering an effective amount of FHIT-elevating agent Enzastaurin or other FHIT-elevating agents to the mammal having pulmonary hypertension or emphysema, if the sample has a low or undetectable level of FHIT.

88. The method of embodiment 87, wherein said mammal is human.

89. The method of embodiment 87, wherein said dosage provides a predicted FHIT-elevating agent Enzastaurin or other FHIT-elevating agents serum concentration of or below 3500 nmol/L.

90. The method of embodiment 87, wherein said administering is oral.

91. A method of reducing pulmonary hypertension or emphysema in a mammal with low or undetectable levels of FHIT, comprising:
 a. obtaining a tissue sample from the mammal;
 b. determining the level of FHIT in the tissue sample; and
 c. administering an effective amount of FHIT-elevating agent Enzastaurin or other FHIT-elevating agents to the mammal having pulmonary hypertension or emphysema, if the sample has a low or undetectable level of FHIT.

92. The method of embodiment 91, wherein said mammal is human.

93. The method of embodiment 91, wherein said dosage provides a predicted FHIT-elevating agent Enzastaurin or other FHIT-elevating agents serum concentration of or below 3500 nmol/L.

94. The method of embodiment 91, wherein said administering is oral.

95. A method of reducing pulmonary hypertension or emphysema in a mammal with low or undetectable levels of BMPR2, comprising:
 a. obtaining a blood sample from the mammal;
 b. determining the level of BMPR2 in the blood sample; and
 c. administering an effective amount of FHIT-elevating agent Enzastaurin or other FHIT-elevating agents to the mammal having pulmonary hypertension or emphysema, if the sample has a low or undetectable level of BMPR2.

96. The method of embodiment 95, wherein said mammal is human.

97. The method of embodiment 95, wherein said dosage provides a predicted FHIT-elevating agent Enzastaurin or other FHIT-elevating agents serum concentration of or below 3500 nmol/L.

98. The method of embodiment 95, wherein said administering is oral.

99. A method of reducing pulmonary hypertension or emphysema in a mammal with low or undetectable levels of BMPR2, comprising:
 a. obtaining a tissue sample from the mammal;

b. determining the level of BMPR2 in the tissue sample; and c. administering an effective amount of FHIT-elevating agent Enzastaurin or other FHIT-elevating agents to the mammal having pulmonary hypertension or emphysema, if the sample has a low or undetectable level of BMPR2.

100. The method of embodiment 99, wherein said mammal is human.

101. The method of embodiment 99, wherein said dosage provides a predicted FHIT-elevating agent Enzastaurin or other FHIT-elevating agents serum concentration of or below 3500 nmol/L.

102. The method of embodiment 99, wherein said administering is oral.

103. A method of reducing pulmonary hypertension or emphysema in a mammal with low or undetectable levels of BMPR2, comprising:

a. obtaining a tissue sample from the mammal;

b. determining the level of BMPR2 in the tissue sample; and c. administering an effective amount of FHIT-elevating agent Enzastaurin or other FHIT-elevating agents to the mammal having pulmonary hypertension or emphysema, if the sample has a low or undetectable level of BMPR2.

104. The method of embodiment 103, wherein said mammal is human.

105. The method of embodiment 103, wherein said dosage provides a predicted FHIT-elevating agent Enzastaurin or other FHIT-elevating agents serum concentration of or below 3500 nmol/L.

106. The method of embodiment 103, wherein said administering is oral.

107. A method of reducing pulmonary hypertension or emphysema in a mammal with a mutation of BMPR2, comprising:

a. obtaining a tissue sample from the mammal;

b. analyzing the tissue sample for a BMPR2 mutation; and c. administering an effective amount of FHIT-elevating agent Enzastaurin or other FHIT-elevating agents to the mammal having pulmonary hypertension or emphysema, if a BMPR2 mutation was detected.

108. The method of embodiment 107, wherein said mammal is human.

109. The method of embodiment 107, wherein said dosage provides a predicted FHIT-elevating agent Enzastaurin or other FHIT-elevating agents serum concentration of or below 3500 nmol/L.

110. The method of embodiment 107, wherein said administering is oral.

111. A method of reducing pulmonary hypertension or emphysema in a mammal with a mutation of BMPR2, comprising:

a. obtaining a blood sample from the mammal;

b. analyzing the blood sample for a BMPR2 mutation; and c. administering an effective amount of FHIT-elevating agent Enzastaurin or other FHIT-elevating agents to the mammal having pulmonary hypertension or emphysema, if a BMPR2 mutation was detected.

112. The method of embodiment 111, wherein said mammal is human.

113. The method of embodiment 111, wherein said dosage provides a predicted FHIT-elevating agent Enzastaurin or other FHIT-elevating agents serum concentration of or below 3500 nmol/L.

114. The method of embodiment 111, wherein said administering is oral.

115. A method of reducing pulmonary hypertension or emphysema in a mammal with a mutation of FHIT, comprising:

a. obtaining a tissue sample from the mammal;

b. analyzing the tissue sample for a FHIT mutation; and c. administering an effective amount of FHIT-elevating agent Enzastaurin or other FHIT-elevating agents to the mammal having pulmonary hypertension or emphysema, if a FHIT mutation was detected.

116. The method of embodiment 115, wherein said mammal is human.

117. The method of embodiment 115, wherein said dosage provides a predicted FHIT-elevating agent Enzastaurin or other FHIT-elevating agents serum concentration of or below 3500 nmol/L.

118. The method of embodiment 115, wherein said administering is oral.

119. A method of reducing pulmonary hypertension or emphysema in a mammal with a FHIT mutation, comprising:

a. obtaining a blood sample from the mammal;

b. analyzing the blood sample for a FHIT mutation; and c. administering an effective amount of FHIT-elevating agent Enzastaurin or other FHIT-elevating agents to the mammal having pulmonary hypertension or emphysema, if a FHIT mutation was detected.

120. The method of embodiment 119, wherein said mammal is human.

121. The method of embodiment 119, wherein said dosage provides a predicted FHIT-elevating agent Enzastaurin or other FHIT-elevating agents serum concentration of or below 3500 nmol/L.

122. The method of embodiment 119, wherein said administering is oral.

123. The method of any one of embodiments 83-122, wherein said compound 'FHIT-elevating agent Enzastaurin or other FHIT-elevating agents' is also known as LY317615, D04014.

124. The method of any one of embodiments 83-122, wherein the pulmonary hypertension or emphysema presents with any one of the following: elevated right ventricle systolic pressure (RVSP), right ventricle hypertrophy, cardiac fibrosis, pulmonary vasculature remodeling (i.e., blood vessel loss and vessel muscularization) or emphysema.

125. The method of any one of embodiments 83-122, wherein the pulmonary hypertension or emphysema can develop spontaneously (Idiopathic PH).

126. The method of any one of embodiments 83-122, wherein the pulmonary hypertension or emphysema can develop based on the genetic background (Familial PH).

127. The method of any one of embodiments 83-122, wherein the pulmonary hypertension or emphysema can develop associated with another disease, such as secondary to Chronic Obstructive Pulmonary Disease (COPD).

128. The method of any one of embodiments 83-122, where FHIT-elevating agent Enzastaurin or other FHIT-elevating agents is used as a preventative measure for mammals with risk factors (i.e., positive mutation status for BMPR2 or FHIT).

129. The method of any one of embodiments 83-128, wherein Pulmonary hypertension or emphysema refers to WHO Classification Group I (Pulmonary Arterial Hypertension), Group II (Pulmonary Venous Hypertension), Group III (Pulmonary Hypertension Associated with Chronic Lung Disease), Group V (Miscellaneous).

130. The method of any one of embodiments 83-129 wherein pulmonary hypertension or emphysema are prevented or reversed independent of PKC inhibition, but instead through the novel signaling molecule FHIT.

131. The method of any one of embodiments 83-130, wherein agents refers to pharmaceuticals, chemicals, bioengineered treatment methods and genetic modification through techniques, such as CRISPR.

132. Use of an FHIT-elevating agent to treat pulmonary hypertension.

133. The use according to embodiment 132, wherein the FHIT-elevating agent is Enzastaurin.

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

The present invention relates to methods of using FHIT as a biological marker in conjunction with the treatment of pulmonary arterial hypertension using FHIT-elevating agent Enzastaurin or other FHIT-elevating agents. The present invention relates to the treatment of pulmonary arterial hypertension using FHIT-elevating agent Enzastaurin or other FHIT-elevating agents in familial and idiopathic Pulmonary arterial hypertension. The present invention also relates to the use of FHIT-elevating agent Enzastaurin or other FHIT-elevating agents alone or in conjunction with previously prescribed medications in order to ameliorate the vascular occlusive phenotype, pulmonary vessel loss, elevated right ventricle systolic pressure, emphysema, cardiac fibrosis and right ventricle hypertrophy present in pulmonary arterial hypertension.

The methods described herein are applicable for treating pulmonary hypertension in patients with any of the following: elevated right ventricle systolic pressure, right ventricle hypertrophy, pulmonary vessel neo-muscularization of previously unmuscularized vessels and the increase in their circumference, pulmonary vessel loss, elevated pulmonary vessel neointima formation, and elevated pulmonary vessel media hypertrophy.

Effectiveness or progress of treatment for pulmonary hypertension can be measured using methods and parameters known in the art. For example, electrocardiography can be used to measure RVSP and PASP, as an indirect measure of PH status. Right heart catheterization can be used to measure mean PPAP (PAPm), PAWP, cardiac output and PVR. Pulmonary Hypertension in general is defined as a PAPm>25 mmHg. The Group 1 PAH is sometimes defined as PAPm>25, PVR>3 WU as well a PAWP<15.

In a Phase II trial, FHIT-elevating agent Enzastaurin showed tolerability for 6 months in the duration of the study (Gray et al., Cancer 2013 119(5):1023-1032). Reported side-effects included rash, abdominal distension, hyponatremia, DVT and hypotension.

Due to the high tolerability, minimal toxicity and low amount and severity of side-effects achieved with this drug, it is useful as a treatment for pulmonary hypertension and the prevention of the development of familial pulmonary hypertension in at-risk individuals, such as a positive mutation status of BMPR2. The pulmonary hypertension disease reversal achieved with FHIT-elevating agent Enzastaurin is unprecedented and its use as a treatment strategy for pulmonary hypertension is suggested here. Furthermore, the effectiveness of Enzastaurin indicates that other FHIT-elevating agents can be used for such treatments, also.

The FHIT-elevating agent Enzastaurin or other FHIT-elevating agents may be administered alone or in combination with other active compounds that treat or prevent PH. The other active compound may be administered at a different time or at the same time as the FHIT-elevating agent Enzastaurin or other FHIT-elevating agents and in certain embodiments the FHIT-elevating agent Enzastaurin or other FHIT-elevating agents and the other active compound may be present in the same formulation, or as separate formulations in the same kit. Exemplary other active compounds that treat PH include, e.g., prostacyclin analogues, endothelin receptor antagonists, phosphodiesterase-5 inhibitors, high-dose calcium channel blockers, anticoagulants, diuretics or antiproliferative agents. In particular cases, the other active compound may be, for example, Isordil (isosorbide dinitrate), Revatio (sildenafil), Tracleer (bosentan), Letairis (ambrisentan), Flolan (epoprostenol), Adcirca (tadalafil), Remodulin (treprostinil) Ventavis (iloprost), Tyvaso (treprostinil), Dilatrate-SR (isosorbide dinitrate), Isordil Titradose (isosorbide dinitrate), IsoDitrate (isosorbide dinitrate) or Isochron (isosorbide dinitrate).

BMPR2 signaling is severely impaired in FPAH patients compared to unaffected mutation carriers(29, 42, 43) suggesting: i) a threshold of BMPR2 expression or signaling below which PAH develops, ii) the presence of BMPR2-modifying factors, or iii) additional pathways that contribute to PAH pathogenesis.

We identified FHIT and LCK in an extensive siRNA HTS of more than >22,000 genes, as novel BMPR2 modifier genes. To confirm a likely clinical importance in PAH, we cross-validated gene expression of both genes in a novel multi-cohort, multi-tissue analysis of PAH transcriptome databases that included all PAH etiologies and confirmed that FHIT was consistently and severely downregulated in all datasets. As downregulation of LCK was more variable, we mainly focused in this study on understanding the role of FHIT in PAH. FHIT was most consistently downregulated in PBMCs, which are thought to be valid surrogates for ubiquitous gene expression in PAH patients(35, 42, 44, 45, 46). We validated our findings of reduced FHIT expression in human PAH lymphocytes, PAECs and lung tissue respectively.

We propose that FHIT is a modifier gene that contributes to variable penetrance of PAH in predisposed individuals with a BMPR2 mutation consistent with the multiple-hit-theory of PAH development. In support, the low penetrance of BMPR2 mutations in PAH of 20%(1) is comparable to the genetic predisposition of mammary carcinoma by BRCA1 mutations with likewise only 20-45% penetrance(47). FHIT serves as a disease-sensitizer in sporadic breast cancer, where a one allele loss of BRCA1 and FHIT, resulted in a poor prognosis with a more aggressive phenotype(47). Similarly, simultaneous loss of FHIT and p53 in lung cancer, predisposed for aggressive lung cancer by dysregulating pro-proliferative pathways(48). Decreased FHIT was a prerequisite, but not sufficient to induce a carcinogenous phenotype in vitro(49), consistent with the increased genomic instability in Fhit−/− mice(50).

We further propose that low FHIT levels might also contribute to the observed low levels of BMPR2 in non-familial PAH patients, given that we measured reduced FHIT expression across different PAH etiologies. The mechanism of reduced FHIT expression in PAH is unknown and warrants further investigation. Epigenetic silencing or heterozygous loss of FHIT may occur due to its location on the fragile site FRA3B(13), where strand breakages commonly appear following hypoxia or carcinogen exposure, such as cigarette smoke(51-53). Despite the reported independence of FHIT expression from FRA3B site breakage in healthy adults(54), the increased mutagen sensitivity and potential concomitant defects in the DNA damage repair system through p53(55) may predispose PAH patients to FHIT reductions. Alternatively, hypermethylation of FHIT or its promoter(56-58) observed in malignancies such as lung cancer(59-63) may also account for low FHIT expression in PAH.

We confirmed that FHIT was an upstream-regulator of BMPR2 and Id1 and that Enzastaurin, a drug previously shown to increase FHIT expression(64), increased FHIT, BMPR2 and Id1 expression in PAECs. To mechanistically understand how FHIT might regulate BMPR2 signalling, we assessed the expression of selected BMPR2-regulatory microRNAs. Both miR17-5 and miR100 target BMPR2 in vascular(30, 65) and non-vascular cells alike(30, 65, 66). MiR17-5 down-regulates BMPR2 via Interleukin-6/STAT3 mediated signaling(67). Reduced FHIT expression increases miR17-5, an effect rescued by Enzastaurin. Reduced FHIT expression increases miR27a, a miRNA shown to be increased in PBMC of end-stage PAH patients(11). MiR27a inhibition seems beneficial as it reduced PAEC proliferation (30) and prevented PASMC growth in the pulmonary artery via BMPR2/PPARγ(68). Like miR17-5, Enzastaurin was able to rescue the increase in miR27a induced by FHIT loss. Inhibiting miR17-5 antagomirs rescued the siFHIT induced BMPR2 repression, and might therefore present a promising treatment strategy, as similar approaches have recently shown(32, 69)—the caveat being that targeting single microRNAs likely represents too much of a reductionist approach to achieve significant improvement of vascular remodeling in human PAH.

Figure 12:
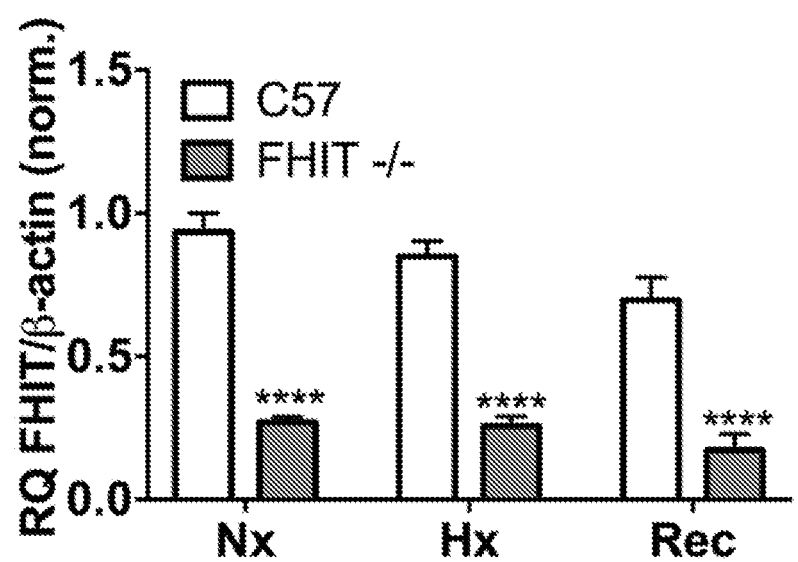
FIG. 12: FHIT protein expression in Fhit−/− mice compared to C57BL/6 controls in normoxia versus 3 weeks chronic hypoxia as well as 4 weeks re-oxygenation.

Fhit−/− mice develop pulmonary hallmarks of PAH: Muscularization of small arteries and distal artery rarefaction, exaggerated PH after hypoxia, as well as a failure to recover after re-oxygenation. In that respect Fhit−/− mice strongly resemble mice with an endothelial deletion of Bmpr2(70). In addition to reduced Fhit expression throughout the experiment, Fhit−/− mice developed reduced BMPR2 levels in hypoxia compared to C57 mice, potentially accounting for the more severe PH phenotype in hypoxia. While BMPR2 levels normalized after 4 weeks re-oxygenation, Fhit−/− mice still failed to fully recover, which could be explained either by a slower recovery from a more severe vascular damage/dysfunction in Fhit−/− mice or additional BMPR2-independent roles of FHIT required for recovery. See FIG. 12.

Vascular dysfunction in PAH is thought to be initiated by endothelial injury and early apoptosis leading to pulmonary vessel loss(12), followed by proliferation of apoptosis resistant vascular cells(71). Heightened baseline DNA damage and mutagen-sensitivity in vivo(26, 34, 35), that may predate disease onset(72), likely further contribute to EC vulnerability. FHIT-loss leads to an increased sensitization to mutagen damage and therefore might pose a risk factor for vascular injury and failed recovery. As shown herein, reduced levels of FHIT and BMPR2 are associated with vascular dysfunction; causing apoptosis, impaired tube formation and increased DNA damage in PAECs as well as heightened proliferation of PASMCs, consistent with the reported aggravation of DNA damage upon FHIT-loss in preneoplasia(73). Strategies that increase BMPR2 signaling on the other hand—as shown by using Enzastaurin—improved these vascular phenotypes(7, 12, 74, 75).

FHIT is known to suppress EGFR/Src/ERK/Slug-regulated endothelial mesenchymal transition (EndMT) in lung cancer cells. Reduced FHIT levels therefore could facilitate EndMT, and together with the increased proliferation of SMCs with low FHIT levels, could explain the increase in αSMA-positive cells, medial hypertrophy and adventitial hypertrophy of distal pulmonary vessels that we have observed(76-78). The vascular rarefaction observed in Fhit−/− mice may be attributed to increased PAEC apoptosis in distal arteries, defects in cell-cell adhesion or migration of PAEC to sites of vascular injury, as evidenced by increased numbers of circulating EC in PAH patients(79).

As a proof-of-concept for the potential use of Enzastaurin in BMPR2 deficient PAH patients, we first investigated Enzastaurin in Bmpr2+/− and wild-type C57BL/6 mice and provided evidence that a 2-week treatment with Enzastaurin (15 mg/kg/day) attenuated hypoxia-induced PH, as measured by changes in RVSP, RVH and pulmonary physiology. For potential translational relevance, we found an additive effect of FK506 and Enzastaurin treatment in mice.

We then set out to test Enzastaurin in the SUGEN5416/Hypoxia/Normoxia rat model that develops severe pulmonary vascular remodeling that most closely mimics the human disease(41) including the severe neointima formation and RV failure(80), thus being superior to mouse models and the Monocrotaline rat model that develops severe PH predominantly due to medial hypertrophy(81). Few studies have demonstrated reversal of established PH in SUGEN5416/Hypoxia/Normoxia rats(6, 12, 32, 82, 83). We found that low-dose Enzastaurin (5 mg/kg/day) potently reversed SUGEN5416/Hypoxia/Normoxia-induced lung and RV damage by increasing FHIT and BMPR2 signaling. The interpretation of the finding is limited though based on the small sample size. While Enzastaurin is evaluated as a PKCβ inhibitor in cancer(21), we did not observe a significant decrease in PKC activation as measured by its phosphorylation (FIG. 13) in whole lung tissue after Enzastaurin treatment of SUGEN5416/Hypoxia/Normoxia treated rats. We confirmed that Enzastaurin increased FHIT and BMPR2 at low doses (5-15 uM) in vitro (FIG. 14) and that Enzastaurin differs from other selective PKCβ and global PKC inhibitors with regards to its potential to modulate FHIT, BMPR2 and ID as well as is effect on PAEC function (FIG. 15, FIG. 16). This might be due to our relative low-dose Enzastaurin treatment in vivo compared to previous clinical trials(84, 85), in vivo rodent studies(86) and doses required to achieve reductions in PKC phosphorylation in vitro(87). We therefore propose that the effect of Enzastaurin on vascular remodeling as well as FHIT expression that we observed is largely PKC-independent. How Enzastaurin increases FHIT is unknown; yet one potential mechanism may be Scr-mediated inhibition of FHIT phosphorylation and prevention of its subsequent degradation(88, 89).

Data herein demonstrates a role for FHIT in PAH pathogenesis as a BMPR2 modifier gene, providing insight into BMPR2 regulation as well as opportunities for PAH intervention. FHIT expression is consistently downregulated in PAH. Reduced FHIT levels reduce BMPR2 expression and signaling, and FHIT loss in vivo leads to exaggerated experimental PH in response to hypoxia. FHIT expression can be readily increased by Enzastaurin, which was beneficial in the prevention and treatment of experimental PH in Bmpr2+/− mice and SUGEN5416/Hypoxia/Normoxia rats. Accordingly, the data show that FHIT is a novel and potentially essential component of the BMPR2 signaling architecture in PAH and that reduced FHIT levels can predispose to PAH development. These studies demonstrate effective methods for use of Enzastaurin as a beneficial treatment for PAH.

EXAMPLES

The following examples are put forth to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

In this study, Enzastaurin (Selleckchem, Houston, Tex.) and SUGEN5416 (Tocris, Bristol, UK) were used.

Example I. FHIT −/− C57BL/6 Develop Experimental PAH in Response to Chronic Hypoxia Pulmonary arterial hypertension (PAH) is a progressive lung disease, characterized by an increased pulmonary artery pressure, right ventricle (RV) hypertrophy and ultimately right heart failure. Bone Morphogenetic Protein Receptor type 2 (BMPR2) mutations or aberrant BMPR2 signaling have been reported in many PAH patients and are linked to the pathogenesis of the disease. Modulating BMPR2 signaling with repurposed drugs is an attractive strategy to treat this devastating disease. In a siRNA High Throughput Screen, we previously discovered Fragile Histidine Triad (FHIT) as a novel BMPR2 modulatory gene. We showed that reduced FHIT expression was associated with endothelial cell dysfunction and was reduced in PAH patient PBMCs, PAECs, transformed lymphocytes and lung tissue, suggesting that low FHIT promoted pulmonary hypertension and emphysema. In vitro, FHIT and BMPR2 expression could be up-regulated by FHIT-elevating agent Enzastaurin or other FHIT-elevating agents.

Figure 1B:
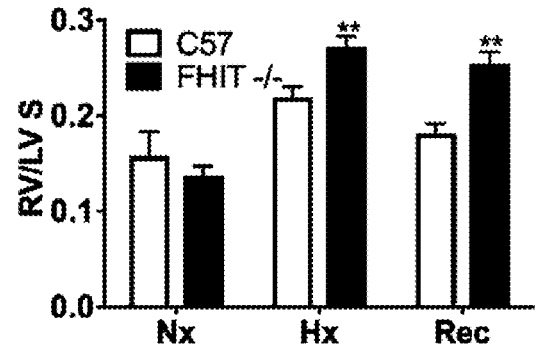
Figure 1C:
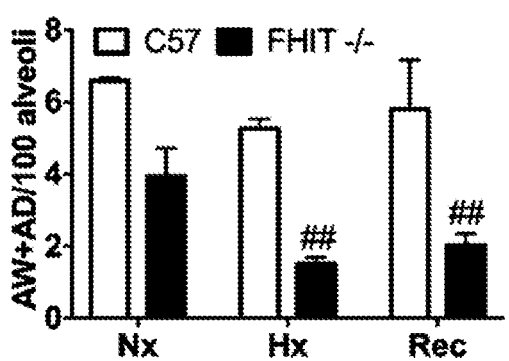
Figure 1D:
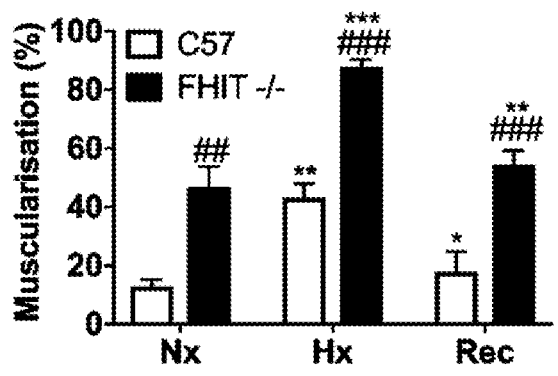
Figure 1E:
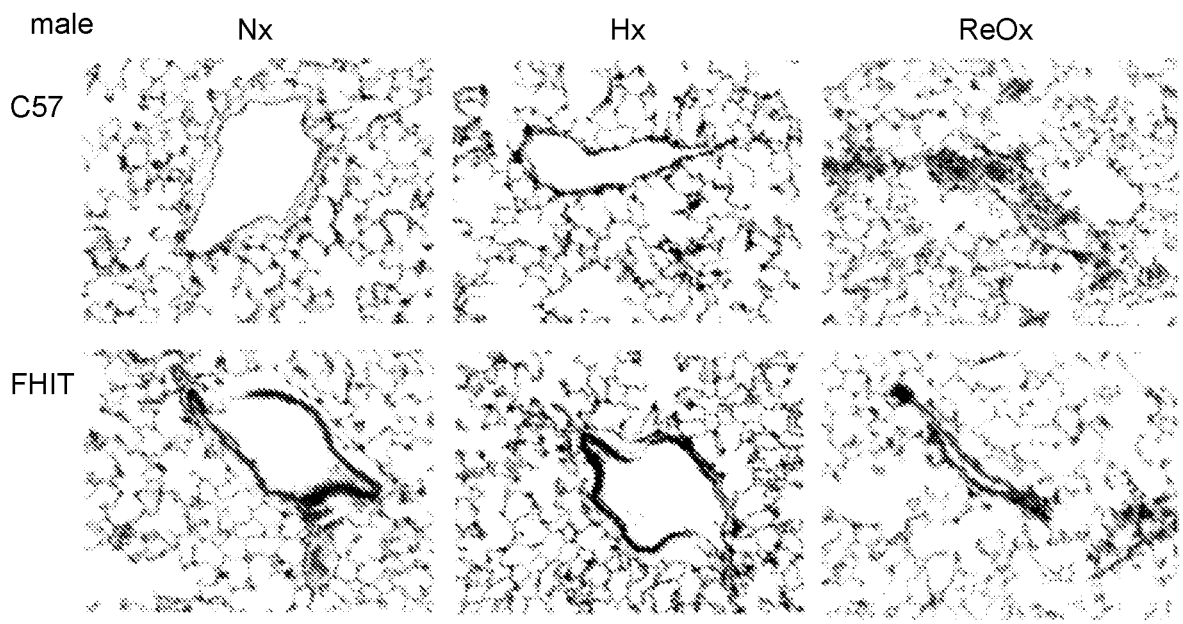
Figure 1F:
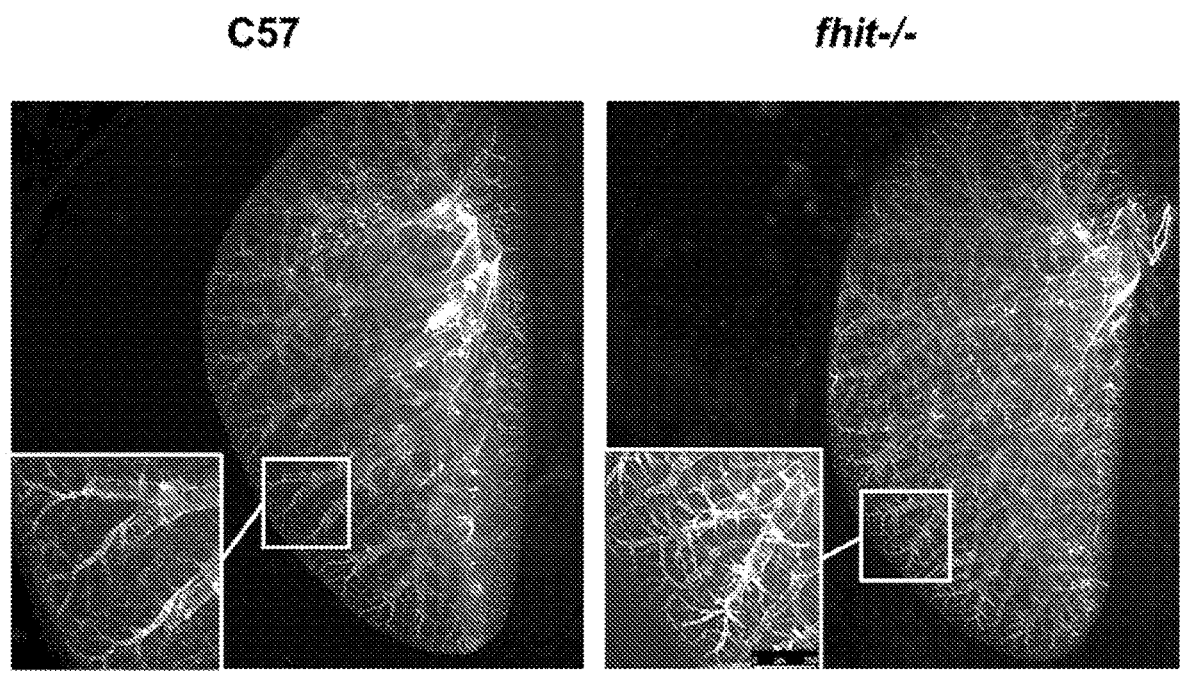
Figure 1G:
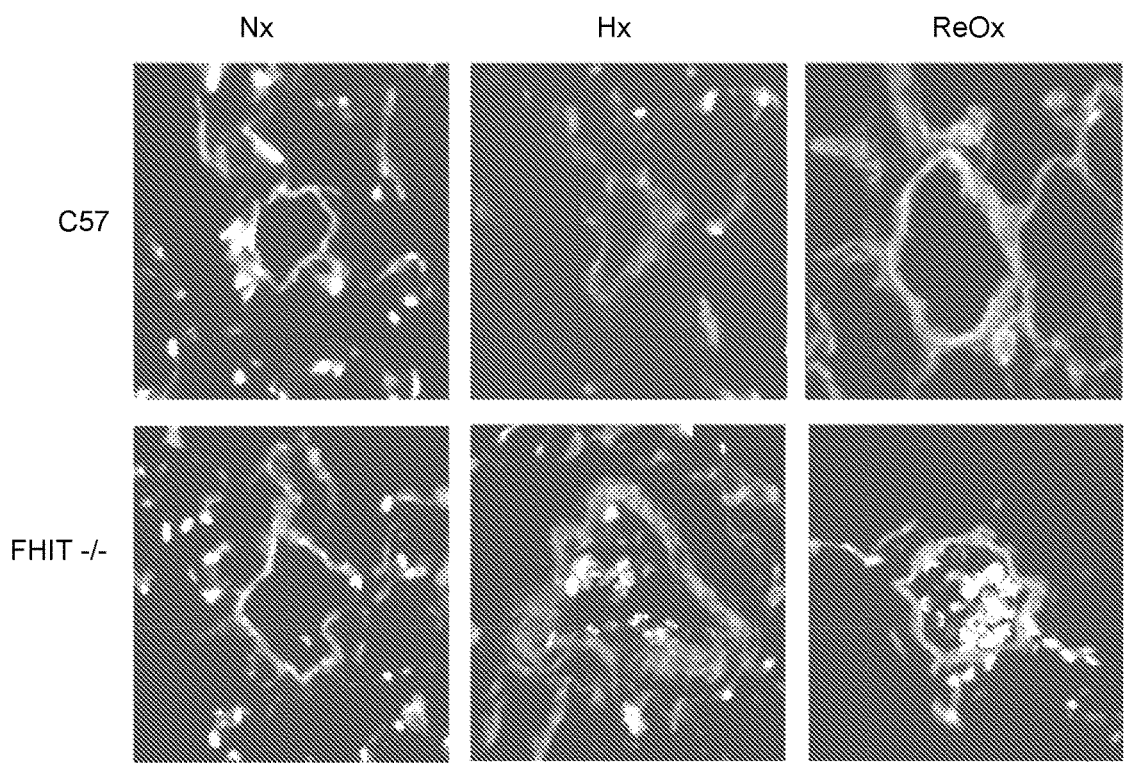
Figure 1H:
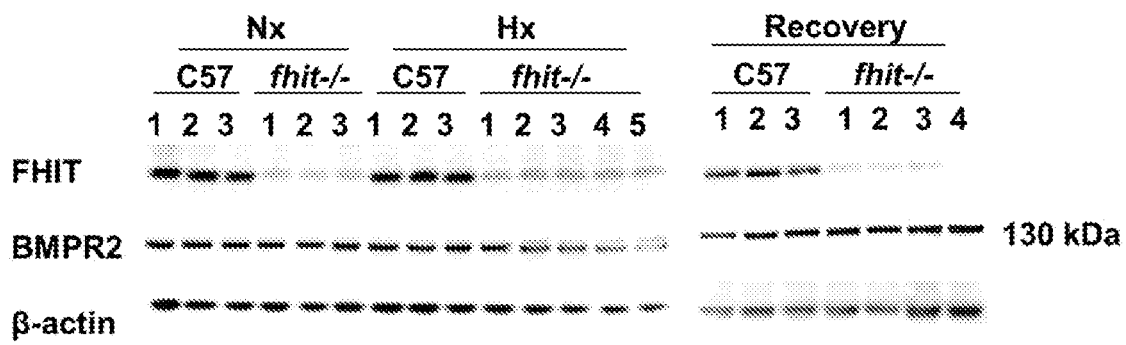
Figure 1I:
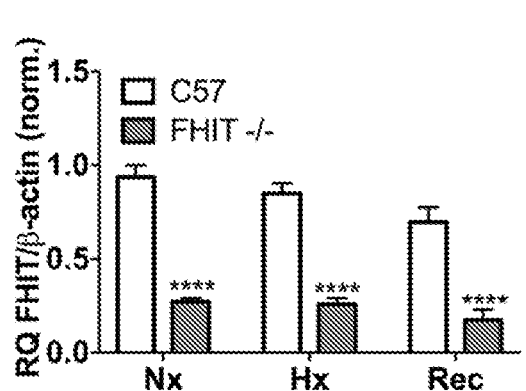
Figure 1J:
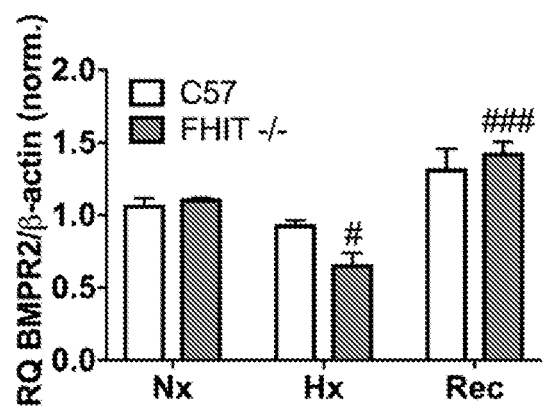
Figure 1K:
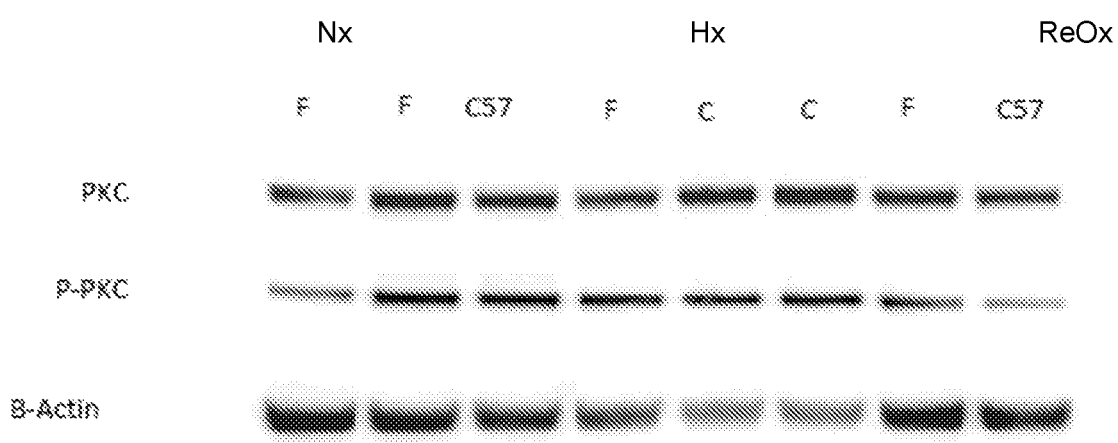

FHIT−/− C57BL/6 vs. littermate wildtype (C57) mice were housed for three weeks in normoxic (Nx, 20% $O_2$), hypoxic (Hx, 10% $O_2$) conditions, a hypoxia-recovery (Rec, 3 weeks Hx/4 weeks Nx) period for 4 weeks, compared to 7 weeks Nx controls. Results are shown in FIGS. 1A-1K for male mice: FIG. 1A, Right ventricular systolic pressure (RVSP) was measured by pulmonary artery catheterisation (male, C57 n=3, FHIT−/− Nx Rec n=3, FHIT−/− Hx n=4). FIG. 1B, Right ventricle (RV) hypertrophy is demonstrated by the weight ratio of RV to left ventricle and septum (RV/LV+S) (male, C57 NX Rec n=3, C57 Hx n=6, FHIT−/− Nx Hx n=3, FHIT−/− Rec n=4). FIG. 1C, Loss of alveolar wall (AW) and alveolar duct (AD) pulmonary vessels and FIG. 1D, their full or partial muscularization (%) was assessed in MOVAT stained lung sections (male, C57 n=3, FHIT−/− Nx n=3, FHIT−/− Hx Rec n=4). FIG. 1E, Representative MOVAT lung histology. Arrows indicate vessel position. FIG. 1F, Representative deep tissue imaging of agarose-inflated whole lobes from Nx C57 and FHIT −/− mice (n=2). FIG. 1G, Representative IF staining of pulmonary vessels with αSMA and avWF antibodies. FIG. 1H, Representative immunoblots and relative densitometric analysis of FHIT (FIG. 1I) and BMPR2 (FIG. 1J) protein expression in lung tissue normalised to a P-actin housekeeping control (male, C57 n=3, FHIT−/− Nx n=3, FHIT−/− Hx n=5, FHIT−/− Rec n=4). FIG. 1K, Representative immunoblots of PKC and Phospho PKC protein expression in lung tissue normalised to a P-actin housekeeping control (male, C57 n=3, FHIT−/− Nx n=3, FHIT−/− Hx n=5, FHIT−/− Rec n=4). *$p<0.05$, $p<0.01$, **$p<0.0001$ vs. Nx control, #$p<0.05$, ##$p<0.01$, ###$p<0.001$ vs. C57 control, Two Way ANOVA, Turkey's post-test.

Figure 2A:
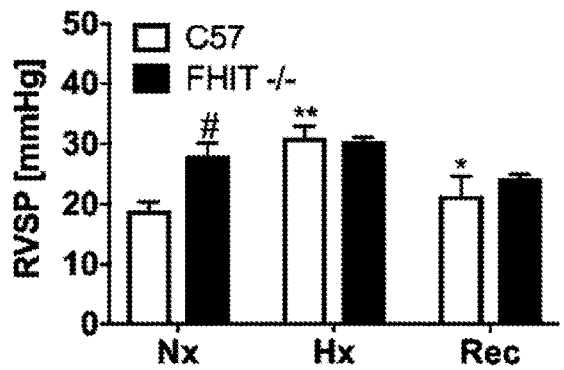
FIGS. 2A-2F: Female FHIT−/− C57BL/6 mice develop experimental PAH after chronic exposure to Hypoxia.
Figure 2B:
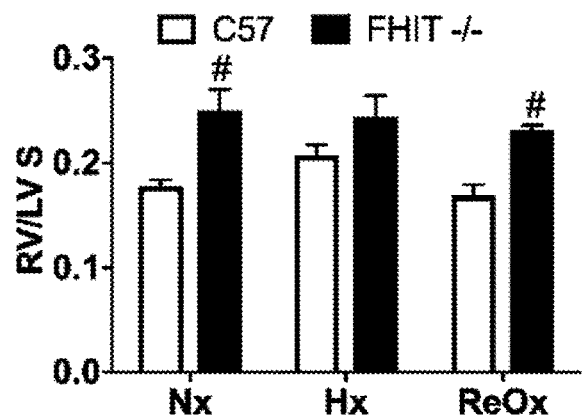
Figure 2C:
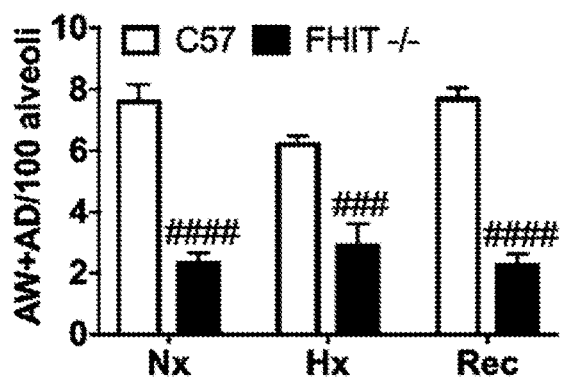
Figure 2D:
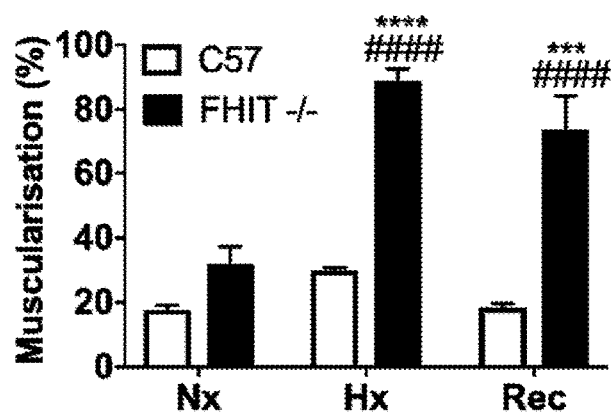
Figure 2E:
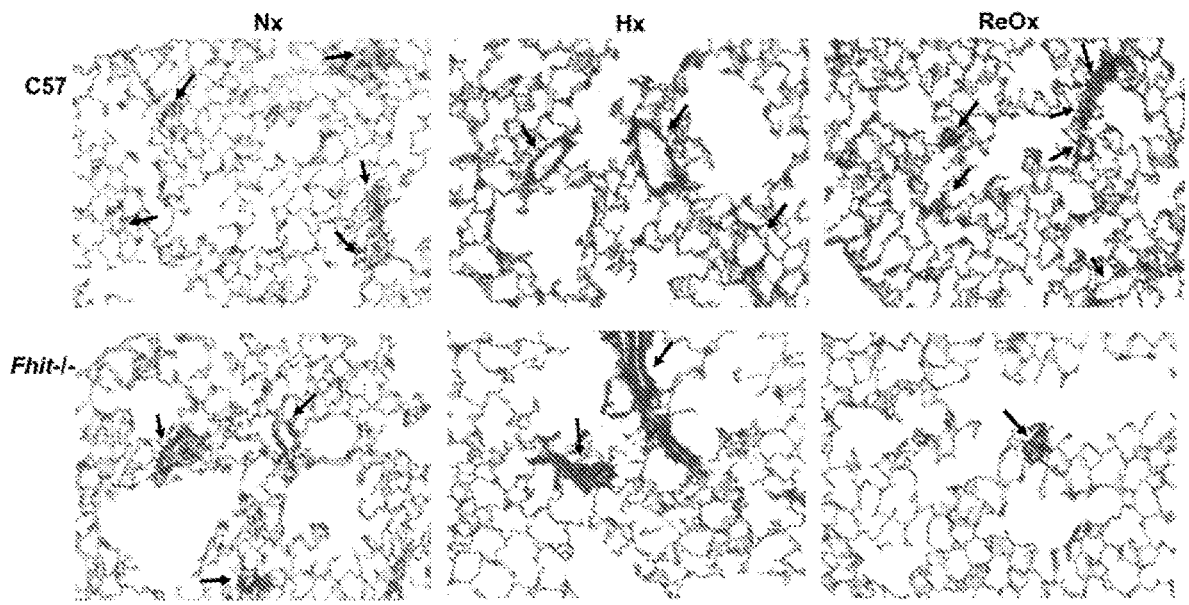
Figure 2F:
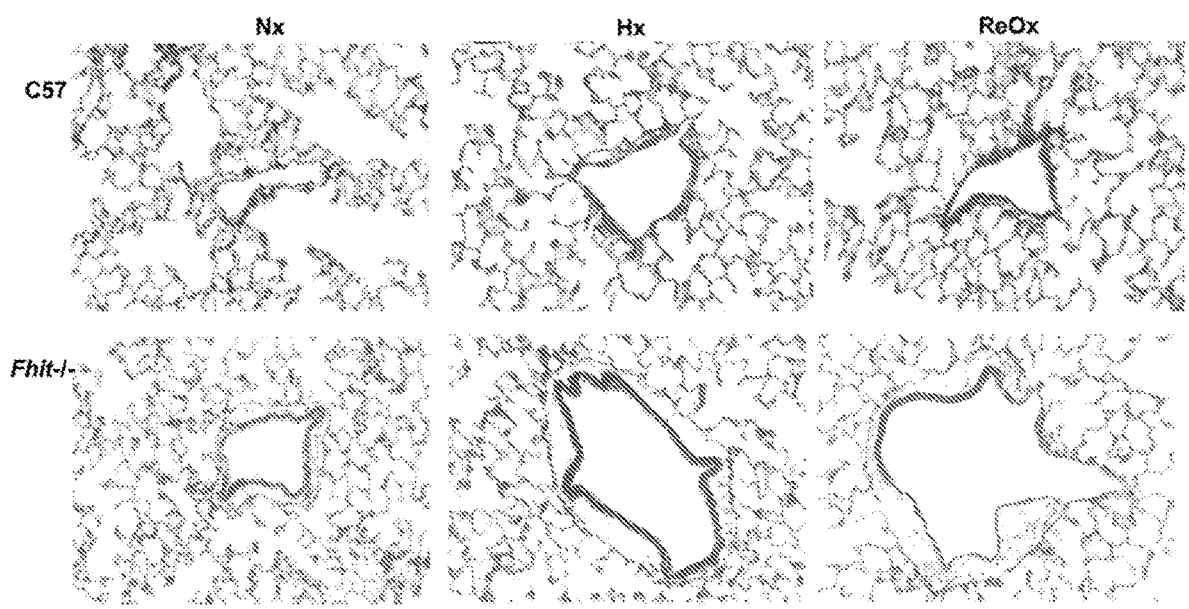

Results are shown in FIGS. 2A-2F for female mice: FHIT−/− C57BL/6 vs. littermate wildtype (C57) mice were housed for three weeks in normoxic (Nx, 20% $O_2$), hypoxic (Hx, 10% $O_2$) conditions, a hypoxia-recovery (Rec, 3 weeks Hx/4 weeks Nx) period for 4 weeks, compared to 7 weeks Nx controls. FIG. 2A, Right ventricular systolic pressure (RVSP) was measured by pulmonary artery catheterisation (female). FIG. 2B, Right ventricle (RV) hypertrophy is demonstrated by the weight ratio of RV to left ventricle and septum (RV/LV+S) (female) FI. 2C, Loss of alveolar wall (AW) and alveolar duct (AD) pulmonary vessels and FIG. 2D, their frill or partial muscularization (%) was assessed in MOVAT stained lung sections (female). FIG. 2E, Representative MOVAT lung histology depicting vessel loss. Arrows indicate vessel position. FIG. 2F, Representative MOVAT lung histology depicting vessel structure. Arrows indicate vessel position. *$p<0.05$, $p<0.01$, **$p<0.0001$ vs. Nx control, #$p<0.05$, ##$p<0.01$, ###$p<0.001$ vs. C57 control, Two Way ANOVA, Turkey's post-test.

Male and female FHIT−/− C57BL/6 mice developed experimental PAH after chronic exposure to Hypoxia. Briefly, FHIT−/− C57BL/6 vs. littermate wildtype (C57) mice were housed for three weeks in normoxic (Nx, 20% $O_2$), hypoxic (Hx, 10% $O_2$) conditions, a hypoxia-recovery (Rec, 3 weeks Hx/4 weeks Nx) period for 4 weeks, compared to 7 weeks Nx controls. Right ventricle systolic pressure (RVSP) was measured by pulmonary artery catheterization and was found to be elevated in response to hypoxia in males (FIG. 1A) and already at baseline in females (FIG. 2A). Elevated RVSP levels were maintained in both groups upon return to normoxia. Likewise, right ventricle (RV) hypertrophy was demonstrated by the elevated weight ratio of RV to left ventricle and septum (RV/LV+S) in hypoxic conditions in males (FIG. 1B) and in both normoxia and hypoxia in females (FIG. 2B). In both cases, elevated RV/LV+S ratios were maintained upon return to normoxia.

Elevated alveolar wall (AW) and alveolar duct (AD) pulmonary vessel loss (FIGS. 1C, 2C, 2E) and their full or partial muscularization (%) (FIGS. 1D, 1F-G, 2D, 2F) was found throughout all test conditions.

Western Blots to test for protein levels of FHIT, BMPR2, PKC and phosphorylated PKC confirmed decreased FHIT levels in the FHIT −/− animals, with simultaneously decreased BMPR2 levels in hypoxia. However, no change in total PKC levels or PKC phosphorylation was detected, suggesting that FHIT does not regulate PKC or PKC phosphorylation.

This experiment shows that FHIT is an important molecule in the development of pulmonary hypertension and emphysema, and its effect is independent of PKC levels and PKC phosphorylation status.

Example II Enzastaurin Prevents Hypoxia-Induced Experimental PAH Development in C57BL/6 and BMPR2+/−C57BL/6 Mice Most familial PAH patients have a BMPR2 mutation. However, the presence of a BMPR2 mutation only predisposes for, but does not alone cause the development of PAH, suggesting that a second factor contributing to the onset of the disease may be present. As FHIT is readily lost in response to stressors, such as hypoxia and cigarette smoke, it is proposed that the hypoxia-induced development of PAH in C57BL/6 and BMPR2 deficient (BMPR2+/−) C57BL/6 mice may be prevented by the use of the FHIT elevating agent FHIT-increasing chemical Enzastaurin.

Figure 3A:
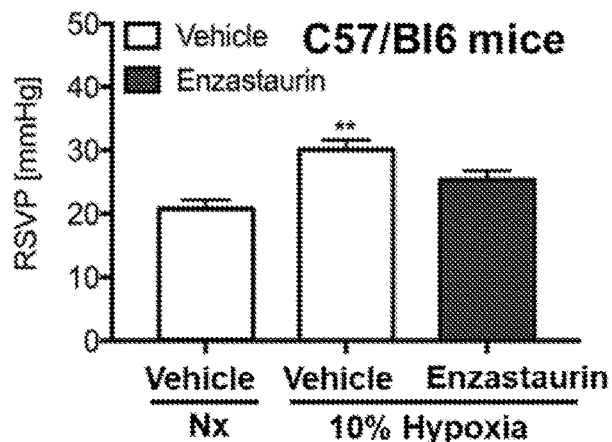
FIGS. 3A-3F: Enzastaurin prevents the development of hypoxia-induced experimental PAH in C57BL/6 mice.
Figure 3B:
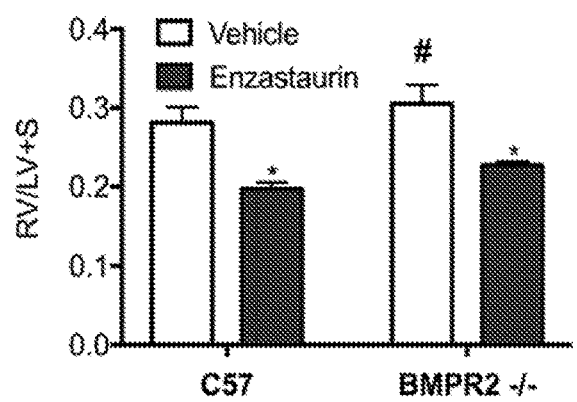
Figure 3C:
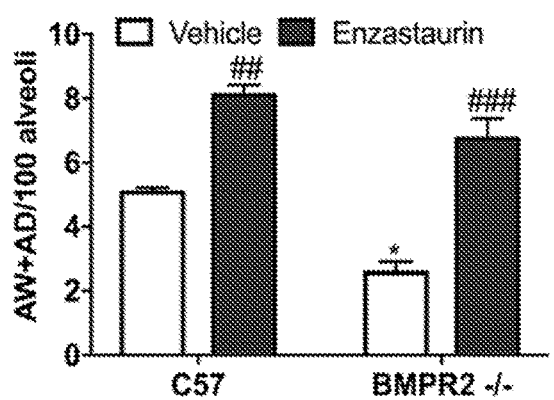
Figure 3D:
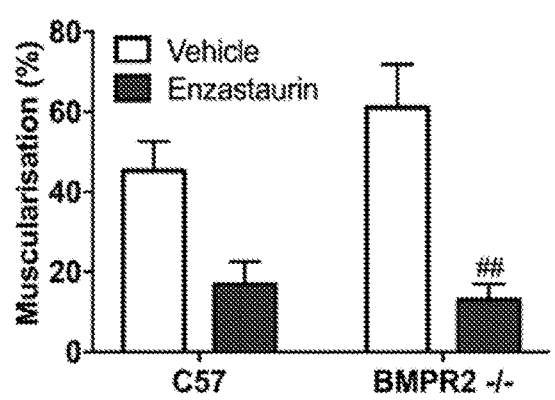
Figure 3E:
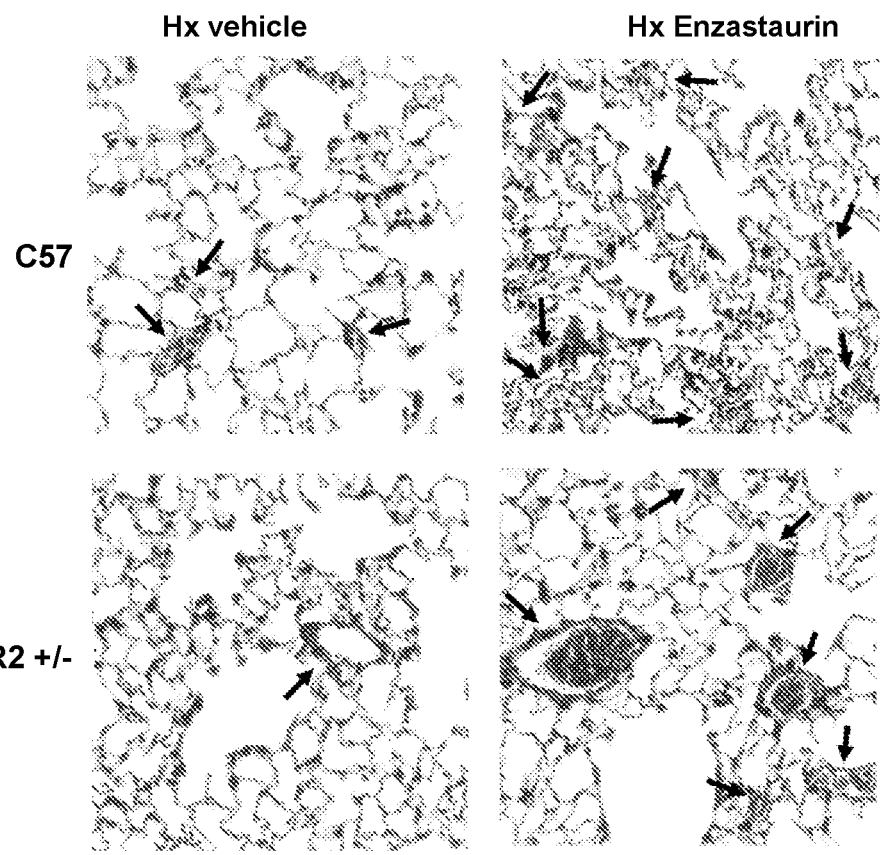
Figure 3F:
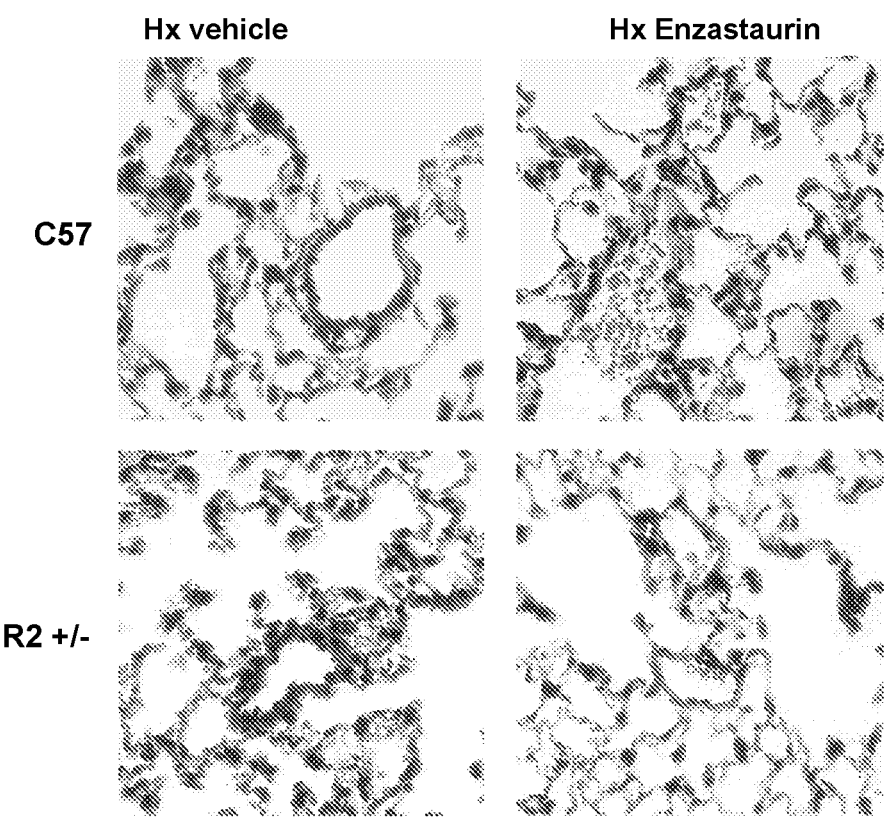

BMPR2+/− mice and C57 controls were exposed to 3 weeks of chronic hypoxia and administration of 5 mg/kg daily FHIT-elevating agent Enzastaurin or other FHIT-elevating agents through an osmotic pump. Right Ventricular (RV) Systolic Pressure was measured through right jugular vein catheterization and RV hypertrophy was assessed by the weight ratio of the RV to left ventricle+septum. Vessel loss and muscularization of lung vessels were visualized by MOVAT pentachrome stain. For this experiment, Male Wildtype and BMPR2+/−C57BL/6 (C57) mice were housed for three weeks in normnoxic (Nx, 20% $O_2$) and hypoxic (Hx, 10% $O_2$) conditions, treated with or without daily administration of 5 mg/kg Enzastaurin by Alzet mini-osmotic pump model 2006. Data are presented in FIGS. 3A to 3F: FIG. 3A, Right ventricular systolic pressure (RVSP) was measured by pulmonary artery catheterization (n=3, Mean±SEM, **$p<0.01$ vs. Nx control, One Way ANOVA, Sidak's post-test). FIG. 3B, Right ventricle (RV) hypertrophy is demonstrated by the weight ratio of RV to left ventricle and septum (n===3, Mean±SEM, #$p<0.05$ vs. vehicle control, Two Way ANOVA, Turkey's post-test). FIG. 3C, Loss of alveolar wall (AW) and alveolar duct (AD) pulmonary vessels and FIG. 3D, their full or partial muscularization (%) was assessed in MOVAT stained lung sections (n=3, Mean SEM, *$p<0.05$ vs. C57 control, ##$p<0.01$, ###$p<0.001$ vs. vehicle control, Two Way ANOVA, Turkey's post-test). FIG. 3E, Representative MOVAT lung histology depicting vessel loss. Arrows indicate vessel position. FIG. 3F, Representative MOVAT lung histology depicting vessel structure. Arrows indicate vessel position.

At high doses, far above the described Ki of the compound, the FHIT-increasing chemical Enzastaurin prevents the development of hypoxia-induced experimental PAH in C57BL/6 mice. Briefly, male wildtype and BMPR2+/− C57BL/6 (C57) mice were housed for three weeks in normoxic (Nx, 20% $O_2$) and hypoxic (Hx, 10% $O_2$) conditions, treated with or without daily administration of 5 mg/kg FHIT-increasing chemical Enzastaurin by Alzet mini-osmotic pump model 2006. FHIT-increasing chemical Enzastaurin induced a partial reduction of elevated right ventricle systolic pressure (RVSP) levels compared to the hypoxia vehicle control (FIG. 3A) and a substantial reduction in right ventricle (RV) hypertrophy, as demonstrated by the weight ratio of RV to left ventricle and septum, was observed in both C57BL/6 mice, as well as BMPR2+/− C57BL/6 mice that were housed in hypoxia (FIG. 3B). In both, C57BL/6 mice, as well as BMPR2+/−C57BL/6 mice, loss of alveolar wall (AW) and alveolar duct (AD) pulmonary vessels was significantly ameliorated by treatment with FHIT-increasing chemical Enzastaurin (FIGS. 3C, 3E), as was their full or partial muscularization (FIG. 3D, 3F).

FHIT-increasing chemical Enzastaurin prevents the development of pulmonary hypertension at high doses through the prevention of vessel loss and abrogation of vessel muscularization. In mice with decreased levels of BMPR2, FHIT-increasing chemical Enzastaurin treatment was an effective strategy to prevent development of pulmonary hypertension in response to hypoxia. The high doses required to achieve a therapeutic effect are thought to be caused by unspecific targeting of many different molecular targets at high doses.

Example III. Enzastaurin Reverses Experimental PAH in Sugen 5416/Hypoxia Rats

Administration of Sugen 5416 to rats and their subsequent exposure to chronic hypoxia results in irreversible pulmonary vascular remodelling and elevation in right ventricular systolic pressure, as well as RV hypertrophy. Therefore, this model is a model of choice for the assessment of experimental pulmonary hypertension and emphysema in vivo.

Figure 4A:
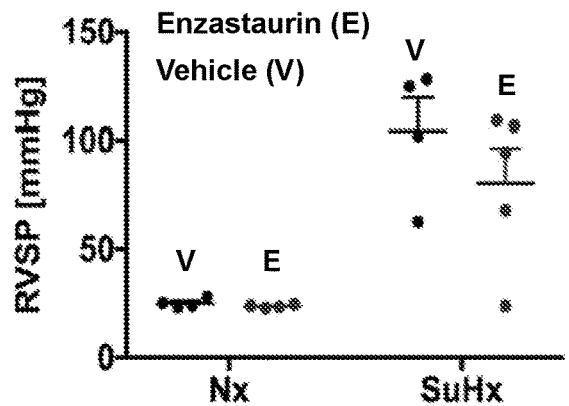
FIGS. 4A-4F: Enzastaurin reverses the Vascular occlusion, emphysema, cardiac fibrosis and improves Cardiac output in Sugen 5416/hypoxia rats.
Figure 4B:
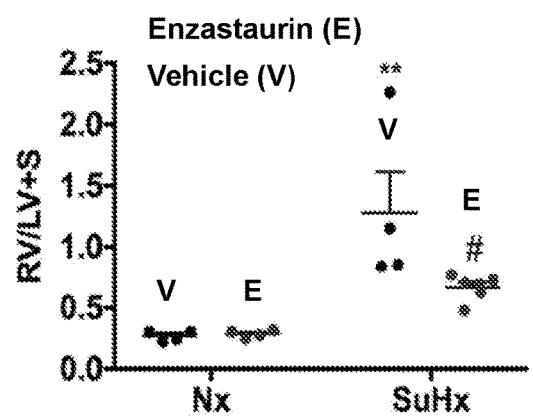
Figure 4C:
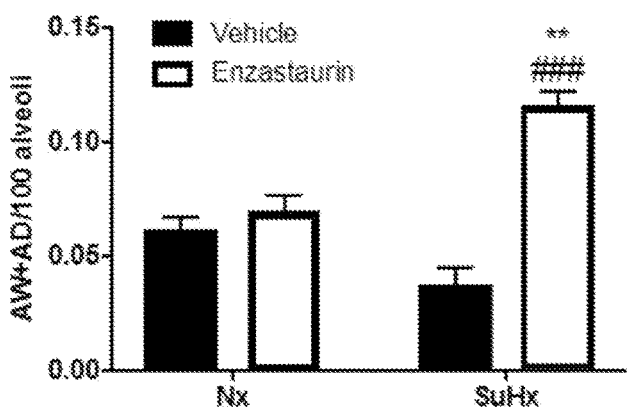

Experimental PAH was induced in male Sasco Sprague Dawley rats by subcutaneous injection of 20 mg/kg body weight SU5416. Animals were housed for 3 weeks in hypoxic (Hx, 10% $O_2$) conditions, followed by a 5 week period in normoxia (Nx, 20% $O_2$), following daily administration of 5 mg/kg body weight FHIT-elevating agent Enzastaurin or other FHIT-elevating agents or vehicle control by oral gavage. Echocardiography was performed to assess development of RV hypertrophy and Ejection Fraction. Right Ventricular (RV) Systolic Pressure was measured through right jugular vein catheterization and RV hypertrophy was assessed by the weight ratio of the RV to left ventricle+septum. Vessel loss and muscularization of lung vessels were visualized by MOVAT pentachrome stain. Data are presented in FIGS. 4A-4F: FIG. 4A, Right ventricular systolic pressure (RVSP) was measured by pulmonary artery catheterization (n=3, Mean±SEM, **$p<0.01$ vs. Nx control, One Way ANOVA, Sidak's post-test). FIG. 4B, Right ventricle (RV) hypertrophy is demonstrated by the weight ratio of RV to left ventricle and septum (n=3, Mean±SEM, #$p<0.05$ vs. vehicle control, Two Way ANOVA, Turkey's post-test). FIG. 4C, Loss of alveolar wall (AW) and alveolar duct (AD) pulmonary vessels and FIG. 4D, their full or partial muscularization (%) was assessed in MOVAT stained lung sections (n=3 Mean±SEM, *$p<0.05$ vs. C57 control, ##$p<0.01$, ###$p<0.001$ vs. vehicle control, Two Way ANOVA, Turkey's post-test). FIG. 4E, Left ventricle Ejection fraction was calculated through Echocardiographic assessment of cardiac structure and function before and after treatment with Enzastaurin for 3 weeks. FIG. 4F, Representative MOVAT lung histology.

Enzastaurin reverses the Vascular occlusion, cardiac fibrosis and improves Cardiac output in Sugen 5416/hypoxia rats. Briefly, experimental PAH was induced in male Sasco Sprague Dawley rats by subcutaneous injection of 20 mg/kg body weight SU5416. Animals were housed for 3 weeks in hypoxic (Hx, 10% $O_2$) conditions, followed by a 5 week period in normoxia (Nx, 20% $O_2$), following daily administration of 5 mg/kg body weight FHIT-increasing chemical Enzastaurin or vehicle control by oral gavage. Right ventricle systolic pressure (RVSP) (FIG. 4A) and right ventricle hypertrophy (FIG. 4B) was lower in FHIT-increasing chemical Enzastaurin treated rats with experimental pulmonary arterial hypertension than the vehicle treated controls with experimental PAH.

Figure 4D:
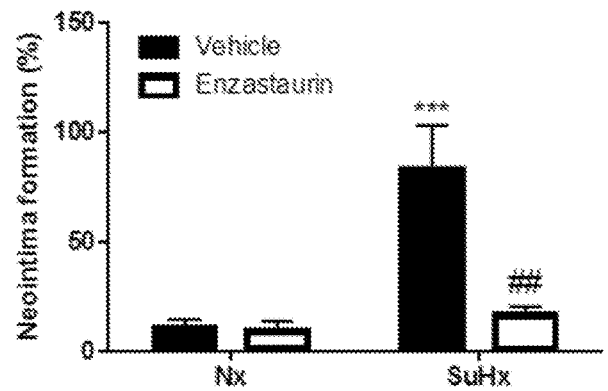
Figure 4E:
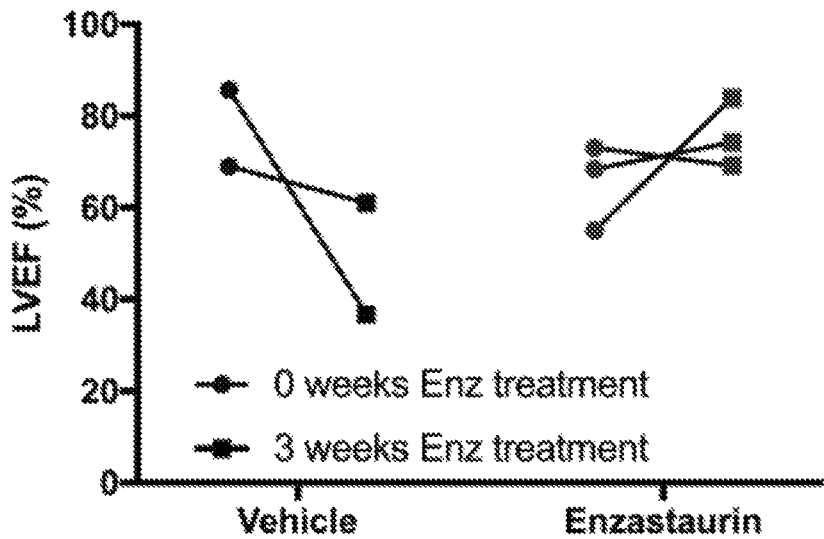
Figure 4F:
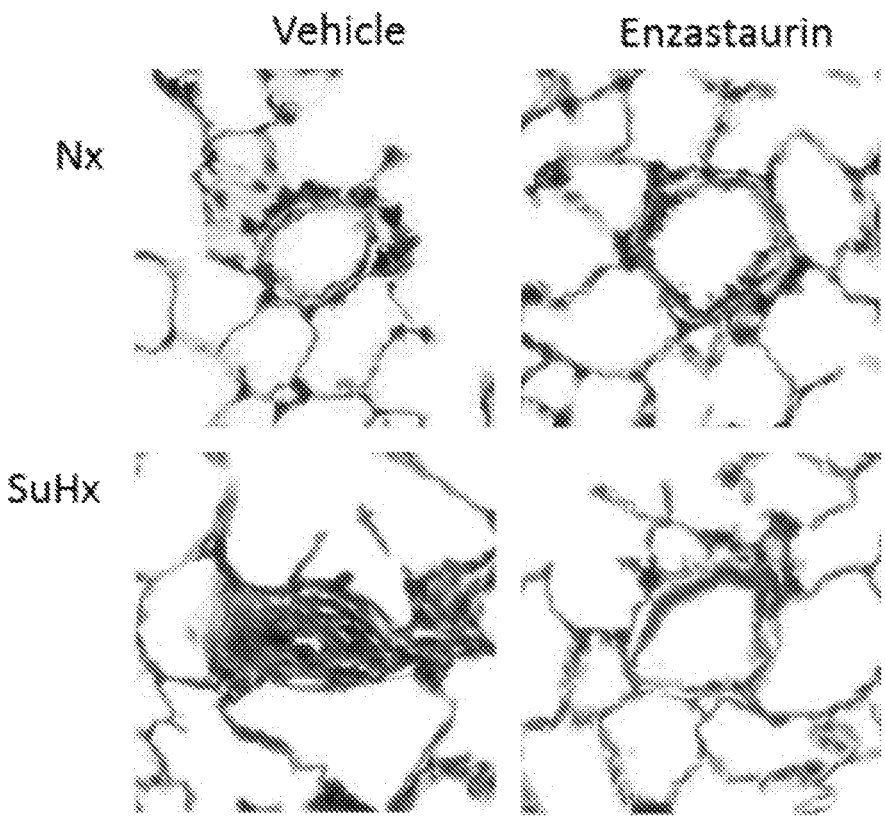

Loss of alveolar wall (AW) and alveolar duct (AD) pulmonary vessels (FIG. 4C) and their full or partial remodeling was substantially and significantly reversed by FHIT-increasing chemical Enzastaurin (FIG. 4D, 4F). This coincided with the improvement of LVEF (%), calculated by Echocardiography after treatment with FHIT-increasing chemical Enzastaurin, whereas the heart function in vehicle treated controls with experimental pulmonary hypertension and emphysema declined drastically.

FHIT-increasing chemical Enzastaurin reversed endothelial remodelling and experimental PAH in the Sugen5416/Hypoxia rat model, suggesting its use as a potent treatment strategy for PH in mammals. The high doses required to achieve a therapeutic effect are thought to be caused by unspecific targeting of many different molecular targets at high doses.

Example IV. FHIT-Increasing Chemical Enzastaurin Requires FHIT, but not PKC to Reverse Pulmonary Hypertension mRNA expression of FHIT, normalized to GAPDH was assessed in PAECs transfected with an siFHIT or non-targeting control (Ntsi) pool of 4 siRNAs, incubated with or without 15 μM FHIT-increasing chemical Enzastaurin for 24 hours. FHIT homozygous (−/−) and wildtype C57 mice are being exposed to normoxia or chronic hypoxia for 3 weeks, with or without exposure to 3 weeks of chronic hypoxia and administration of 5 mg/kg daily FHIT-elevating agent Enzastaurin or other FHIT-elevating agents through an osmotic pump. Experimental PAH will be assessed based on Right Ventricular (RV) Systolic Pressure measurements through right jugular vein catheterization and RV hypertrophy was assessed by the weight ratio of the RV to left ventricle+septum. Vessel loss and muscularization of lung vessels will be visualized by MOVAT pentachrome stain or IF staining with αSMA and avWF antibodies.

Figure 5:
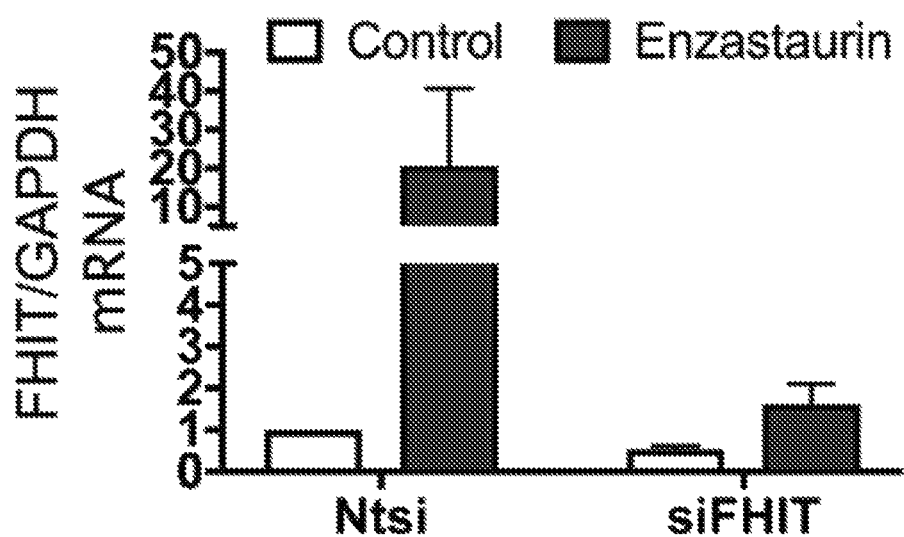
FIG. 5: Enzastaurin requires FHIT, but not PKC to reverse pulmonary hypertension.

Results are shown in FIG. 5: A. Relative mRNA expression of FHIT normalized to GAPDH in PAECs transfected with an siFHIT or non-targeting control (Ntsi) pool of 4 siRNAs (qPCR, Amaxa nucleofection, t=48h, n=3, Mean±SEM), incubated with or without 15 μM FHIT-increasing chemical Enzastaurin for 24 hours. B, Ingenuity pathway analysis of the described relations between FHIT and PKC. C, FHIT-increasing chemical Enzastaurin does not protect from pulmonary hypertension development in C57BL/6 FHIT −/− mice and fails to increase FHIT levels, while effectively downregulating PKC levels.

FHIT mRNA expression in PAEC deficient in FHIT showed that FHIT-increasing chemical Enzastaurin potently increases FHIT expression, but is unable to affect PAEC FHIT levels, once the mRNA is suppressed by siRNA (FIG. 5A).

A pathway analysis of known protein interactions with the Ingenuity pathway analysis tool demonstrated that FHIT is not thought to interact with PKC, but be involved in a separate signaling pathway, independent of PKC.

FHIT is a critical hypertension-suppressor gene that, when lost, results in the development of the devastating pulmonary hypertension phenotype. Chemicals or agents that increase FHIT expression, such as Enzastaurin, are thus expected to provide an effective treatment strategy in the prevention and treatment of pulmonary hypertension and emphysema in mammals.

Example V. High Throughput (HTS) siRNA Screen

High throughput siRNA screen of >22,000 genes using an Id1-BRE luciferase reporter assay in a C2C12 mouse myoblastoma cell line treated with or without 250 pm BMP4 was conducted as previously described(12) in the Stanford High-Throughput Bioscience Center. Briefly, C2C12 myoblastoma cells were stably transfected with BRE-Id1 linked to luciferase as a reporter cell line(E1) and screened on 72×384 well siRNA plates. The transfection conditions were optimized with BMP4 as stimulus, siBMPR2 and siTox as controls, DharmaFect3 as the transfection reagent and optimal concentrations for siRNAs (25 nM) and cell numbers/well (1500). Target genes decreased Id1 expression to <60%, comparable to siBMPR2, while maintaining a general cell viability of >70% to exclude cell death response genes. Of the resulting 579 genes, unspecific genes, such as pseudogenes, RNA polymerase subunits, RNA splicing, transport factors and ribosome units were excluded in a secondary screening approach, yielded 96 genes, which were validated by target-specific siRNA pools. Hits were defined as a ≤60% reduction in Id1 expression, as well as a stricter cell viability criteria of ≥80% with a least 2 individual siRNAs. This yielded 74 gene candidates that were cross-validated using the novel meta-analysis approach discussed below. The process and results are summarized in FIG. 6.

Animal Models.

Fhit homozygous (−/−) mice were obtained from Kay F. Huebner (Ohio State University). Bmpr2+/− mice were a gift from Marlene Rabinovitch (Stanford University). Adult wildtype C57BL/6 mice, Bmpr2+/− or Fhit−/− mice at 8-10 weeks of age were housed in chronic hypoxia (10% $O_2$) for 3 weeks, followed by a recovery period of 4 weeks in normoxia (21% $O_2$). Bmpr2+/− and Fhit−/− mice and littermates were treated with a daily dose of Enzastaurin (15 and 5 mg/kg/day) or vehicle for the duration of the study, administered mini osmotic pump. Development of experimental PH was induced in adult Sprague Dawley rats (8 weeks old, 180-220 g) through a subcutaneous dose of the VEGFR-2 inhibitor SUGEN5416 (20 mg/kg body weight), followed by exposure to chronic hypoxia (10% $O_2$) for 3 weeks and normoxia for 5 weeks (21% $O_2$), as previously described(12). SuHx rats and littermates were treated with a daily dose of Enzastaurin (5 mg/kg body weight) or vehicle for 3 weeks, administered through oral gavage. Right Ventricular (RV) Systolic Pressure was measured through right jugular vein catheterization, and RV hypertrophy (RVH) was assessed by the weight ratio of the RV to left ventricle and septum (LV+S).

All animal experiments were approved by the Stanford University Institutional Animal Care and Use Committee. Experiments involving human tissue or derived primary cells were approved by the Stanford University Institutional Review Board and the Administrative Panel on Human Subject Research.

Isolation of Cells from Human PAH Patients.

PAEC of IPAH and FPAH patients at time of lung transplant were obtained from digested whole lung tissue, using CD31-AB pulldown beads as previously described (12). Peripheral Blood Mononuclear Cells (PBMCs) were isolated from PAH patients with negative BMPR2 mutation status or healthy volunteers through Ficoll-Paque density gradient centrifugation (10). Lymphocytes from $BMPR2^{mut+}$ PAH patients and their unaffected relatives were isolated from the whole blood using gradient centrifugation and subsequently virally transformed, as previously described (23).

Histology and ICC.

Murine and rat lung tissue was fixed in paraformaldehyde (PFA) for 48 hours and preserved in EtOH. Paraffin embedded lung slides were stained with a Movat pentachrome stain (Histo-Tec, Hayward, Calif.), where vessel loss and muscularization of pulmonary vessels was visualized by light microscopy. Fluorescent immunocytochemistry on lung sections was performed on deparaffinized (Histoclear II, National Diagnostics) tissue sections with primary antibodies for von-Willebrand factor (vWF) and alpha smooth muscle actin (αSMA) following antigen-retrieval. Human PAH lung tissue was stained for anti-BMPR2 (Ab130206, Abcam) and anti-FHIT (kind gift of Kay F. Huebner, Ohio State University). PFA-fixed paraffin-embedded heart tissue was stained with trichrome staining (Histo-Tec, Hayward, Calif.) to visualize fibrotic transformation.

Cell Culture.

Human PAEC (Promocell) or human PASMC (Promocell) were grown as monolayers in gelatin-coated dishes in a commercial EC (Promocell) or SMC (Promocell) media, respectively. Cells were passaged at 1:3 ratios and used for experiments from passages 3-8. Transformed lymphocytes (i.e., lymphoblasts) were cultured in RPMI 1640 with 10-15% FBS.

Isolation of Cells from Human PAH Patients.

PAEC of IPAH and FPAH patients at time of lung transplant were obtained from digested whole lung tissue, using CD31-AB pulldown beads (Dynabeads; Invitrogen), as previously described(E1). Peripheral Blood Mononuclear Cells (PBMCs) from were isolated from the peripheral blood of end-stage PAH patients with negative BMPR2 mutation status or healthy volunteers through Ficoll-Paque density gradient centrifugation, dextran sedimentation and RBC lysis, as previously described(E8). Lymphocytes from BMPR2$^{mut+}$ PAH patients and their unaffected relatives were isolated from the whole blood using gradient centrifugation and subsequently virally transformed, as previously described(E1).

RNA Interference.

FHIT expression was modulated by RNAi in PA endothelial cells (PAEC). A pool of 4 siRNAs for BMPR2, FHIT, LCK or a non-targeting control pool (Dharmacon) were transfected into PAECs using the RNAi Max kit (Invitrogen) for 48 hours. mRNA knockdown efficiency was determined by qPCR.

qPCR Assay to Detect mRNA and miR Expression.

For mRNA, total RNA was extracted from whole lung tissue using the RNAeasy Plus Kit (Qiagen) and reverse transcribed into cDNA using random primers with the Taqman cDNA reverse transcription Kit (Applied Biosciences) according to the manufacturer's instructions. For miR, total miR was isolated from whole lung tissue using the Taqman miRNA ABC purification Kit (Applied Biosciences) and was reverse transcribed using specific primers and the Taqman microRNA reverse transcription kit (Applied Biosciences). mRNA and miR expression levels were quantified using Taqman primer/probe sets for the target and normalized to a housekeeping control (mRNA: GAPDH; miR: RNU48).

Western Blotting.

Western blotting was performed as previously described (E1). Antibodies for BMPR2 (Ab130206, monoclonal, Abcam), FHIT (NBPI-89061, polyclonal, Novus Biologicals; Ab180806, polyclonal, Abcam), PKC (Ab76016, monoclonal, Abcam), P-PKC (Ab32376, [Y124], monoclonal, Abcam), LCK (NBPI-19840, polyclonal, Novus Biologicals), p38 (Ab31828, monoclonal, Abcam), Id1 (sc133104, monoclonal, Santa Cruz Biotechnology), Smad1 (#9743, Cell Signaling), P-Smad1/5/9 (#13820P, Cell Signaling) and β-Actin (Sc47778, monoclonal, Santa Cruz) were used.

Apoptosis, DNA Damage, MTT Proliferation and Matrigel Tube Formation Assays.

Assays were conducted according to the manufacturer's instructions and as previously described(E1,E9).

Deep Tissue Imaging.

Deep tissue imaging of agarose-inflated lungs was conducted on a Leica M205FA fluorescent stereomicroscope using a Hamamatsu Orca Flash 4.0LT camera as previously described(E10,E11). Arterial muscularization in agarose-inflated lungs was assessed in arteries accompanying the left lobe secondary lateral airway branch L4 (L:L4)(E10) and was designated as branching generation 1 before the point of its bifurcation. Further descendant artery branch generations, generated by bifurcation or domain branching alike, were designated as branch generations 2-12. An increase in generation numbers was apparent for generations 6-10 in Fhit−/− mice, whereas wildtype mice did not exceed generation 7 of muscularized vessels.

Statistical Analysis.

Data were analyzed using GraphPad Prism version 7.00, GraphPad software (La Jolla, Calif.). Statistical tests were performed as appropriate and included the following: Student's t-test, One-Way ANOVA and Two-way ANOVA, followed by the appropriate post-hoc test, as indicated. Differences were considered to be statistically significant as follows: $p<0.05$ (*/#), $p<0.01$ (/##), $p<0.001$ (*/###), $p<0.0001$ (****/####).

Example VI. Meta-Analysis of Publicly Available PAH Gene Expression Data

A novel integrated meta-analysis algorithm and a validation cohort was used to cross-validate the resulting list of 74 BMPR2 modifier gene candidates from the mouse myoblastoma HTS in seven publicly available human PAH transcriptomic datasets from the NCBI Gene Expression Omnibus (GEO) (Lung: GSE15197, GSE24988, GSE48149; PBMC: GSE19617, GSE22356, GSE33463, GSE703). All samples were uniformly curated using standardized vocabularies linked to the National Library of Medicine (NLM) United Medical Language System (UMLS), a parent vocabulary which includes Gene Ontology, SNOMED-CT, ICD-9, and ICD-10, as well as over a hundred other commonly used standardized vocabularies. The 7 PAH data sets comprised 291 samples from either PAH lungs (153 samples) or PBMCs (138 samples), which were used to develop a PAH dataset. We downloaded and manually curated each dataset, as previously described(E2-E5). Briefly, the data itself was normalized and converted to log 2 using previously published methods(E6). We used two different meta-analysis approaches, called (i) combining fold changes and (ii) combining p-values as previously described(E7). Differentially expressed genes were selected that (i) had a specific false discovery rate threshold <10%, and (ii) were expressed in the same direction (up- or downregulated) in at least 75% of the studies. To account for data dominance, caused by the unequal sample number, we removed one data set at a time for the meta-analysis.

The 74 targets from the mouse myoblastoma HTS were validated in human lung and PBMC PAH datasets to ensure that potential BMPR2 modifier genes were important in human PAH samples. A double screening approach was deemed necessary to account for healthy control subject variability, determining gene targets that are most relevant for human disease and most consistently regulated.

In addition to comparing the HTS siRNA results with the PAH gene expression datasets, we predicted an anti-PAH signature, which essentially is characterized by an opposite gene expression to the PAH signature. The availability of gene expression profile datasets for drugs allows identification of FDA-approved drugs that may beneficial to treat PAH. We integrated a reference collection of gene-expression profiles from cultured human cells treated with bioactive small molecules. The database LINCS profiled a large number of drugs across many cell lines. LINCS is the largest database of gene expression profiles of cultured human cells treated with different drugs. At the time of analysis, there were 20,413 chemical perturbagens profiled on LINCS across 18 "gold" cell lines on the L1000 platform (www.lincscloud.org). With this technique we predicted which genes Enzastaurin and Dasatinib would target and whether the gene expression profile would be more similar to the PAH signature or anti-signature.

Example VII. HTS of BMPR2 Modulators and Multi-Cohort PAH Gene Expression Assay

Figure 6A:
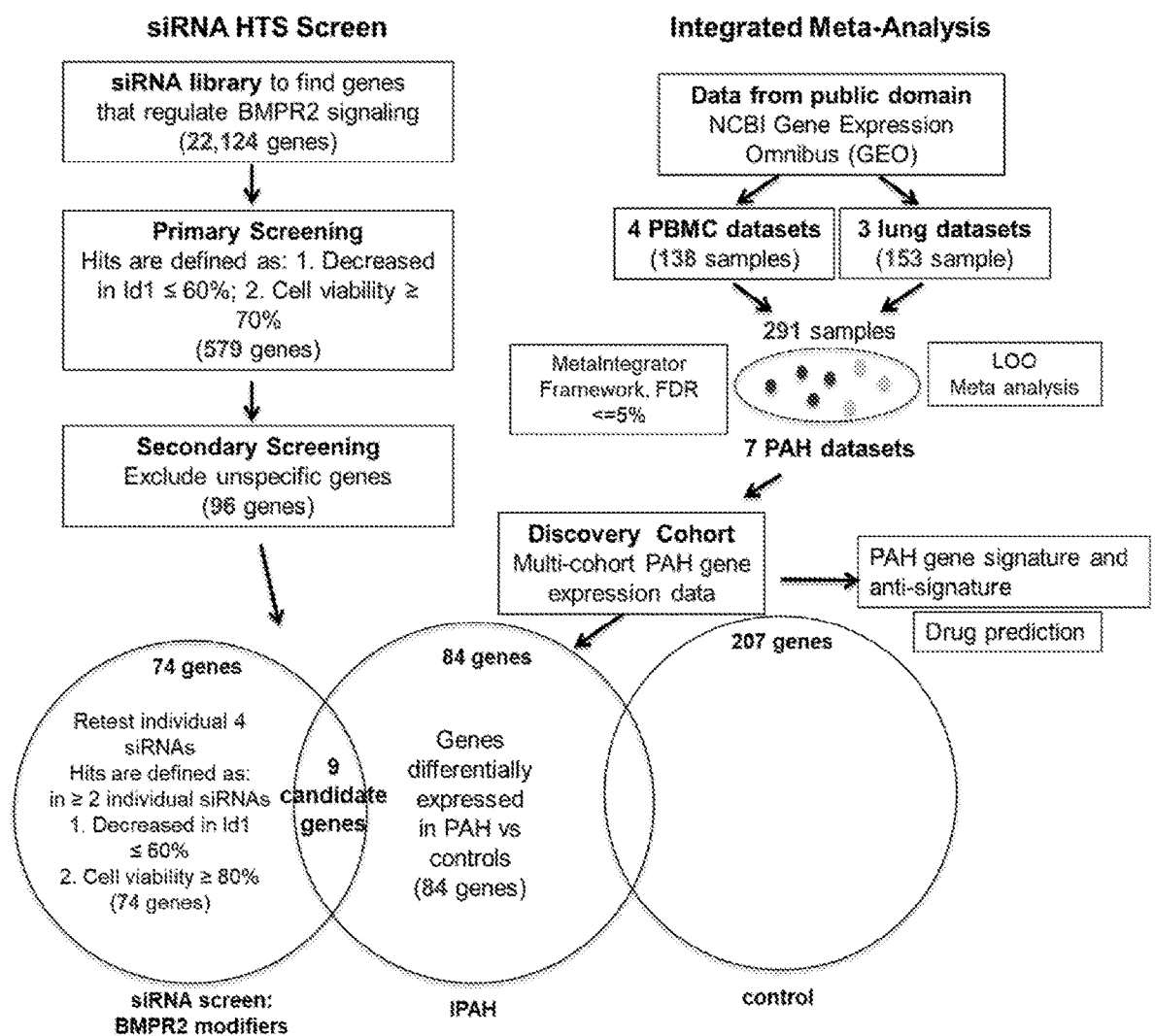
FIGS. 6A-6C: Identification of BMPR2 regulatory genes by siRNA high throughput screen and PAH meta-analysis.
Figure 6B:
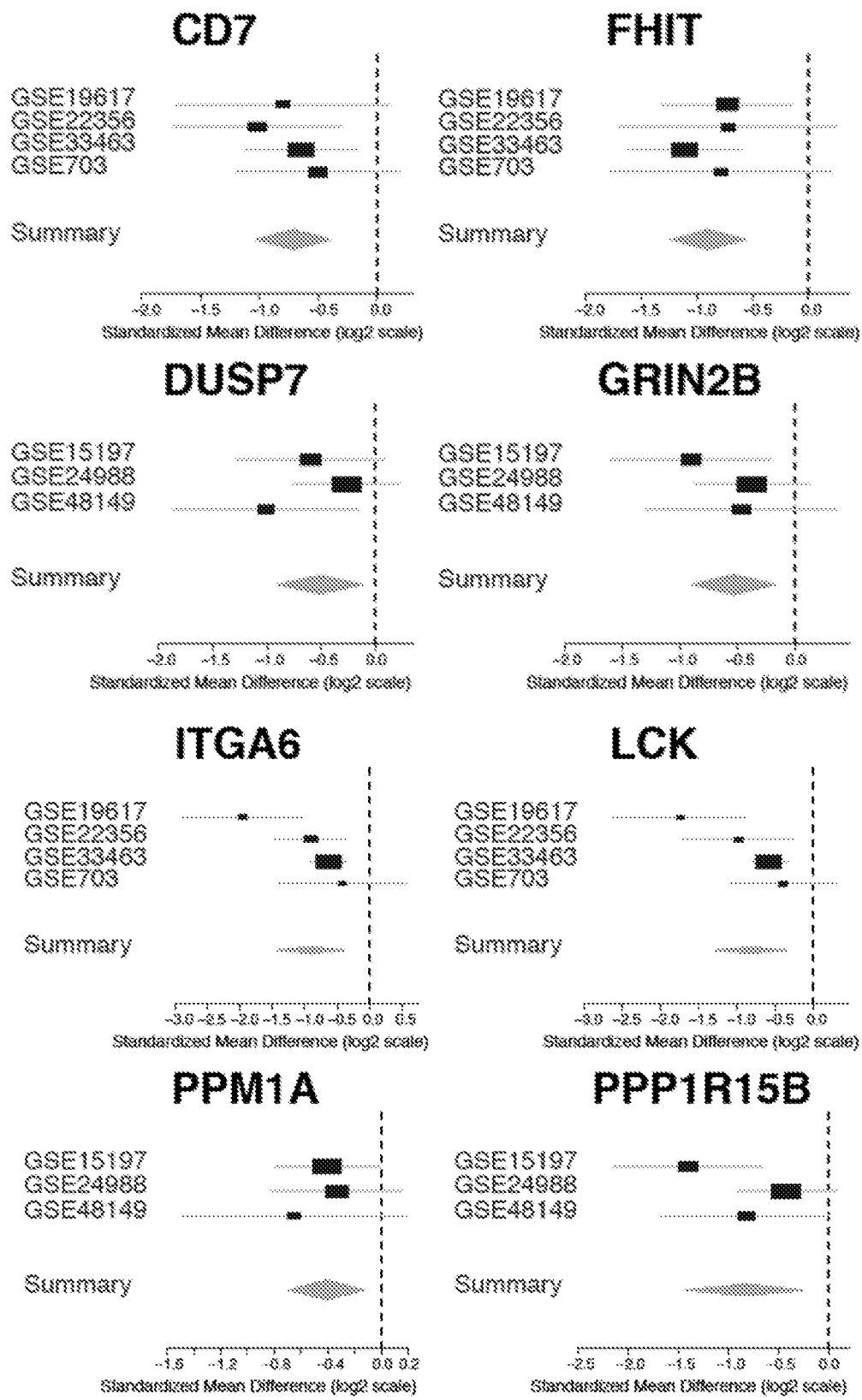
Figure 6C:
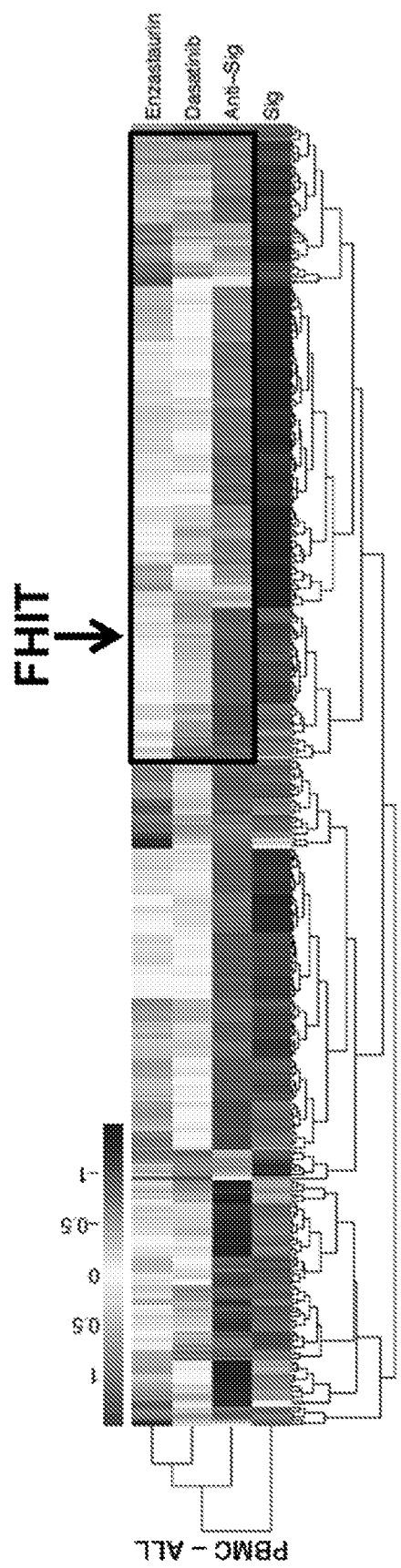

To find 'BMPR2 modifier genes' we conducted an HTS with a murine genome-wide siRNA library (Qiagen) that included 22,124 murine genes (ORFs), with 4 pooled siRNAs for each gene using the BRE-Id1-Luc reporter cell line as previously described(12) as a read-out for BMPR2 signaling. In a two-step screening approach, target gene siRNAs decreased Id1 expression to ≤60%, comparable to siBMPR2, while maintaining a general cell viability of ≥70% with 4 siRNAs or ≥80% with 2 siRNAs respectively, to exclude cell death response genes. This yielded 74 BMPR2-modifier gene candidates that were then compared to multi-cohort, multi-tissue PAH gene expression datasets obtained from the public domain(24-26) to identify a subset of genes that were differentially downregulated in IPAH versus controls (FIG. 6A). We identified 8 candidate genes with decreased expression in IPAH patients and thereby of potential clinical importance in PAH that overlapped with HTS candidate BMPR2-modifier genes: ITGA6, FHIT, LCK, CD7 from the PBMC datasets and PP1R15B, PPM1A, GRIN2B, DUSP7 from the lung datasets (FIG. 6B). The most promising as related to PAH pathogenesis appeared to be FHIT and LCK (Lymphocyte-specific protein tyrosine Kinase). FHIT was most consistently reduced (>50%; $2^{-1}$), arguing for a consistent role in PAH pathology. LCK was strongly connected to PAH pathogenesis, as LCK is known to be inhibited by Dasatinib(27), a reported trigger of drug-induced PAH(28).

We furthermore compared the PAH gene expression signature derived from the public available PAH transcriptomic PBMC datasets, predicted a complimentary anti-PAH signature and compared both with the gene expression profile of two drugs, Dasatinib and Enzastaurin, a drug known to increase FHIT. Both drug both profiles were derived from the LINCS database that profiled a large number of drugs across many cell lines (www.lincscloud.org). In the gene cluster containing FHIT, Enzastaurin-induced gene regulation was similar to the PAH anti-signature (FIG. 6C, Box) whereas Dasatinib-induced gene regulation resembled the PAH signature. This suggests that drugs which mimic the PAH gene expression signature, such as Dasatinib, may be detrimental to PAH, while drugs that reverse the PAH signature, such as Enzastaurin, would be useful for treatment of PAH.

Example VIII. Downregulation of BMPR2 and its Modifier Gene FHIT is Observed in PAH Cells and Lung Tissue and Appears to Modify FPAH Disease Penetrance As FHIT and LCK were identified in the PBMC gene expression dataset, we first investigated whether FHIT was consistently decreased in PAH patient cells, i.e., peripheral blood mononuclear cells (PBMCs), pulmonary artery endothelial cells (PAECs) and transformed lymphocytes, as well as lung tissue.

Figure 7A:
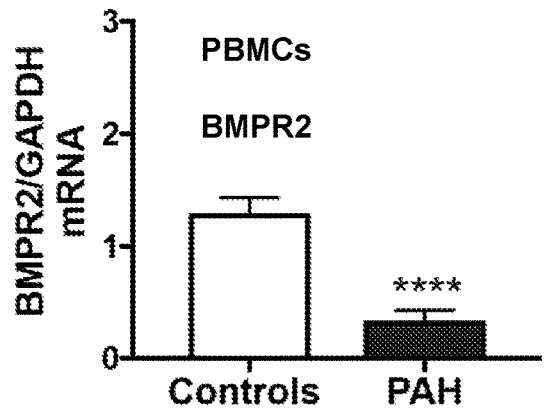
FIGS. 7A-7I: Attenuated FHIT expression in PAH correlates with decreased BMPR2 expression.
Figure 7B:
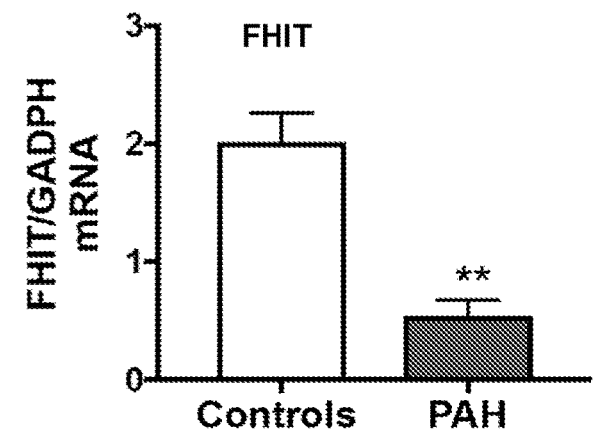
Figure 7C:
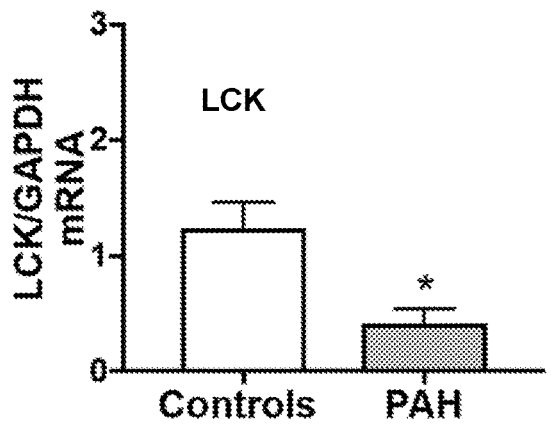
Figure 7D:
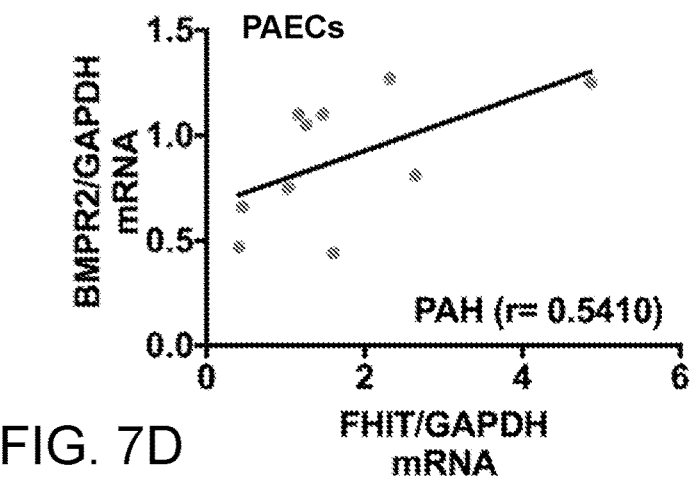
Figure 7E:
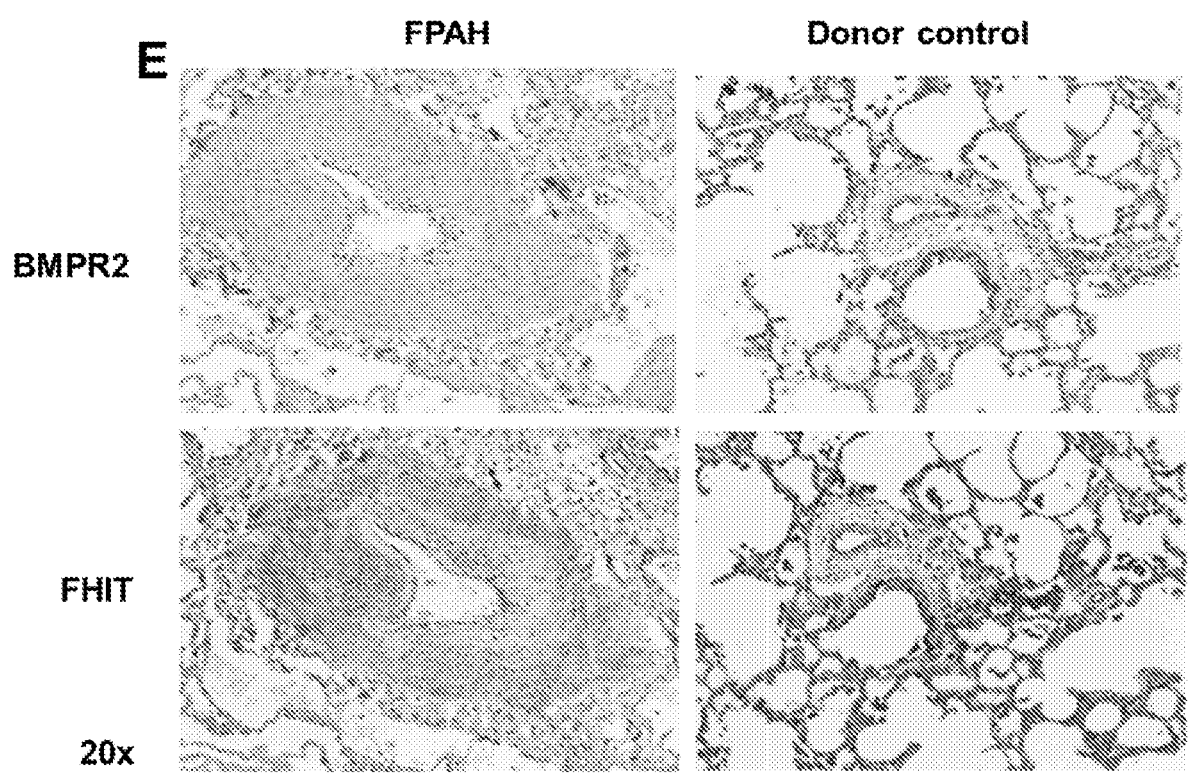
Figure 17A:
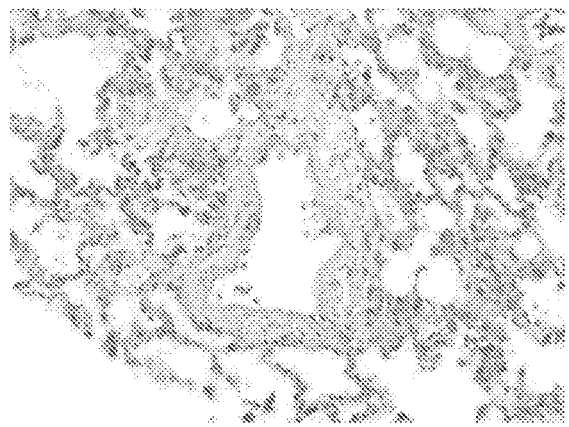
FIGS. 17A-17B: Representative Immunohistochemistry slides from IPAH patient (without a BMPR2 mutation).
Figure 17B:
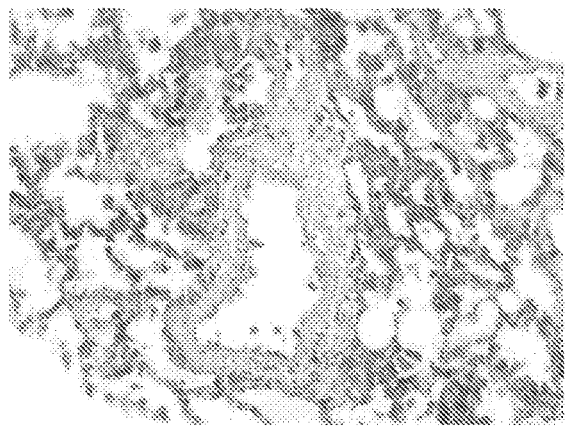

We measured BMPR2, FHIT and LCK expression in PBMCs from 8 PAH patients without BMPR2 mutations, and confirmed that expression of all 3 genes was significantly reduced (FIGS. 7A-C). Microvascular ECs isolated from IPAH patient lungs harvested at the time of lung transplantation(12)(Table 1) showed a positive correlation between FHIT and BMPR2 mRNA expression (FIG. 7D). Immunohistochemistry staining of FHIT and BMPR2 was reduced in FPAH and IPAH patients compared to donor lungs (FIG. 7E, Table 1, FIGS. 17A-17B). While BMPR2 was strongly and uniformly reduced, as expected in the presence of a BMPR2 mutation, the more patchy decrease in FHIT was limited to the neointima and subendothelial layer (FIGS. 18A-18F, 17A-17B), suggesting an incomplete overlap between FHIT and BMPR2 with regards to their gene expression and potential role in vascular remodeling.

We next determined the expression of these genes in FPAH patients with a BMPR2 mutation and healthy obligate BMPR2 carriers to assess whether they may modify disease penetrance in FPAH. A cohort of 7 families with a BMPR2 mutation was selected: 10 patients with a BMPR2 mutation (P1-8), 10 related healthy, obligate BMPR2 mutation carriers (C1-8) and unrelated healthy controls (Table 1). In transformed lymphocytes, extracted as previously described (29), BMPR2 and FHIT mRNA was consistently lower in patients than in healthy carriers (5/7 families), suggesting that FHIT may modify disease penetrance in BMPR2 mutation carriers (FIG. 7F-I, FIG. 19G-H). BMPR2 and FHIT levels were, however, variable amongst the families and different in males and females (FIG. 7H-I, FIG. 19), suggesting that the BMPR2 or FHIT threshold required to suppress PAH pathogenesis varies by genetic background and sex.

Figure 7F:
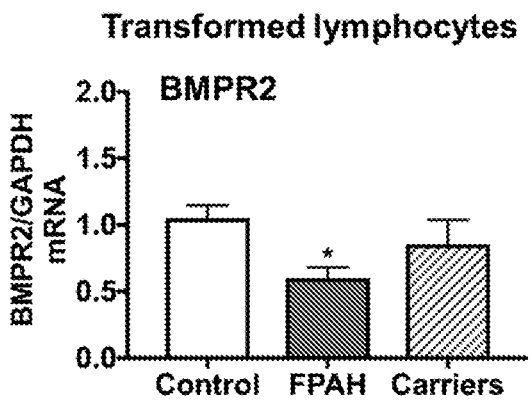
Figure 7G:
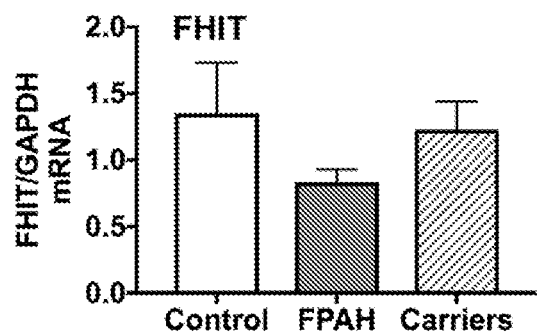
Figure 7H:
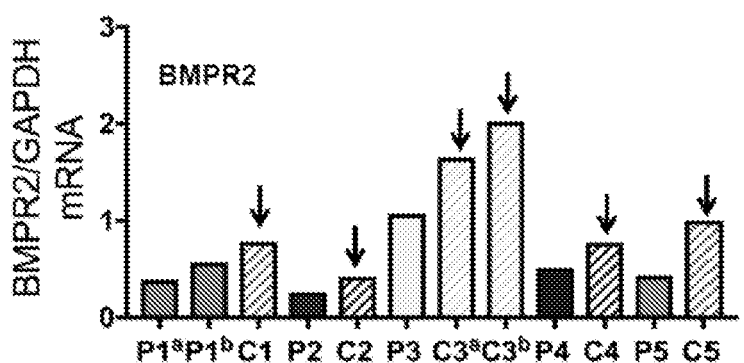
Figure 7I:
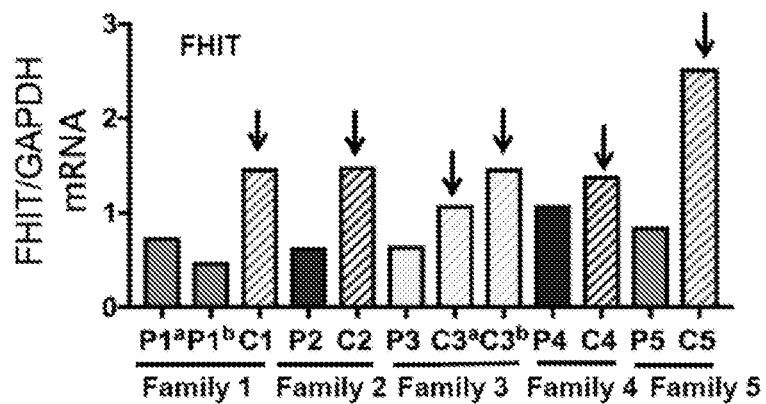
Figure 8A:
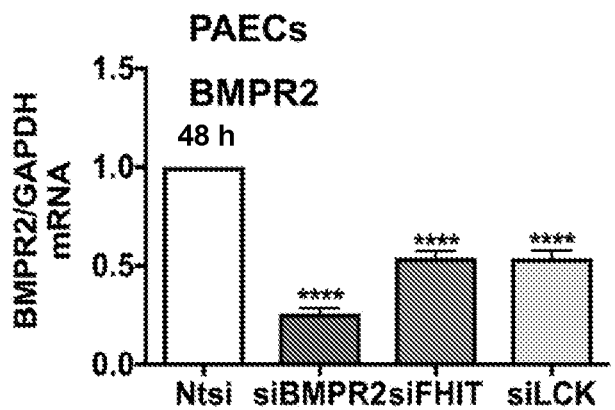
FIGS. 8A-8M: mRNA expression and microRNA profiling in siFHIT PAEC.
Figure 8B:
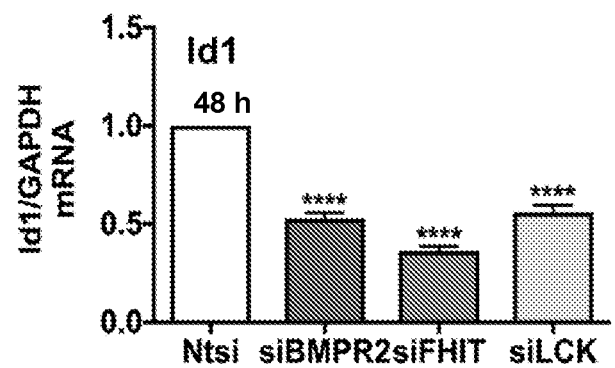
Figure 8C:
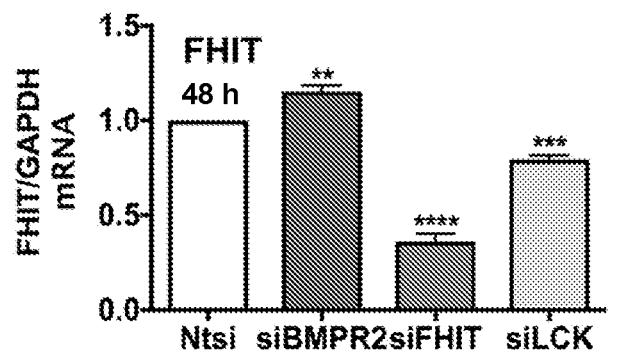
Figure 8D:
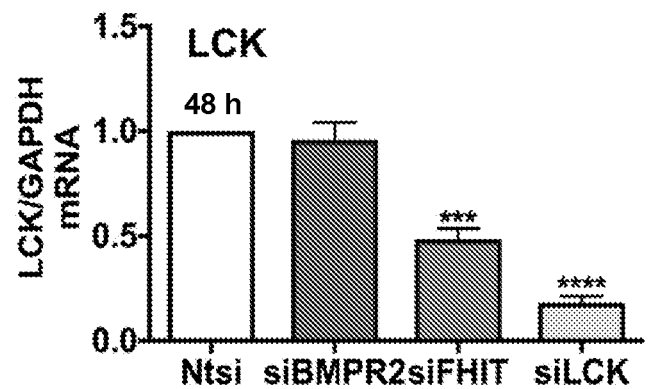

FIGS. 7A-7E show that attenuated FHIT expression in PAH correlated with decreased BMPR2 expression. FIGS. 7A-C depicts qPCR analysis of BMPR2 (FIG. 7A), FHIT (FIG. 7B) and LCK (FIG. 7C) mRNA expression in PBMCs from endstage PAH patients with negative BMPR2 mutation status compared to healthy controls (control n=12, PAH n=8, Mean±SEM, *p<0.05, p<0.01, *p<0.0001 vs. control, Welch's t-test). FIGS. 7A-7E show mRNA expression in PBMCs from endstage PAH patients with negative BMPR2 mutation status compared to healthy controls (control n=12, PAH n=8, Mean±SEM, *p<0.05, p<0.01, *p<0.0001 vs. control, Welch's t-test). FIG. 7D, Correlation and linear regression analysis of BMPR2 and FHIT mRNA expression in IPAH patient PAECs at time of lung transplant (control n=6, IPAH n=6, FPAH n=4, control r=−0.7714, PAH r=0.5410, IPAH r=0.5218, Spearman r, for patient demographics see Table 1B). FIG. 7E, Representative pulmonary anti-BMPR2 and anti-FHIT IHC (HRP—brown staining) in PAH patient and donor control lung tissue at time of transplant (n=3, for patient demographics see Table 1C). FIGS. 7F-7G, qPCR analysis of FHIT and BMPR2 expression in transformed lymphocytes from FPAH patients, non-affected BMPR2 mutation carriers and healthy controls (n=10, Mean±SEM, *p<0.05, One-Way ANOVA, Dunnett's post-test, for patient demographics see Table 1A). FIGS. 7H-7I, qPCR analysis of FHIT and BMPR2 expression in transformed lymphocytes from selected families (n=5, P=FPAH patients, C=healthy mutation carrier, the arrows point towards the carriers with consistently increased FHIT and BMPR2 compared to their FPAH family members, for patient demographics see Table 1A).

affect FHIT and LCK expression in PAEC confirming that BMPR2 is downstream of FHIT and LCK (FIG. 8C, FIG. 8D). Of interest, siFHIT decreased LCK expression to 50%, suggesting a potential interdependence of both modifier genes (FIG. 8D).

Figure 8E:
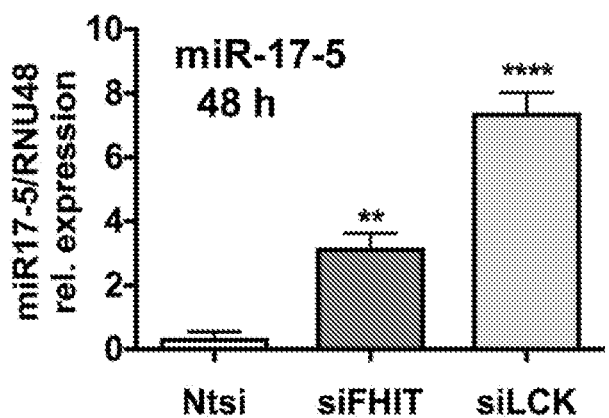
Figure 8F:
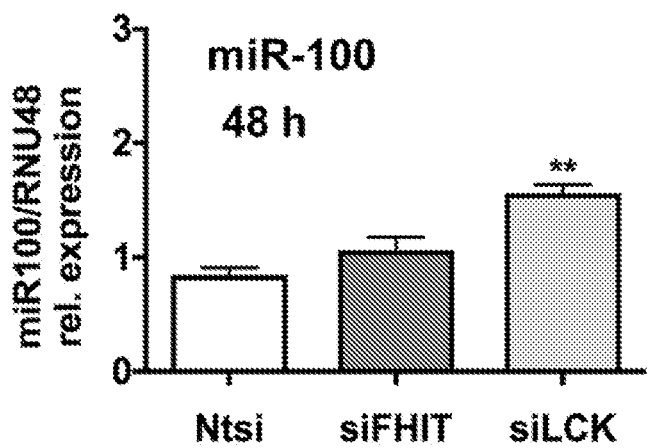
Figure 8G:
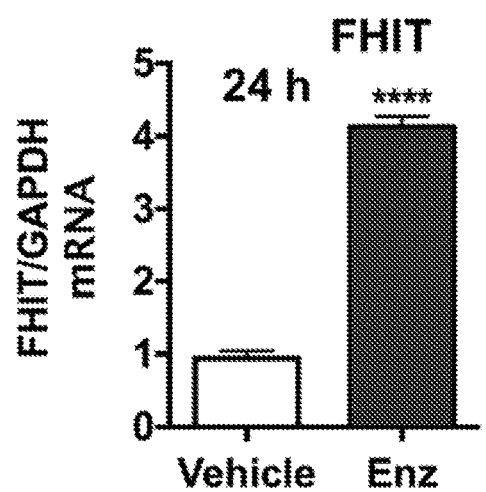
Figure 8H:
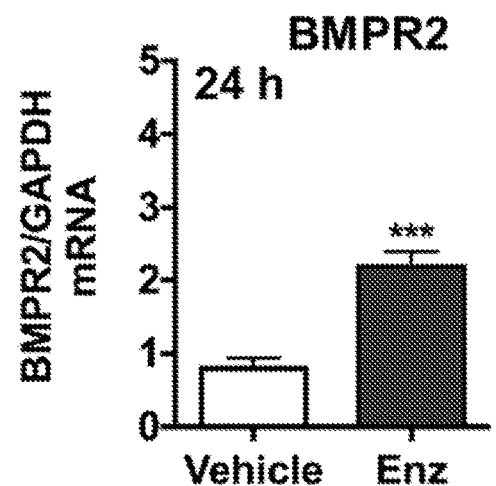
Figure 8I:
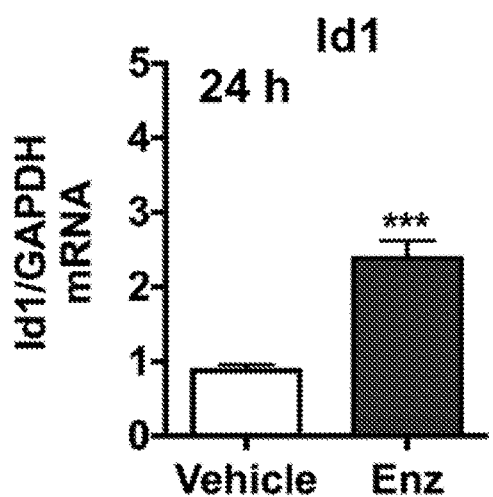
Figure 8J:
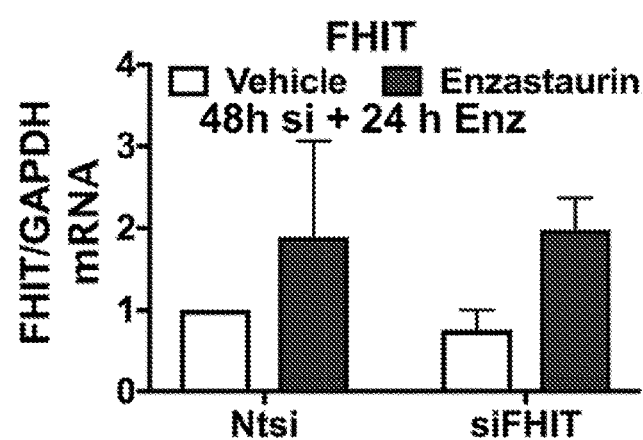
Figure 8K:
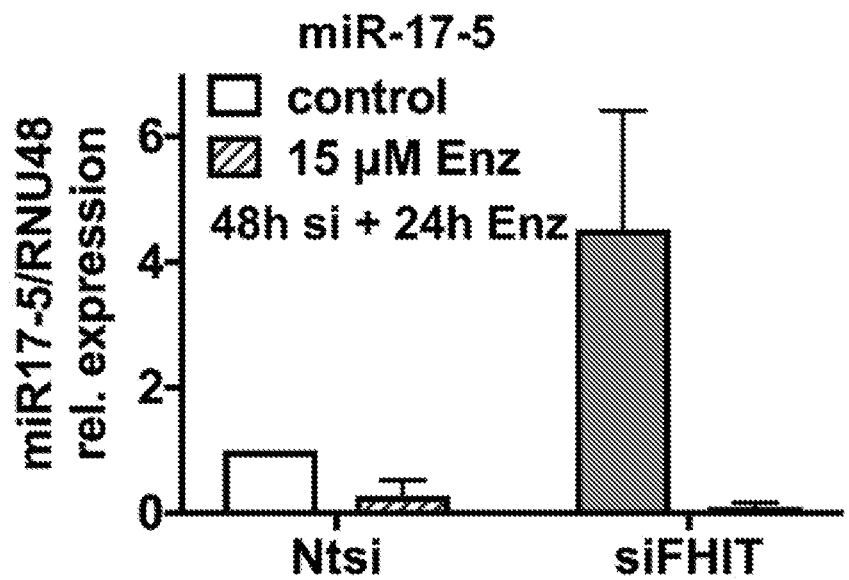
Figure 8L:
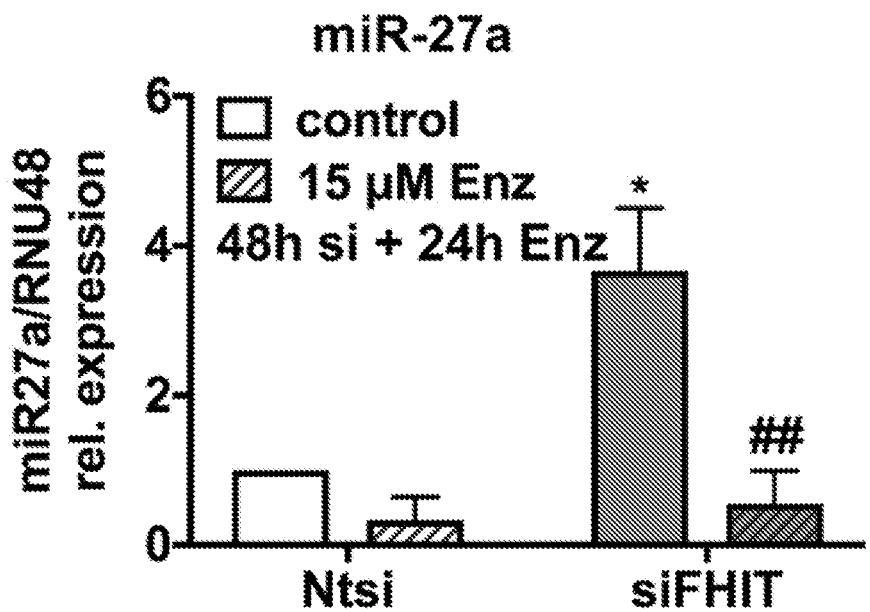

Results of this study are shown in FIGS. 8A-8M, in which mRNA expression and microRNA profiling in siFHIT PAEC reveals a potential role for microRNAs miR17-5 and miR27a in the regulation of BMPR2 signalling by FHIT that can be engaged by Enzastaurin. FIGS. 8A-8D, Relative mRNA expression of BMPR2 (FIG. 8A), Id1 (FIG. 8B), FHIT (FIG. 8C) and LCK (FIG. 8D) normalised to GAPDH in PAECs transfected with an siBMPR2, siFHIT, siLCK or non-targeting control (Ntsi) pool of 4 siRNAs (qPCR, Amaxa nucleofection, t=48h, n=3, Mean±SEM, p<0.01, *p<0.001, **p<0.0001 vs. control, One Way ANOVA, Turkey's post-test). FIGS. 8E-8F, Relative miR expression of miR17-5 (FIG. 8E) and miR100 (FIG. 8F) normalised to RNU48 in PAECs transfected with an siFHIT, siLCK or non-targeting control (Ntsi) pool of 4 siRNAs (qPCR, t=48h post-transfection, n=3, Mean±SEM, p<0.01, **p<0.0001 vs. Ntsi control, One Way ANOVA, Dunnett's post-test). FIGS. 8G-8I, Relative mRNA expression of FHIT (FIG. 8G), BMPR2 (FIG. 8H) and Id1 (FIG. 8I) normalised to GAPDH in PAECs incubated with 15 μM Enzastaurin for 24 hours (qPCR, t=72h post-transfection, n=3, Mean±SEM, *p<0.001, ****p<0.0001 vs. vehicle, unpaired t-test). FIG. 8J, Relative mRNA expression of FHIT normalised to GAPDH in PAECs transfected with an siFHIT or non-targeting control (Ntsi) pool of 4 siRNAs, treated with or without 15 μM Enzastaurin for 24 hours (qPCR, t=72h post-transfection, RNAimax, n=4, Mean±SEM). FIG. 8K-8L, Relative miR expression of miR17-5 (K) and miR27a (FIG. 8L) normalised to RNU48

TABLE 1A

| | Patient ID | Sex | Age at time of study | Age at discovery | Survival since discovery | % disease free years | BMPR2 NMD Status | Relation |
|---|---|---|---|---|---|---|---|---|
| Family1 | P1a | M | 53 | 43 | 10 | 81 | NMD+ | |
| | P1b | F | 39 | 25 | 14 | 64 | NMD+ | 2nd cousin of P1a |
| | C1 | F | 74 | | | 100 | NMD+ | distant cousin of P1a and P1b |
| | C1b | M | 81 | | | 100 | NMD+ | Father of P1a |
| Family2 | P2 | F | 43 | 35 | 8 | 81 | unlikely, not confirmed | |
| | C2 | F | 72 | | | 100 | unlikely, not confirmed | mother of P2 |
| Family3 | P3 | F | 39 | 28 | 11 | 72 | NMD− | |
| | C3a | M | 39 | | | 100 | NMD− | Distant cousin of P3 |
| | C3b | F | 50 | | | 100 | NMD− | aunt of P3 |
| Family4 | P4 | M | 50 | 38 | 12 | 76 | NMD+ | |
| | C4 | F | 56 | | | 100 | NMD+ | distant cousin of P4 |
| Family5 | P5 | M | 49 | 34 | 15 | 69 | unlikely, not confirmed | |
| | C5 | M | 63 | | | 100 | unlikely, not confirmed | uncle of P5 |
| Family6 | P6a | F | 65 | 28 | 37 | 43 | NMD+ | niece of P6b |
| | P6b | F | 82 | 64 | 18 | 78 | NMD+ | |
| | C6 | M | 85 | | | 100 | NMD+ | brother of 6b, uncle of P6a |
| Family7 | P7 | F | 48 | 37 | 11 | 77 | NMD+ | |
| | C7 | M | 71 | | | 100 | NMD+ | uncle of P7 |
| unrelated | P8 | F | 34 | 29 | 5 | 34 | NMD− | |
| | C8 | F | 67 | | | 100 | NMD− | |
| Controls | | F n = 7 M n = 3 | | | | | | |

TABLE 1B

| Group | Diagnosis | Sex | Age at time of study | Racial background |
|---|---|---|---|---|
| Controls | | F n = 3 M n = 3 | 38.7 ± 8.1554 | Caucasian n = 5 Unknown n = 1 |
| Patients | IPAH n = 7 FPAH n = 2 N/K n = 1 | F n = 7 M n = 3 | 35.1 ± 2.8889 | Caucasian n = 8 African American n = 1 Hispanic n = 1 |

TABLE 1C

| Patient ID | Diagnosis | Sex | Age | Racial Background |
|---|---|---|---|---|
| CC-015 | FPAH | F | 33 | Caucasian |

Figure 8M:
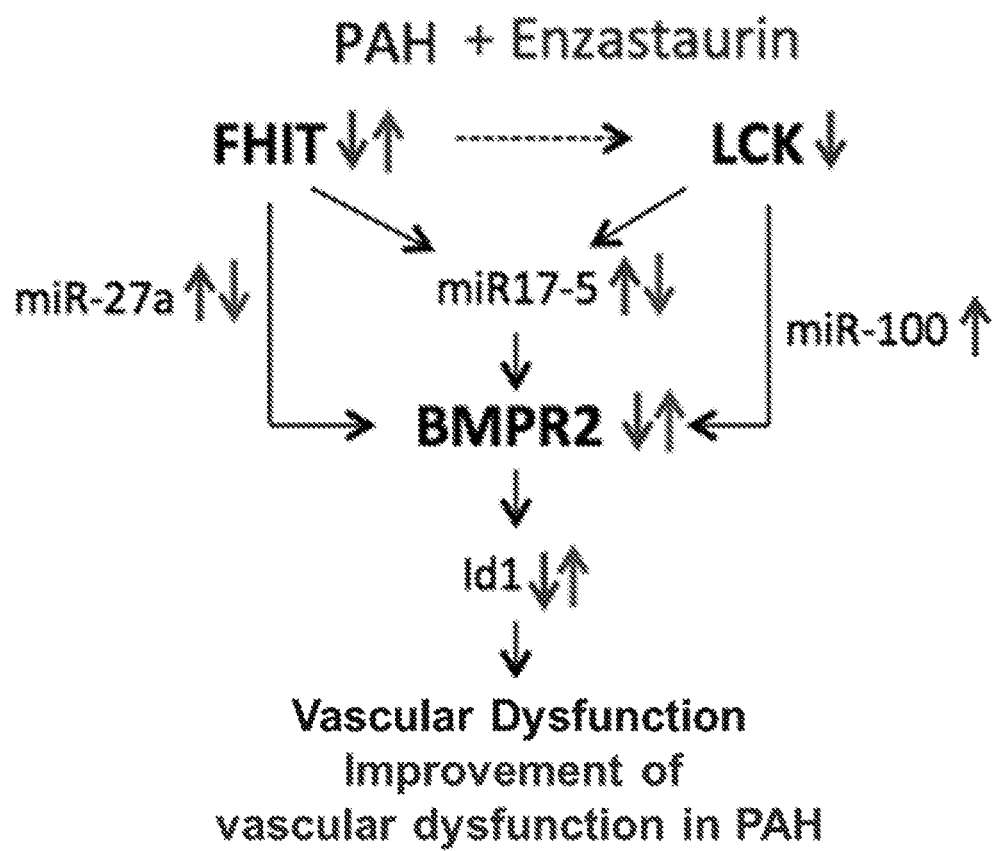

Example IX. miR17-5 and miR27-a Negatively Regulate FHIT/BMPR2 Signaling, Restored by Enzastaurin We next identified that FHIT and LCK are upstream regulators of BMPR2. Knocking down FHIT and LCK in PAEC with siRNA decreased both, the BMPR2 expression as well as its downstream signaling, measured by the target ID1 (FIG. 8A, FIG. 8B). Conversely, siBMPR2 did not in PAECs treated for 24 hours with or without 15 µM Enzastaurin transfected with an siFHIT or non-targeting control (Ntsi) pool of 4 siRNAs (qPCR, t=72h post-transfection, n=3, Mean±SEM, p<0.01, **p<0.0001 vs. Ntsi control, Two Way ANOVA, Dunnett's post-test). FIG. 8M, Schematic model of the proposed regulation of BMPR2 by FHIT.

How FHIT and LCK levels regulate BMPR2 expression is unknown. As miRNAs have been shown to play a major role in the regulation of BMPR2 signaling in PAH(30, 31), we investigated whether selected microRNAs would orchestrate FHIT and LCK mediated regulation of BMPR2 expression in PAECs. We focused on miR17-5 and miR100, both direct regulators of BMPR2, and miR27a, a readout for canonical Smad signaling(30, 32). Reductions of FHIT mRNA by siRNA increased the expression of miR17-5 (3-4 fold; FIG. 8E, FIG. 8K) and miR27-a (4-fold; FIG. 8L), but not miR100 expression (FIG. 8G). LCK deficiency strongly increased both miR17-5 and miR100 expression by 8-fold or 2-fold respectively (FIGS. 8E, 8F).

Treatment with Enzastaurin for 24 hours (15 M) increased FHIT, BMPR2 and Id1 expression in PAECs (FIGS. 8G-I, FIGS. 20A-20C). Interestingly, Enzastaurin (15 M) was able to rescue FHIT mRNA knockdown (treatment for 24 h after knock-down, FIG. 8J), supporting the previous finding that Enzastaurin potently up-regulates FHIT expression. Furthermore, Enzastaurin inhibited siFHIT-mediated increases in miR17-5 and miR27a (FIGS. 8K, 8L), providing some mechanistic insight into how FHIT and Enzastaurin might regulate BMPR2 levels by modulating miRNA expression (FIG. 8M). We furthermore showed that reducing miR17-5 using anti-miR transfection in addition to siFHIT, increased BMPR2 and ID1 expression, suggesting that FHIT mediated BMPR2 modulation is in part miR17-5 dependent. (FIGS. 21A-21D).

Example X. Enzastaurin Up-Regulates FHIT/BMPR2 Signaling and Prevents Vascular Dysfunction Induced by FHIT-Deficiency In Vitro Given that PAH is characterized by loss of pulmonary vessels (33), we investigated how FHIT expression relates to inhibition of vessel formation, increased apoptosis, DNA damage(34, 35) and cell proliferation in PAEC. We therefore assessed whether decreasing FHIT and BMPR2 expression in PAEC worsened EC dysfunction and whether treatment with Enzastaurin for 24 hours could rescue the phenotype.

Figure 9A:
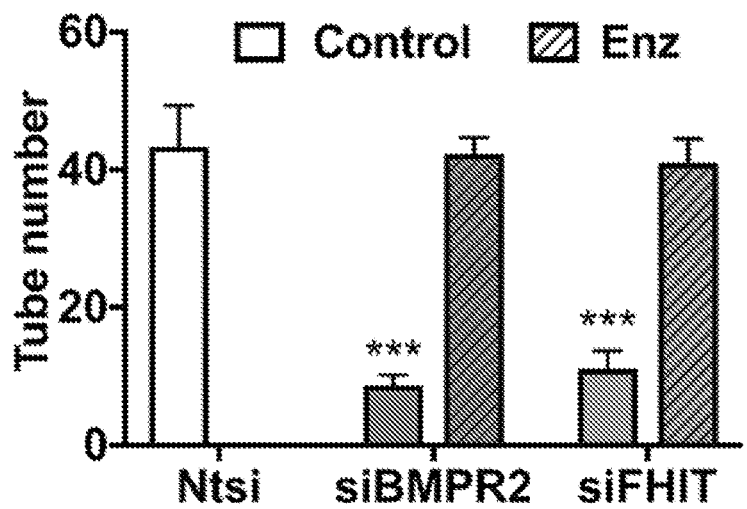
FIGS. 9A-9J: Enzastaurin increases expression of the BMPR2 upstream signalling molecule FHIT in PAECs and reverses PAH-specific functional deficits in tube formation, apoptosis, DNA damage and proliferation in FHIT deficient PAEC.
Figure 9B:
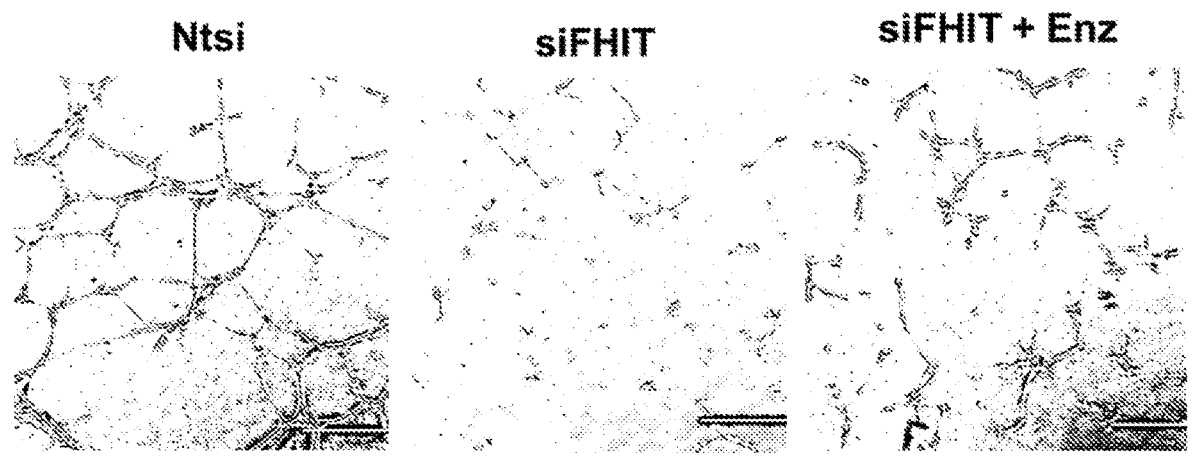
Figure 9C:
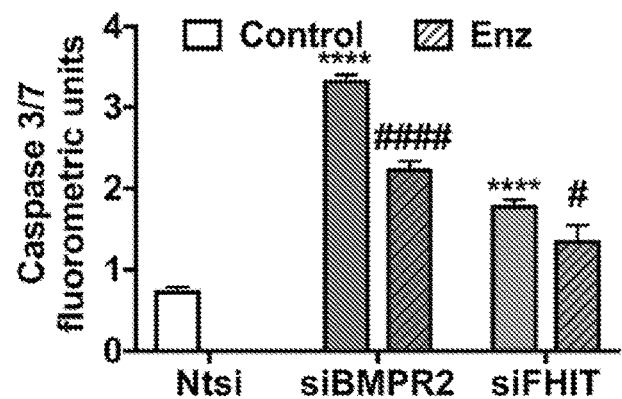
Figure 9D:
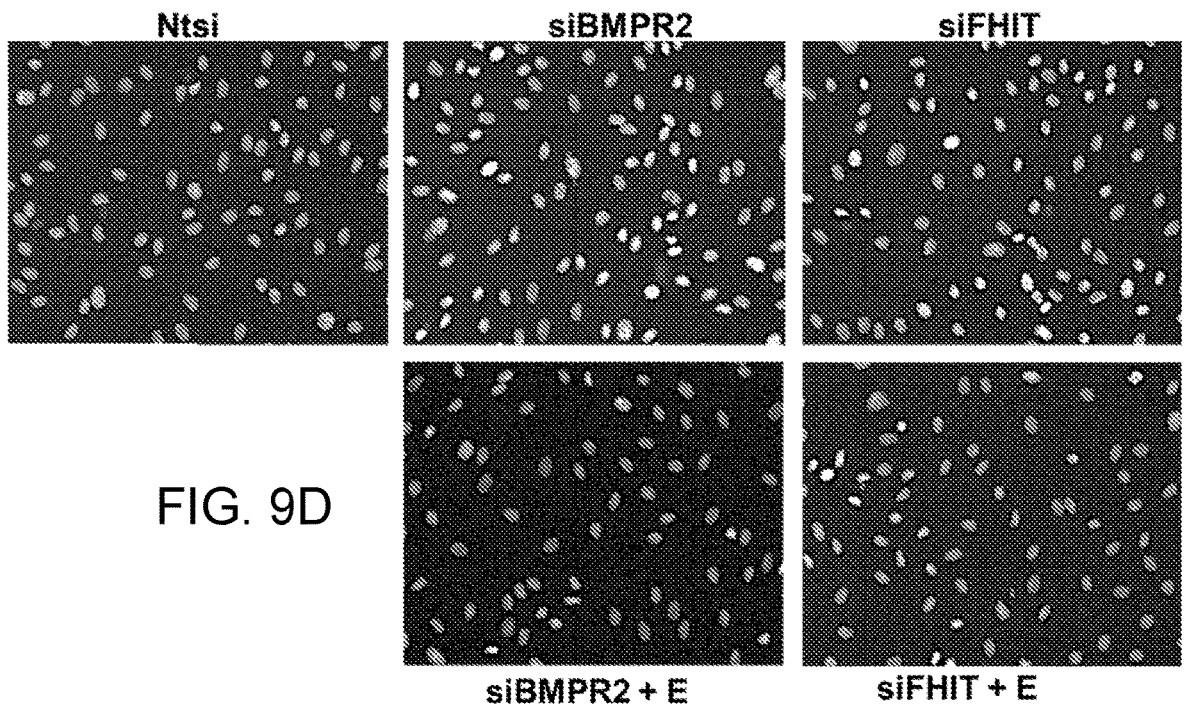
Figure 9E:
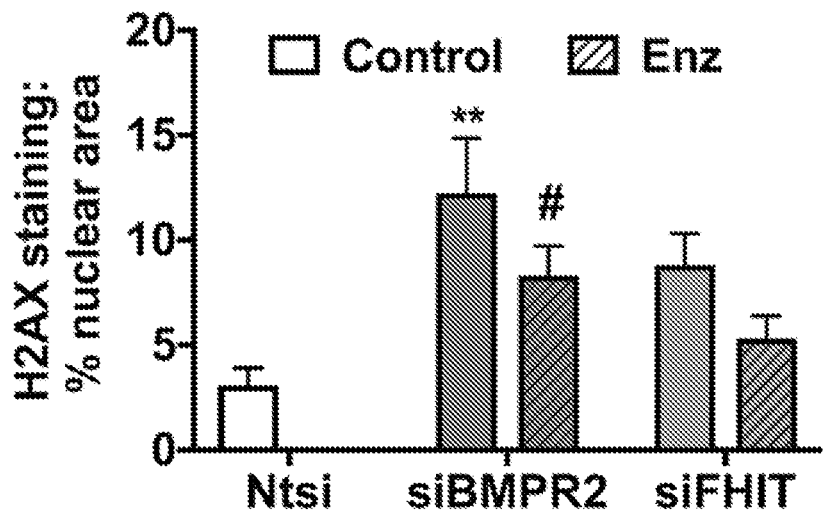
Figure 9F:
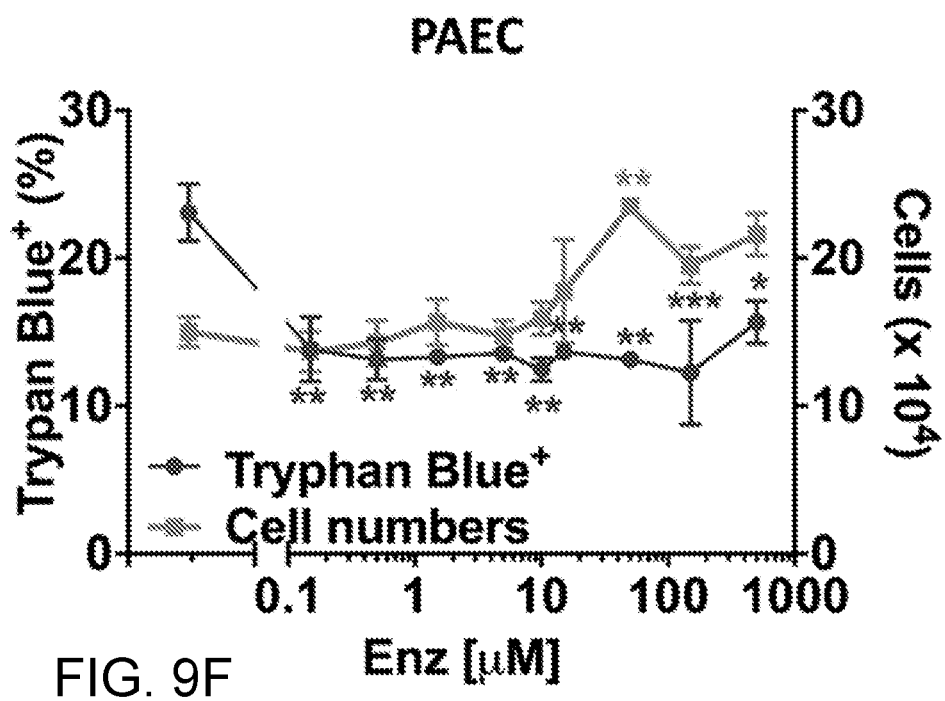
Figure 9G:
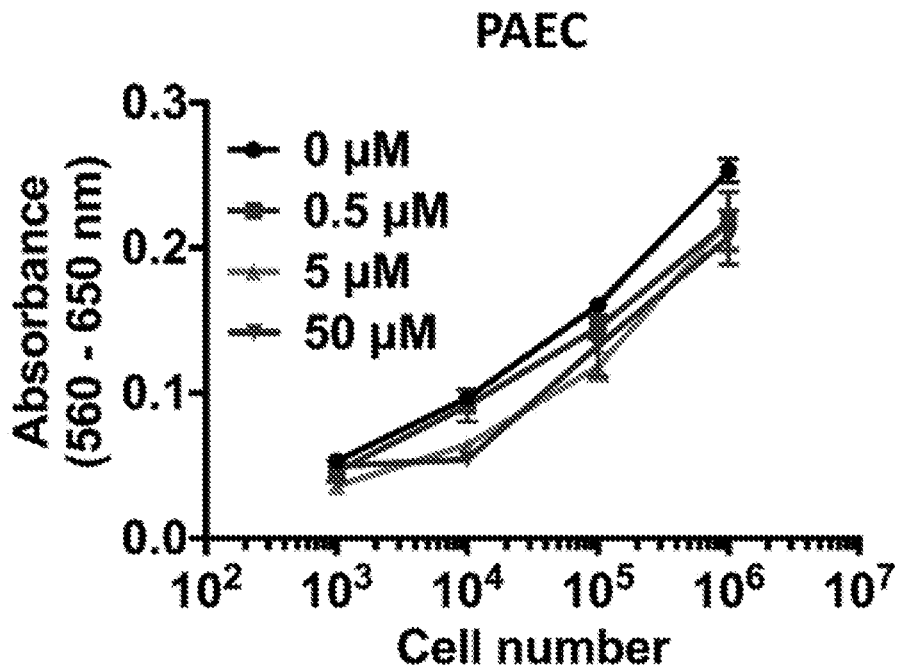
Figure 9H:
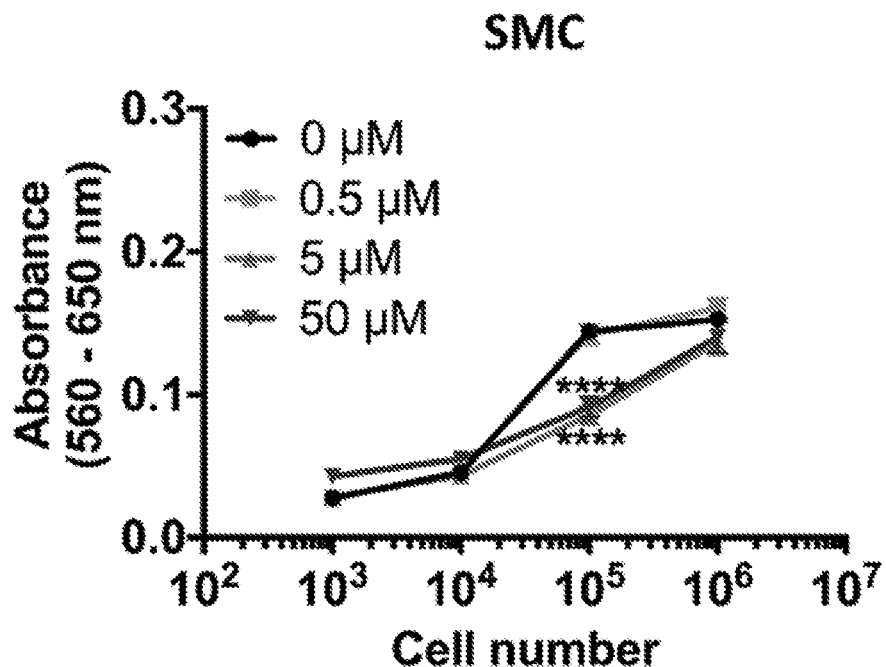
Figure 9I:
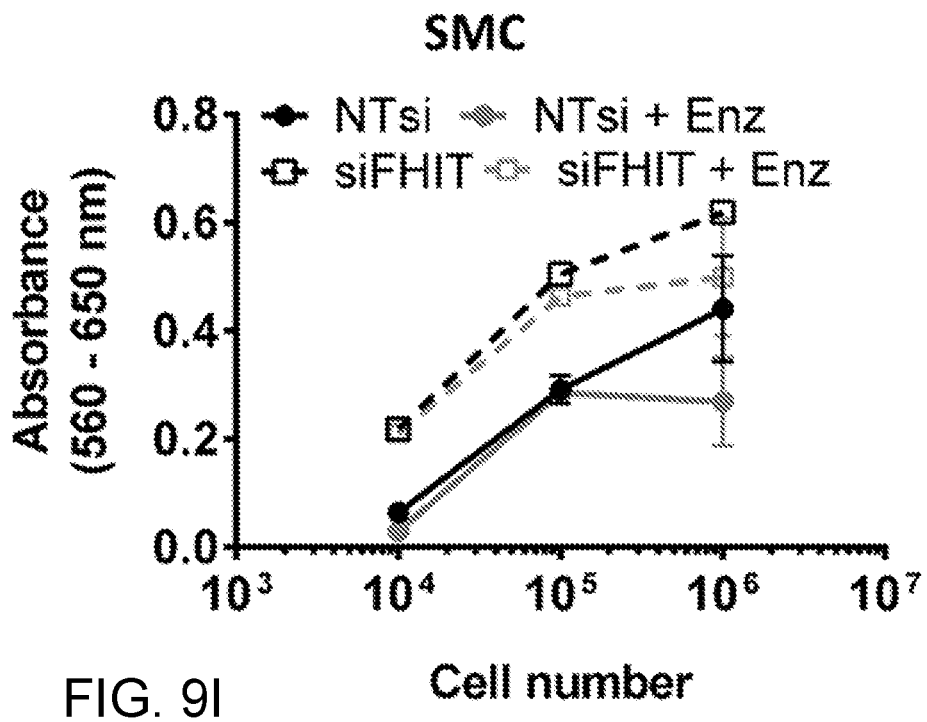
Figure 9J:
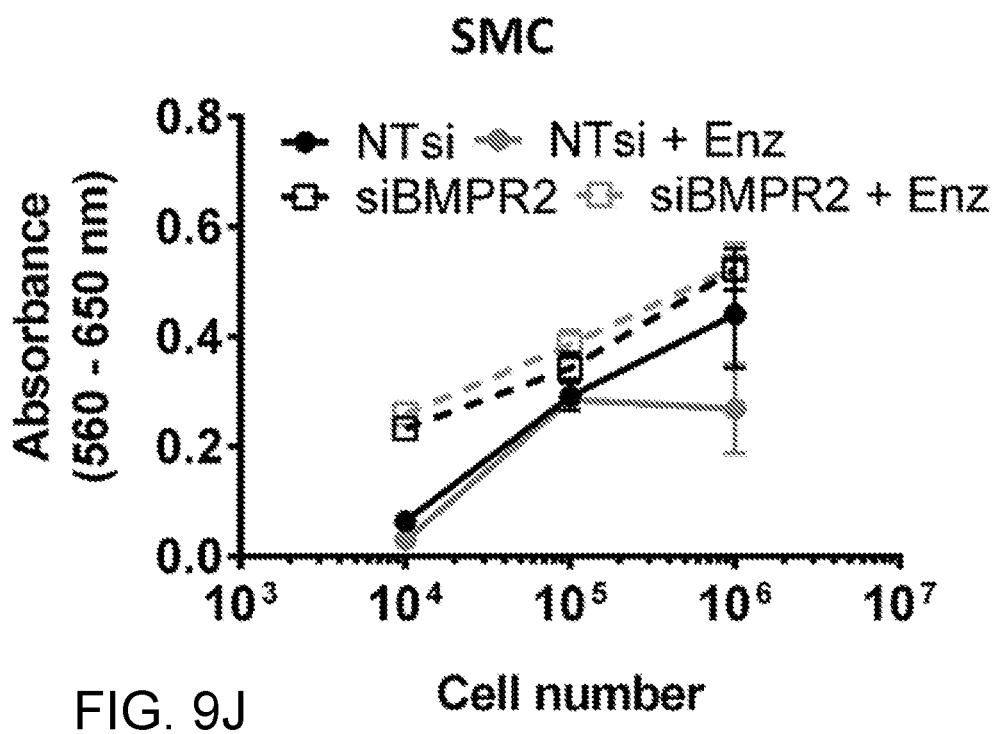

Results of this study are shown in FIGS. 9A-9J, which show that Enzastaurin increases expression of the BMPR2 upstream signalling molecule FHIT in PAECs and reverses PAH-specific functional deficits in tube formation, apoptosis, DNA damage and proliferation in FHIT deficient PAEC. FIGS. 9A-9B, Matrigel tube formation assay in siFHIT PAEC rescued by 15 µM Enzastaurin for 24 hours (t=48h post-transfection, Amaxa nucleofection, Ntsi 43.3±5.9, siBMPR2 8.7±1.5, siFHIT 11.0±2.6 tubes/average of 5 fields (20×), n=3, Mean±SEM, *p<0.001 vs. Ntsi, One-Way ANOVA, Dunnett's post-test, bars denote 1 mm). FIG. 9C, Caspase 3/7 luminescence in siBMPR2 and siFHIT PAEC rescued by 15 µM Enzastaurin (t=48 h post-transfection, RNAimax, Caspase-Glo® 3/7 Assay, n=3, Mean±SEM, p<0.0001 vs. Ntsi, #p<0.05, ####p<0.0001 vs. untreated control, One-Way ANOVA, Dunnett's post-test). FIGS. 9D-E, γH2AX staining in siBMPR2 and siFHIT PAEC rescued by 10 µM Enzastaurin for 24 hours (t=72h post-transfection, Dharmafect, n=3, Mean±SEM, p<0.01 vs. Ntsi, #p<0.05 vs. untreated control, One-Way ANOVA, Dunnett's post-test). Quantified area=% of cells that show nuclear γH2AX staining quantified with automated software (white nuclei=positive stain, grey nuclei=background stain). FIG. 9F, Total cell counts and % Trypan Blue+PAEC cultured in varying concentrations of Enzastaurin (n=3, One Way ANOVA, *p<0.05, **p<0.01 vs. untreated control). FIGS. 9G-9H, MTT proliferation assay in Enzastaurin-treated (0.5-50 M) in PASMC and PAEC, respectively. (n=3). FIGS. 9I-9J, MTT proliferation assay in Enzastaurin-treated (5 M) siFHIT and siBMPR2 transfected PASMC compared to Ntsi control, respectively. (n=3).

Loss of FHIT and BMPR2 impaired PAECs tube formation 6 hours after cells were seeded in a Matrigel tube formation assay(12) compared to cells treated with control Ntsi (FIG. 9A, FIG. 9B). Enzastaurin treatment fully reversed the defects in tube formation in FHIT- and BMPR2-deficient PAECs after 24 hours, in accordance with its ability to increase FHIT expression at this time point (FIG. 9J).

As a cumulative viability measurement, we quantified caspase3/7 activity, using the luminescent Caspase-Glo®3/7 assay(36) and DNA damage, using histone H2AX phosphorylation by immunofluorescence and quantification as nuclear area staining (%) by confocal microscopy(34, 35, 37). Reducing FHIT and BMPR2 mRNA activated caspases in PAECs 48 hours post-transfection (FIG. 9C), while Enzastaurin decreased siBMPR2 and siFHIT-induced PAEC apoptosis. Reducing FHIT levels increased DNA damage after 48 hours about 4-fold to Ntsi controls (FIGS. 9D, 9E), comparable to the degree of DNA damage observed in previous PBMC studies for PAH patients(35). DNA damage induced by FHIT or BMPR2-loss was significantly attenuated by Enzastaurin in PAECs. PAEC proliferation was assessed via an MTT proliferation assay and hemocytometer cell counts(36). Enzastaurin did not elicit cell toxicity by Trypan Blue viability assay. We rather observed increased cell numbers following treatment with Enzastaurin (up to 50 µM), likely reflecting decreased apoptosis, as no increase in PAEC proliferation was detected (FIGS. 9F,9G).

Given the role of SMCs in medial hypertrophy and vascular remodelling in PAH, we determined that reductions in FHIT (FIG. 9H,I), but not BMPR2 (FIG. 9J), increased PASMC proliferation in vitro (FIG. 9I) that was rescued by Enzastaurin. We conclude from these data that FHIT loss promotes PAEC and PASMC dysfunction, which can be improved by Enzastaurin in a FHIT and BMPR2-dependent manner. The stronger beneficial effect of Enzastaurin on PAEC—compared to PASMC-function might be explained by the stronger expression of BMPR2 in PAECs, which might make them more responsive to BMPR2 modulating therapies.

Figure 10A:
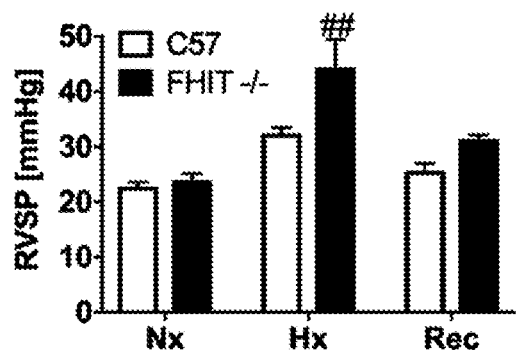
FIGS. 10A-10I: Fhit−/− C57BL/6 mice develop experimental PH after chronic exposure to Hypoxia.
Figure 10B:
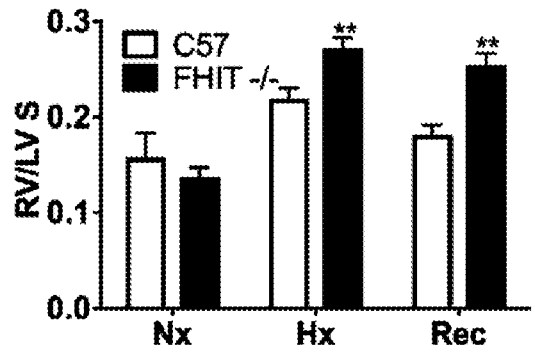
Figure 10C:
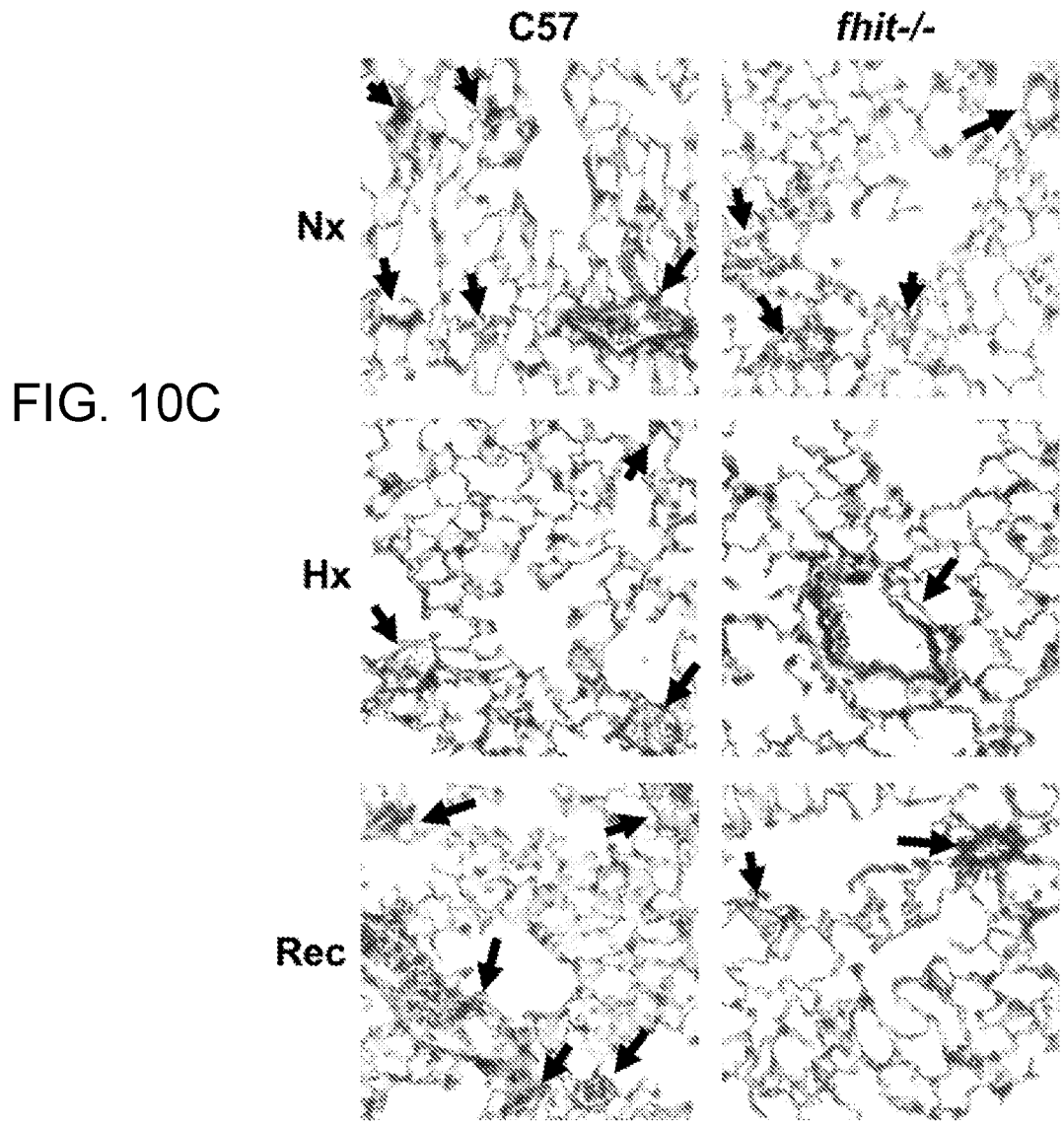
Figure 10D:
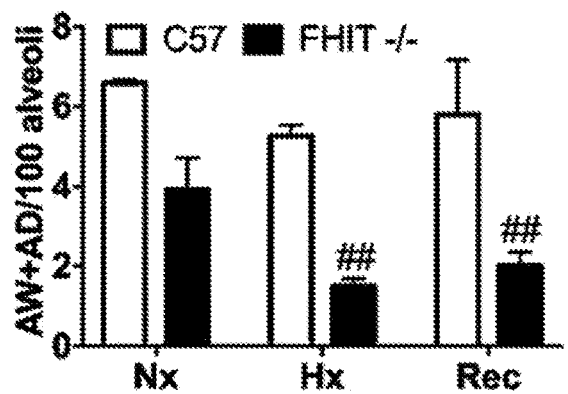
Figure 10E:
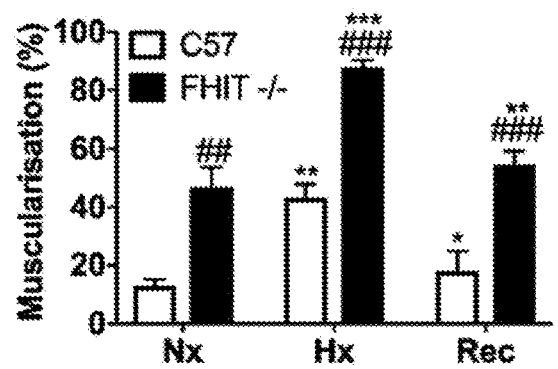
Figure 10F:
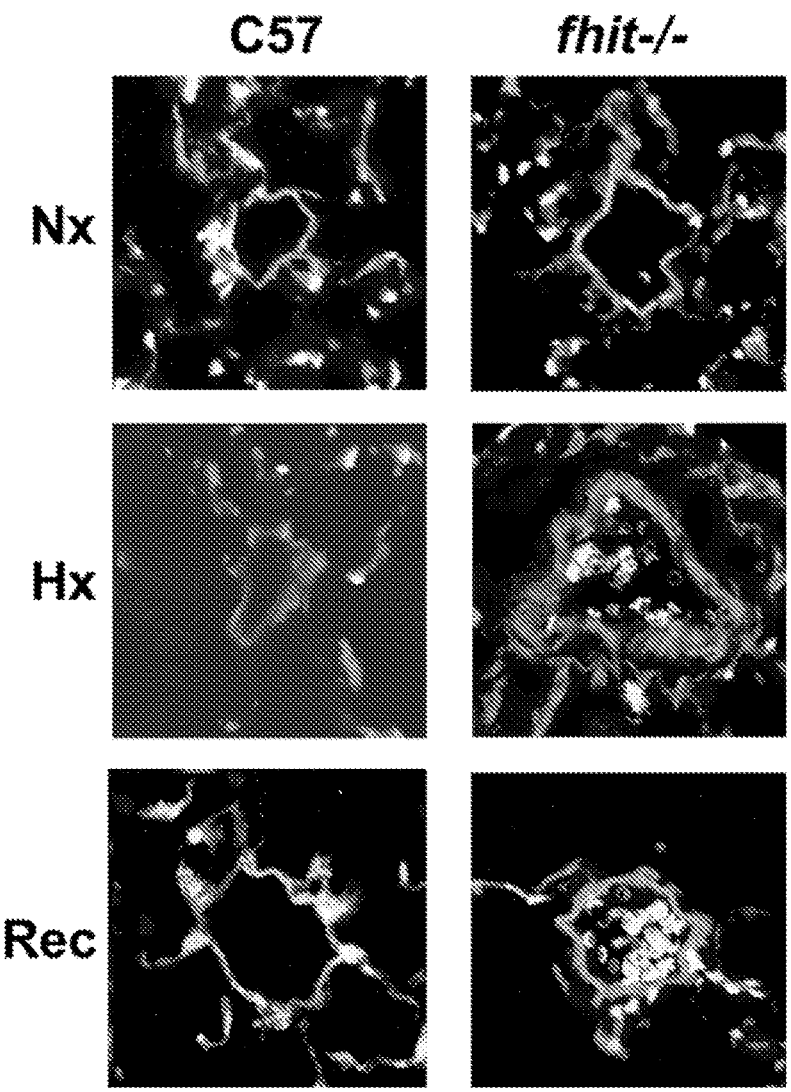
Figure 10G:
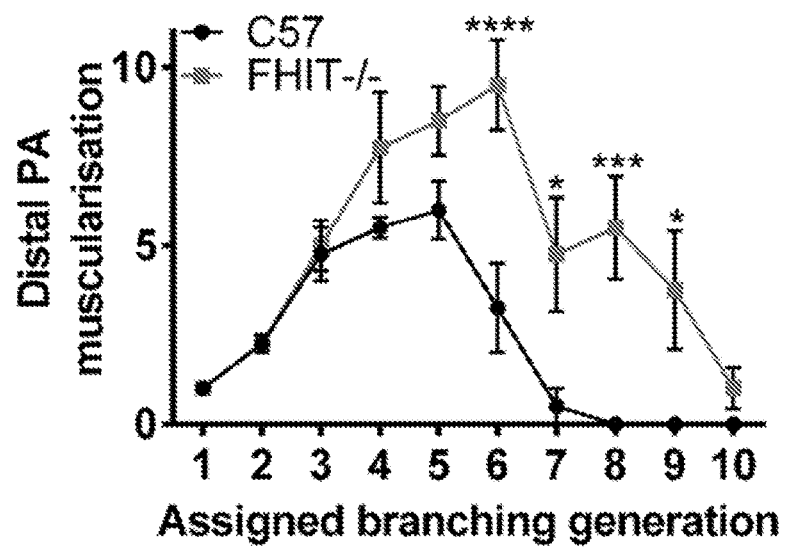
Figure 10H:
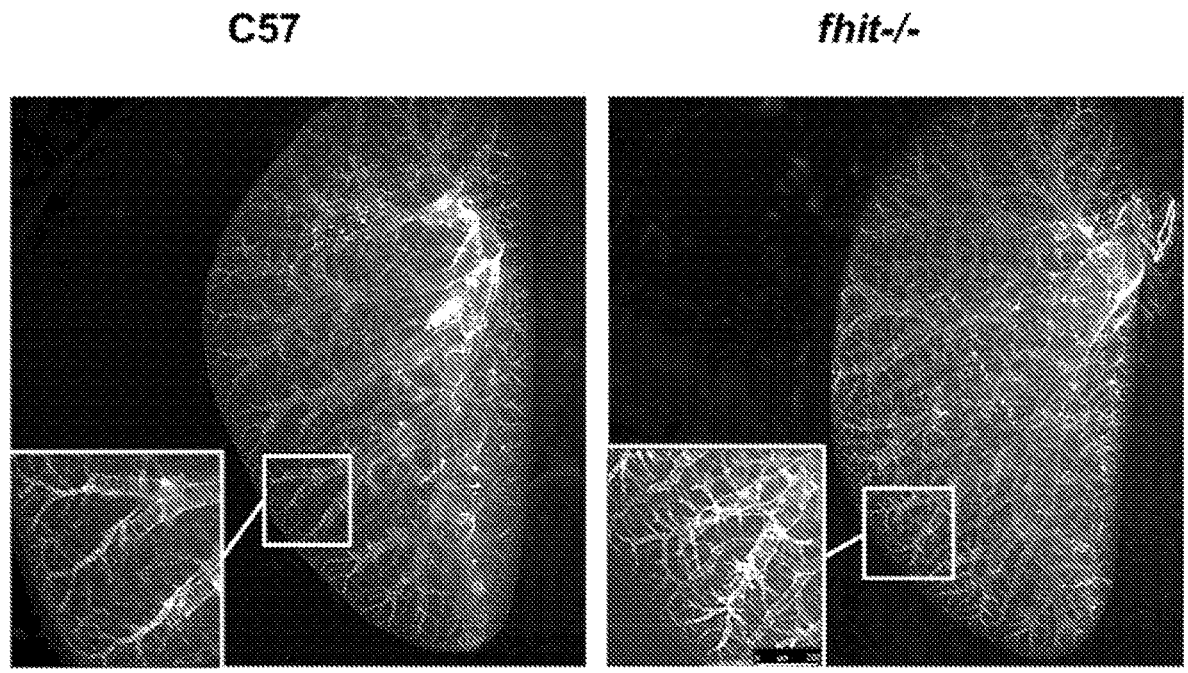
Figure 22:
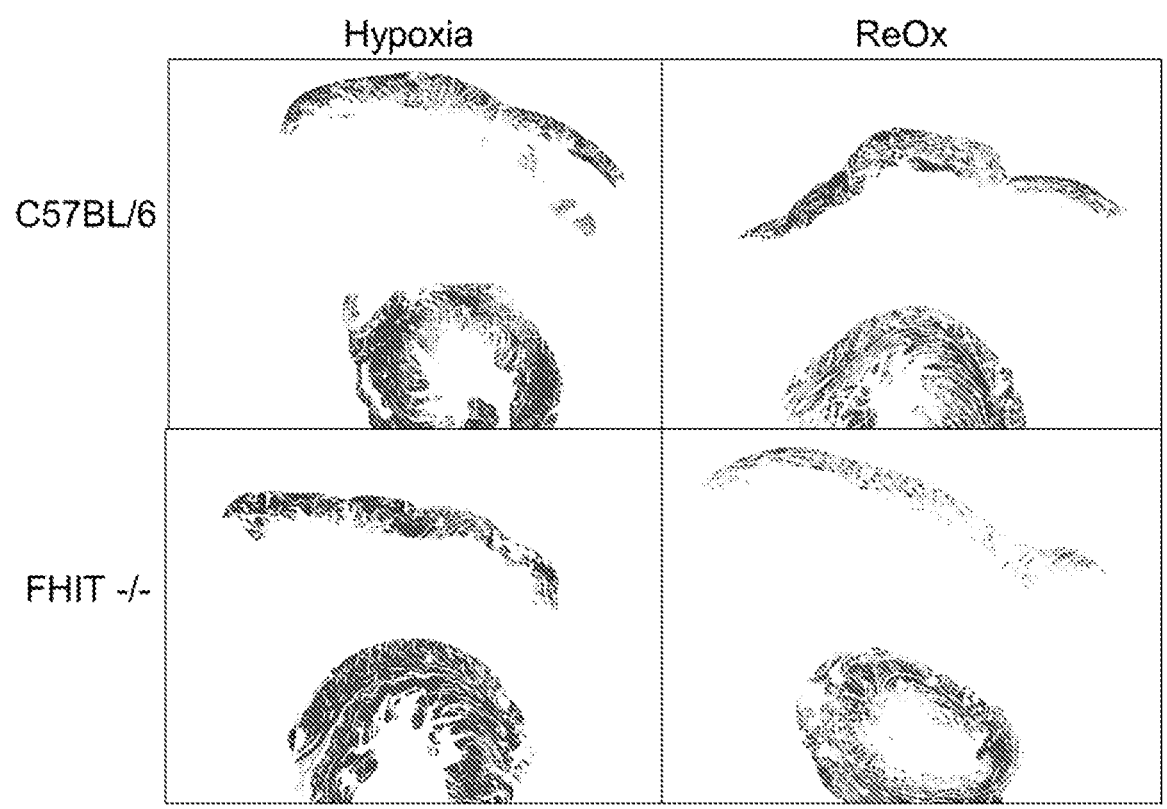
FIG. 22: WT and FHIT −/− C57BL/6 mice do not develop RV fibrosis following hypoxic treatment.

Example XI: FHIT-Deficiency In Vivo Predisposes to Exaggerated Pulmonary Hypertension in Response to Hypoxia Reduced FHIT in PAH patients and the importance of adequate FHIT levels in EC and SMC function led us to determine whether FHIT loss predisposes to PH in vivo. Fhit−/− mice and WT littermates (8 weeks of age, male/female) were exposed to chronic hypoxia (10%) for 3 weeks followed by a recovery period in normoxia (21%, 4 weeks) (38, 39). PH was assessed by measurement of RV systolic pressure (RVSP) through the right jugular vein. Animals were sacrificed and tissue collected at 3 and 7 weeks respectively. RV hypertrophy (RVH) was assayed using the weight ratio of RV to left ventricle and septum weight (RV/LV+S). C57BL/6 wildtype mice displayed a stereotypical adaptation response to hypoxia, with increases in RVSP (FIG. 10A, FIG. 18A), RVH (FIG. 10B, FIG. 18B), vascular rarefaction in arterioles and venules (FIGS. 10D, 18C) and increased muscularization (FIG. 10E, FIG. 18D), all reversible upon return to room air. In contrast, Fhit−/− mice displayed an exaggerated increase in RVSP and RVH, increased vascular rarefaction and muscularization in hypoxia, with incomplete resolution after 4 weeks normoxia (FIGS. 10A-10F, FIGS. 18A-F) yet no RV fibrosis (FIG. 22). Furthermore, baseline muscularization extended into more distal vessel generation in Fhit−/− mice (7-10 generations) compared to littermate controls (FIG. 10G-10H), where no muscularized vessels were observed beyond generation 7 (40). Of note, we discovered a sex difference in the degree of baseline RVSP, RVH, vascular rarefaction and small vessel muscularization (for detailed description see supplement).

Figure 10I:
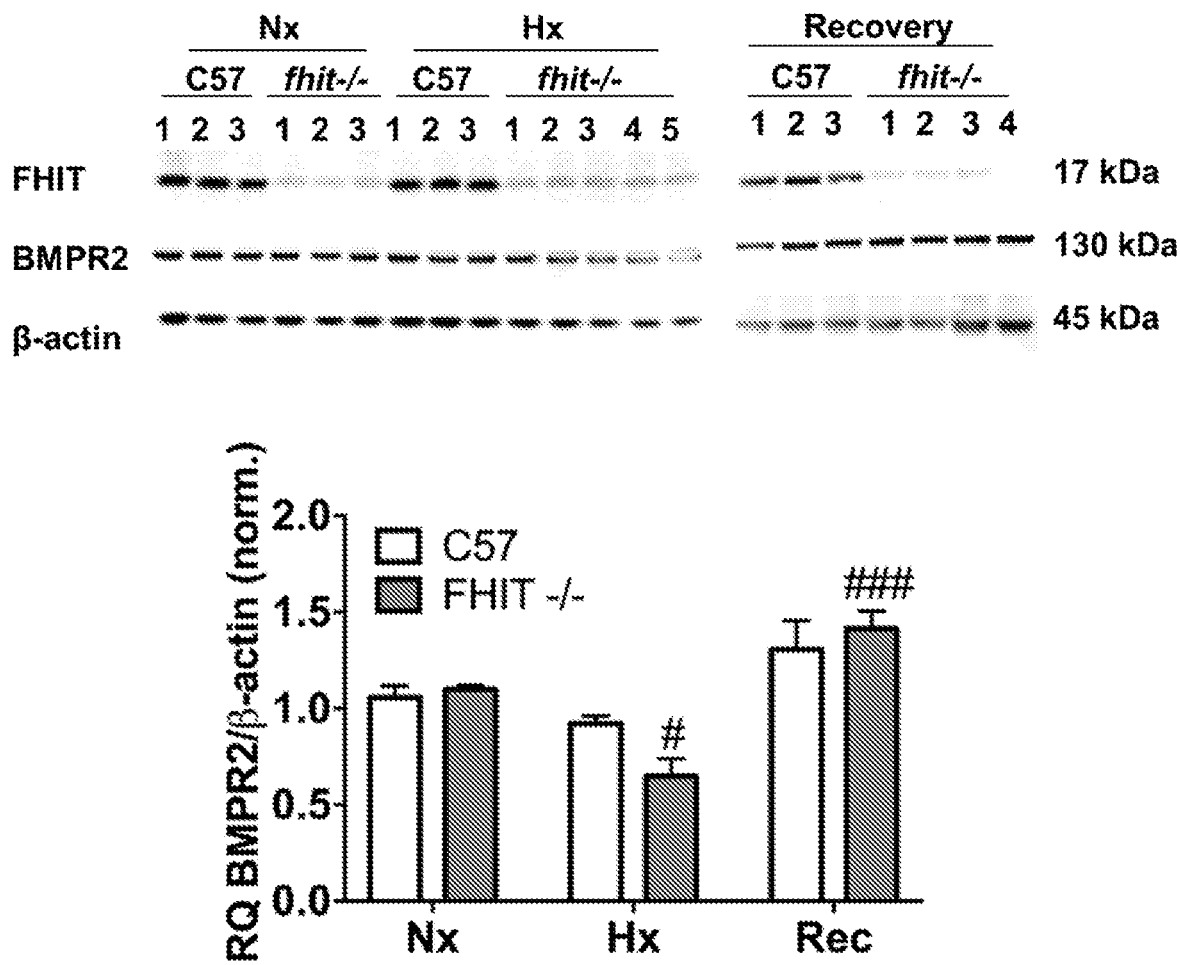
Figure 23A:
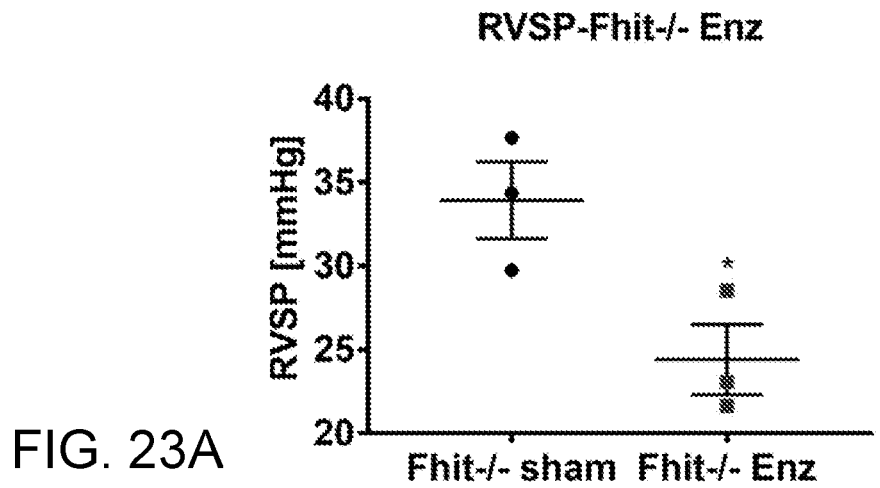
FIGS. 23A-23C: Enzastaurin protects from increased RVSP and up-regulates BMPR2/Id1 mRNA in hypoxia in FHIT −/− mice.
Figure 23B:
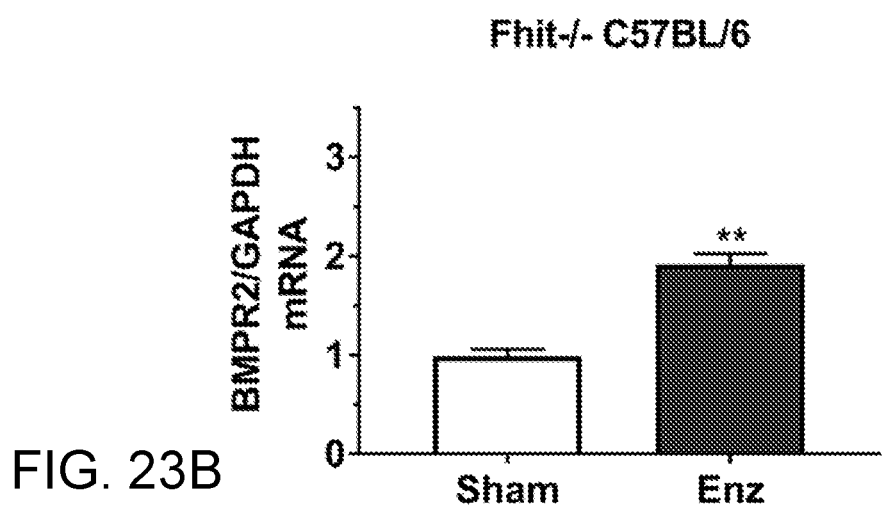

As expected, FHIT protein was significantly decreased in Fhit−/− lungs in all conditions. Chronic hypoxia decreased BMPR2 protein in Fhit−/− lungs, correlating with the observed RVSP and RVH increases in chronic hypoxia in Fhit−/− mice (FIG. 10I). Surprisingly, Fhit−/− mice exposed to hypoxia and treated with Enzastaurin (5 mg/kg/day via mini osmotic pump) showed an improved PH as well as increased BMPR2 and ID1 expression in whole lung tissue. As expected, FHIT mRNA expression was unmeasurably low, suggesting additional FHIT independent mechanisms of Enzastaurin on BMPR2 modulation (FIG. 23B).

Enzastaurin Prevents PH in Mice Exposed to Chronic Hypoxia

Given Enzastaurin's ability to increase FHIT and BMPR2 levels as well as its beneficial effect on endothelial and smooth muscle cell dysfunction, we used Enzastaurin in in vivo rodent models to assess its propensity to prevent or reverse experimental PH and vascular remodeling. Due to the increased severity of PH in male Fhit−/− mice in hypoxia, we used Enzastaurin exclusively in male animals. As a pilot prevention model, we exposed Bmpr2+/− mice and wildtype littermates (8 weeks of age) to hypoxia (10%) for 3 weeks with a subcutaneously implanted mini-osmotic pump, supplying 15 mg/kg/day Enzastaurin or vehicle. Enzastaurin prevented RVSP and RVH increases (FIG. 24A, 24B), vascular rarefaction as well as muscularization of distal vessels (FIG. 24C, 24D) in Bmpr2+/− and wildtype mice. We furthermore treated C57BL6 mice exposed to 3 weeks hypoxia with either FK506 (0.05 mg/kg/d), Enzastaurin (5 mg/kg/d) or a combination of both and documented an additive effect of FK506 and Enzastaurin with regards to prevention of PH (as measured by RVSP), BMPR2 as well as ID1 expression (FIGS. 25A-25D).

Example XII. Enzastaurin Reverses Experimental PH in SUGEN5416/Hypoxia/Normoxia Rats As a reversal model, we employed the SUGEN5416/Hypoxia/Normoxia rat model, which mimics human end-stage PAH well, with extensive vascular remodeling. Data for this experimented are summarized in FIGS. 11A-11K.

Sprague Dawley rats, were subcutaneously injected with 20 mg/kg SUGEN5416 once and housed in chronic hypoxia (10%, 3 weeks), followed by 5 weeks in normoxia as previously described(41). 8 weeks after subcutaneous SUGEN5416 injection, rats received daily oral gavage with 5 mg/kg/day Enzastaurin or vehicle control for 3 weeks. Hemodynamic assessment of the animals (echocardiography, right heart catheter) was performed before sacrifice and tissue collection. Rats developed severe obliterative "end-stage" PH that was characterized by luminal obliteration and right heart failure (FIG. 11D-H, FIG. 26). Consistently with the histological observations, RVSP (>100 mmHg) and RVH were severely increased in SUGEN5416-injected rats (FIGS. 11A-11B), and increased interstitial fibrosis was observed in the RV in these animals (FIGS. 11I-11K).

Figure 11A:
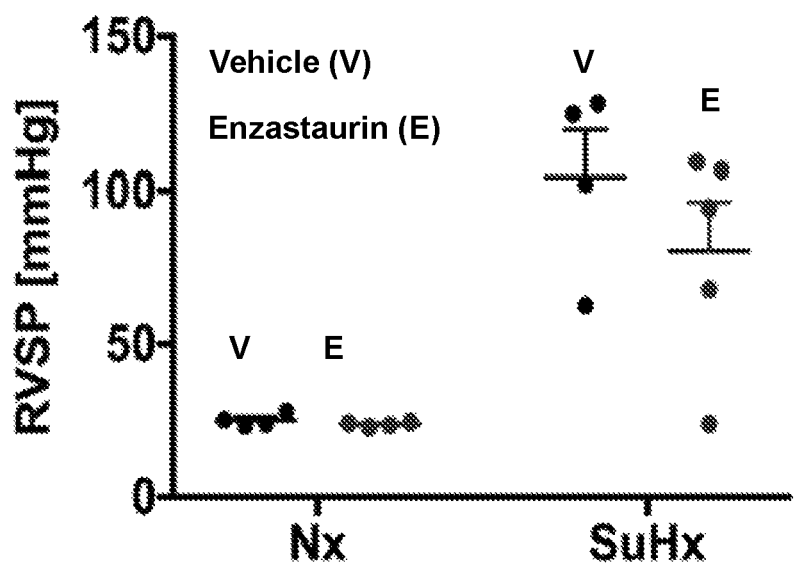
FIGS. 11A-11K: Enzastaurin reverses hemodynamic parameters, severe vascular remodelling, pulmonary emphysema, cardiac fibrosis and RVH in SUGEN 5416/hypoxia rats.
Figure 11B:
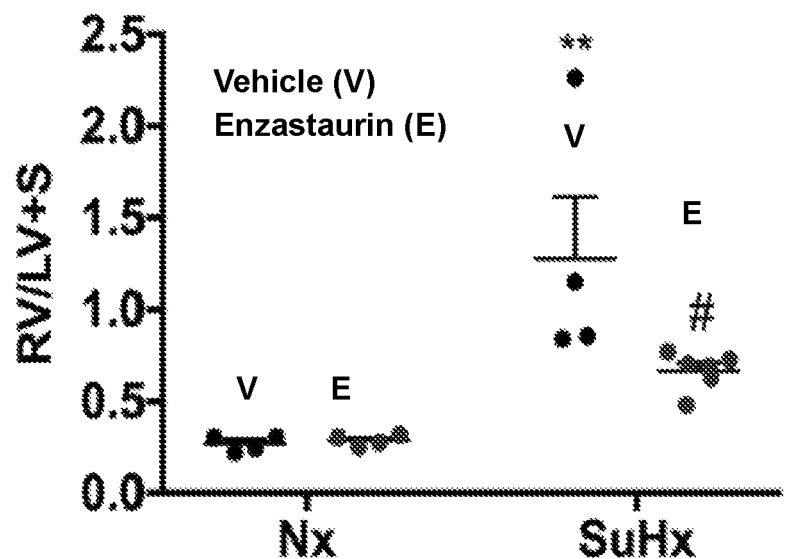
Figure 11C:
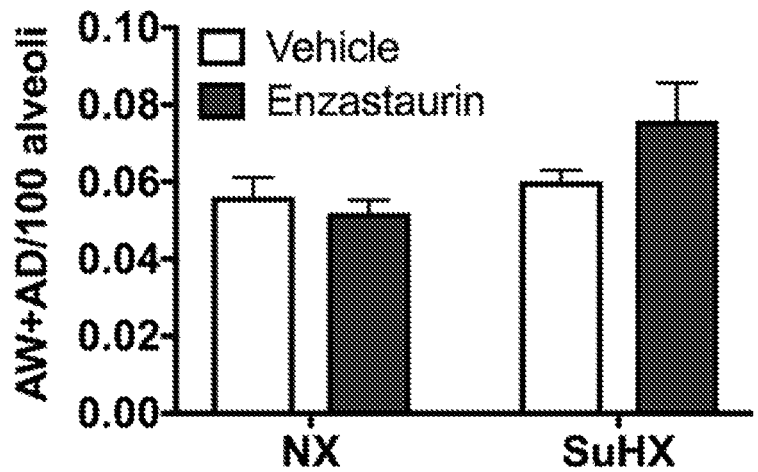
Figure 11D:
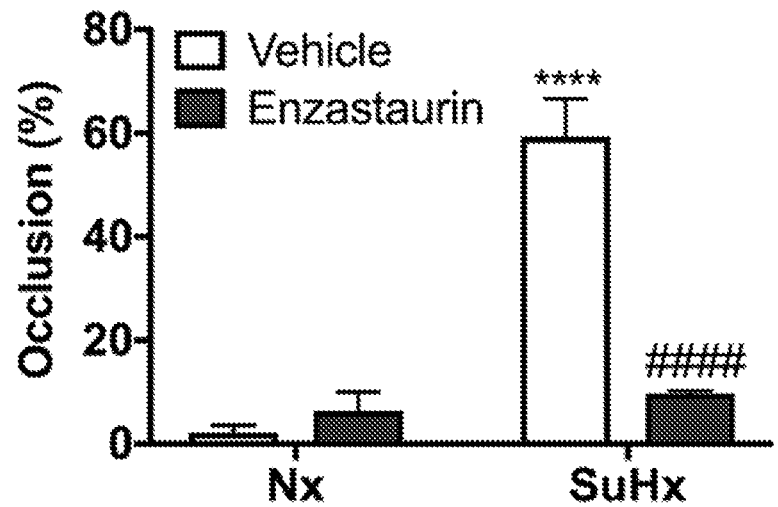
Figure 11E:
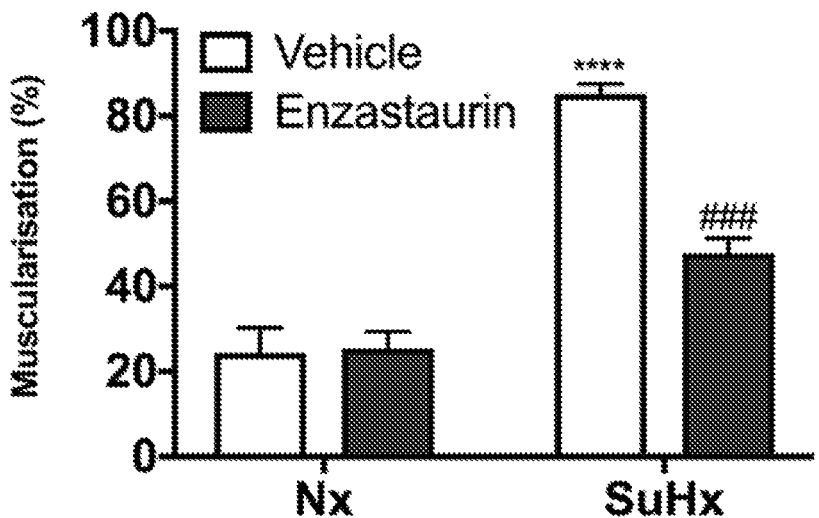
Figure 11F:
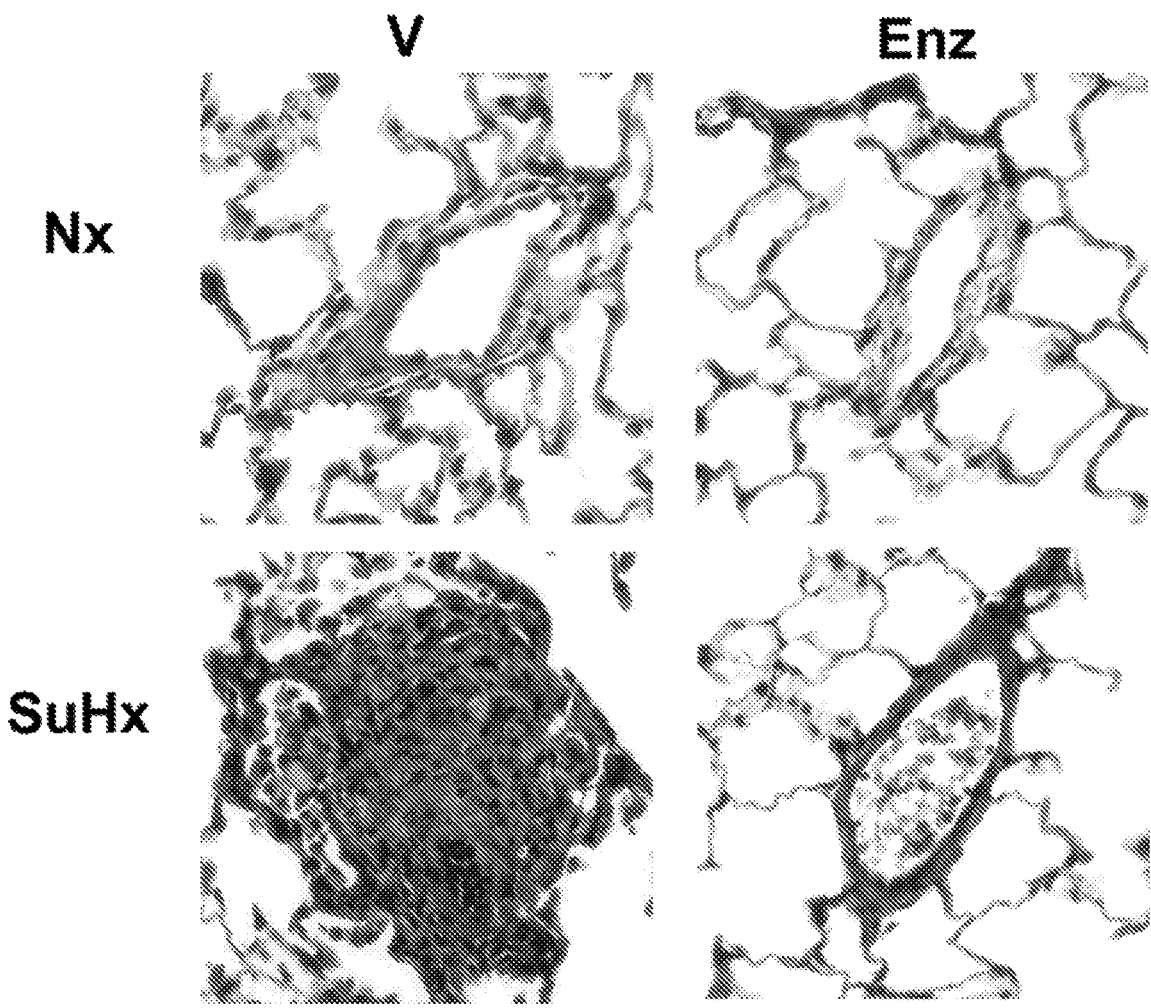
Figure 11G:
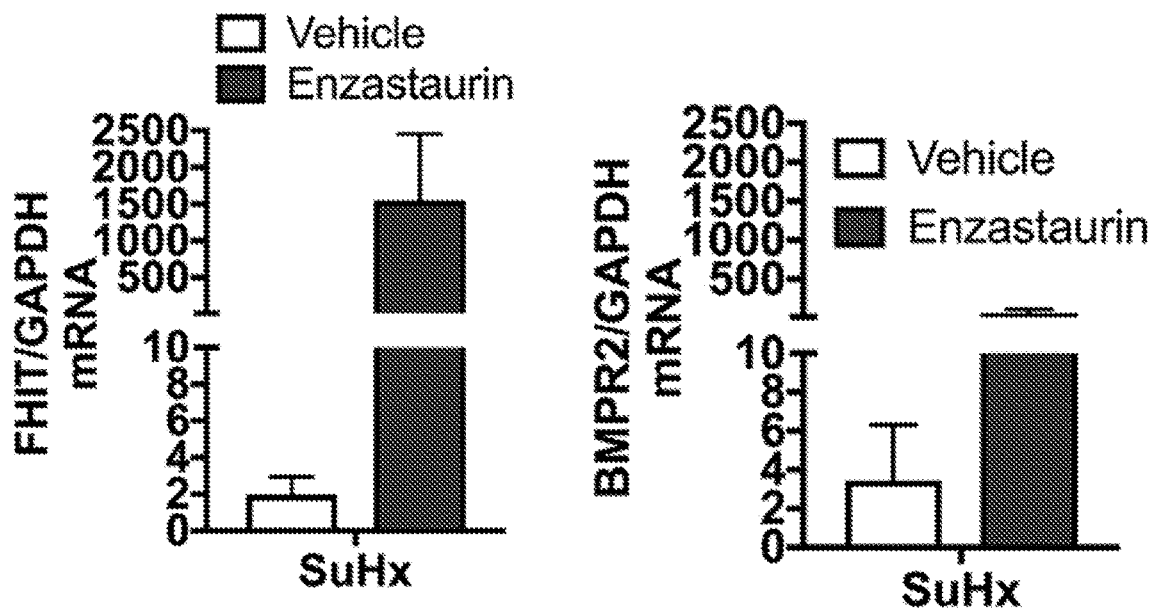
Figure 11H:
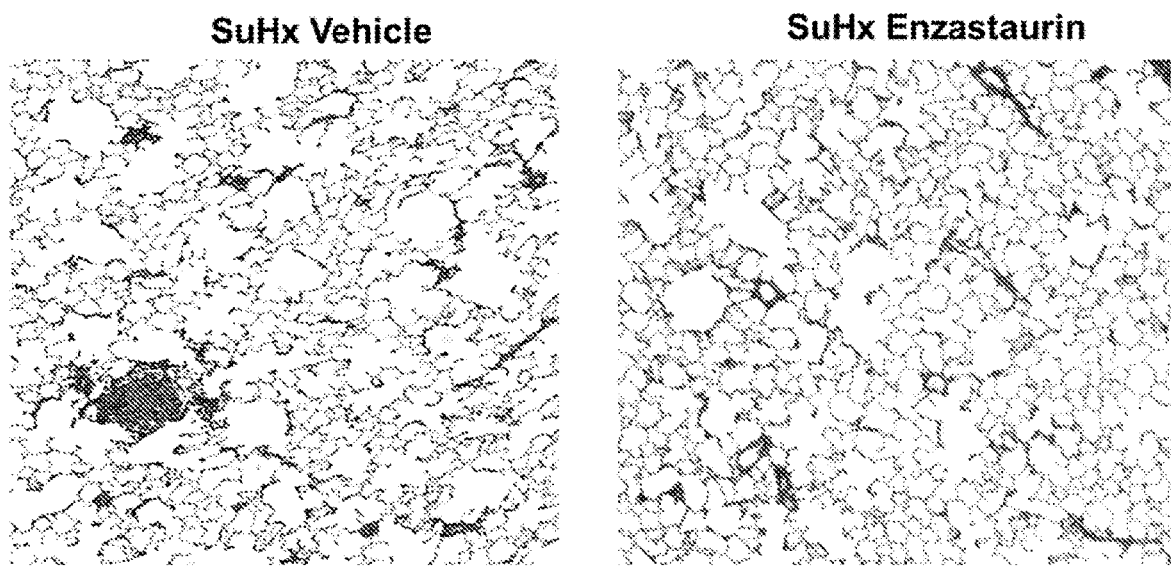
Figure 11I:
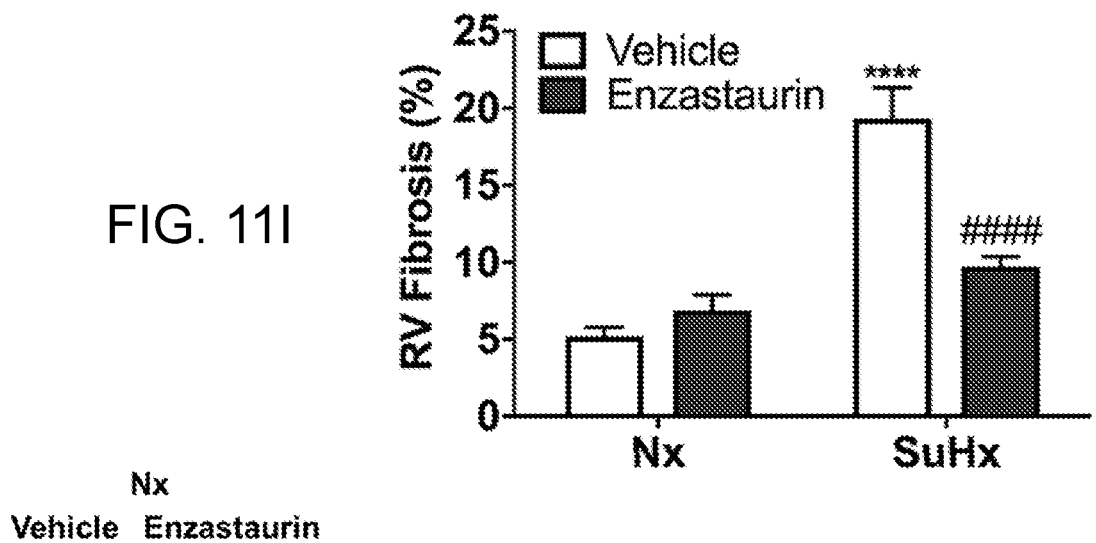
Figure 11J:
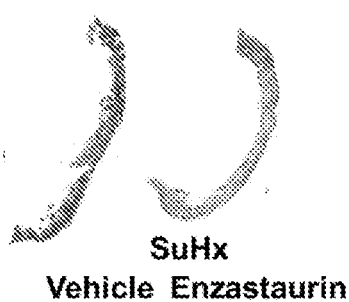
Figure 11J:
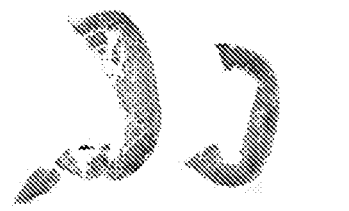
Figure 11K:
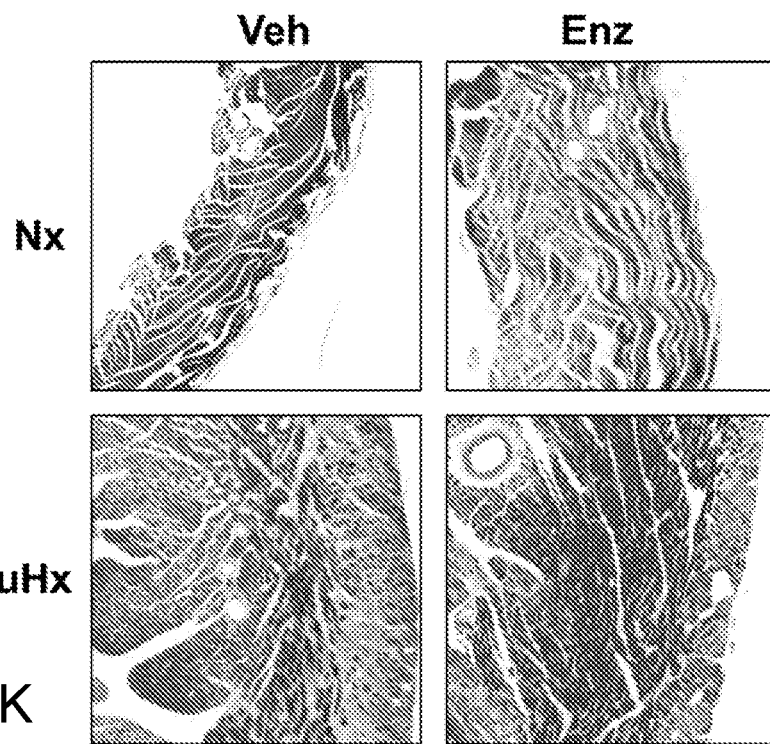

Data for this experiment are shown in FIGS. 11A to 11K, and show that Enzastaurin reverses hemodynamic parameters, severe vascular remodelling, pulmonary emphysema, cardiac fibrosis and RVH in SUGEN 5416/hypoxia rats. Experimental PH was induced in male Sprague Dawley rats by subcutaneous injection of 20 mg/kg body weight SU5416. Animals were housed for 3 weeks in hypoxic (Hx, 10% $O_2$) conditions, followed by a 5-week period in normoxia (Nx, 21% $O_2$), following daily administration of 5 mg/kg body weight Enzastaurin or vehicle control by oral gavage. FIG. 11A, Right ventricle systolic pressure (RVSP) was measured by pulmonary artery catheterisation (n=4, Mean±SEM, $p<0.01$ vs. Nx control, One Way ANOVA, Sidak's post-test). FIG. 11B, Right ventricle (RV) hypertrophy is demonstrated by the weight ratio of RV to left ventricle and septum (n=4, Mean±SEM, $p<0.01$ vs. Nx control, #$p<0.05$ vs. vehicle control, Two Way ANOVA, Turkey's post-test). FIG. 11C, Ratio of alveolar wall (AW) and alveolar duct (AD) pulmonary vessels, FIG. 11D, their full or partial occlusion (%) and, FIG. 11E, their full or partial muscularization (%) was assessed in MOVAT stained lung sections (n=4, Mean±SEM, **$p<0.0001$ vs. Nx control, ###$p<0.001$, ####$p<0.0001$, vs. vehicle control, Two Way ANOVA, Turkey's post-test). FIG. 11F, Representative MOVAT lung histology, highlighting large pulmonary vessels. FIG. 11G, Relative mRNA expression of FHIT or BMPR2 normalised to GAPDH in whole lung tissue (qPCR, n=4, Mean±SEM, Two-Way ANOVA). FIG. 11H, Representative MOVAT lung histology, presenting vessel occlusion. FIG. 11I, Percentage of fibrotic tissue compared to total tissue in the RV (n=4, Mean±SEM, $p<0.01$ vs. Nx control, ##$p<0.01$ vs. vehicle control, Two Way ANOVA, Turkey's post-test). FIGS. 11J-11K, Representative trichrome stains of whole RV histology (FIG. 11J) and magnified sections (FIG. 11K) are displayed.

Treatment with Enzastaurin increased FHIT and BMPR2 expression in whole lung (FIG. 11G), nearly entirely reversed vascular occlusions (FIG. 11D), and potently reduced muscularization of small and large vessels (FIG. 11E), as well as RVH (FIG. 11B) and RV fibrosis (FIG. 11I). RVSP was reduced by over 30 mmHg in Enzastaurin-treated SUGEN5416/Hypoxia/Normoxia rats.

Example XIII. Enzastaurin Reverses Pulmonary Emphysema in SUGEN 5416/Hypoxia Rats Experimental PH was induced in male Sasco Sprague Dawley rats by subcutaneous injection of 20 mg/kg body weight SU5416. Animals were housed for 3 weeks in hypoxic (Hx, 10% $O_2$) conditions, followed by a 5-week period in normoxia (Nx, 21% $O_2$), following daily administration of 5 mg/kg body weight Enzastaurin or vehicle control by oral gavage.

Figure 27A:
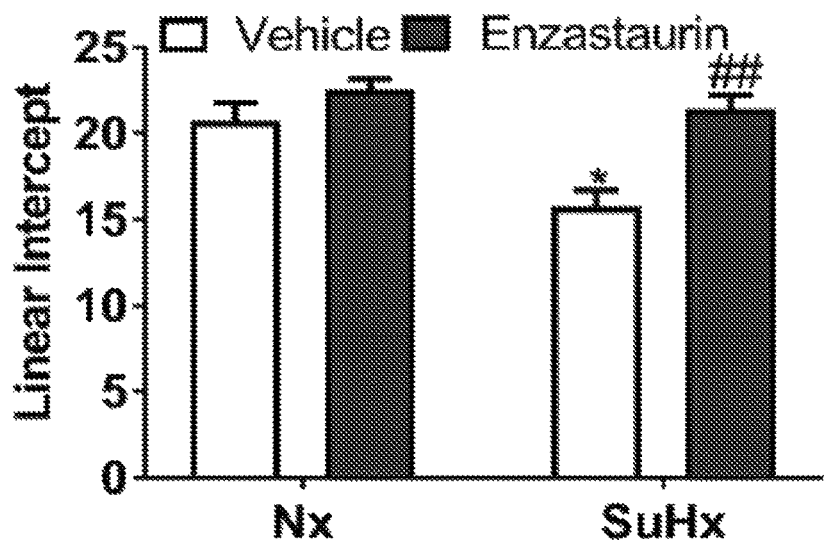
FIGS. 27A-27B: Enzastaurin-treated animals exhibit significantly less evidence of emphysematous changes and vessel occlusion than untreated controls.
Figure 27B:
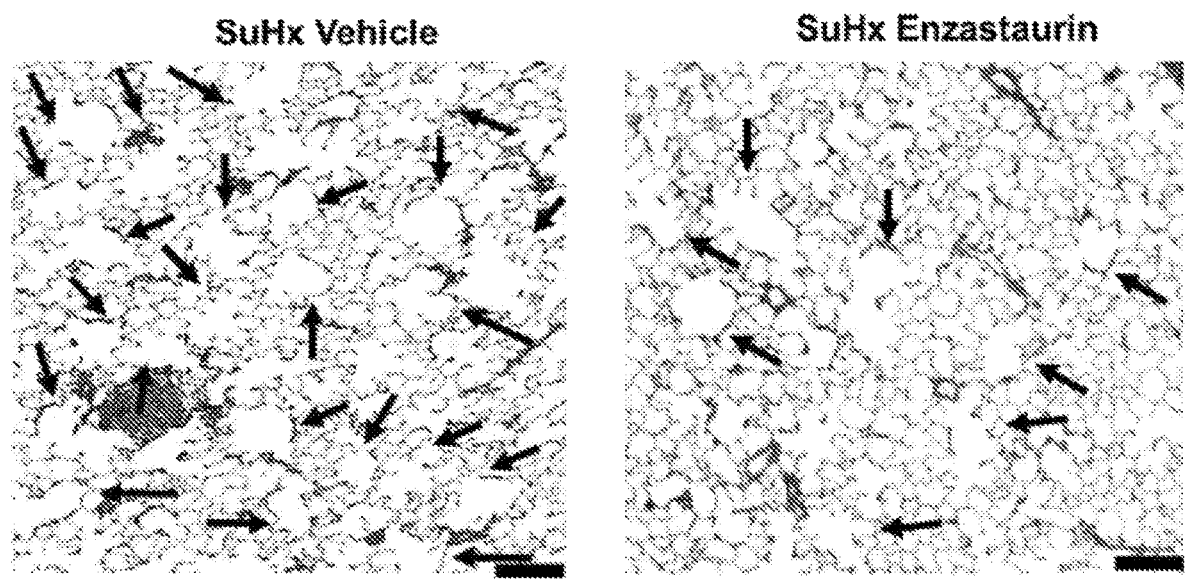

Linear intercept analysis of MOVAT lung histology (n=4, Mean±SEM, *$p<0.05$ vs. Nx control, ##$p<0.01$ vs. vehicle control, Two Way ANOVA, Turkey's post-test). Representative MOVAT lung histology, presenting emphysematous changes (as marked by arrows) and vessel occlusion. As the data in FIGS. 27A and 27B show, Enzastaurin treated animals exhibit significantly less evidence of emphysematous changes and vessel occlusion than untreated controls, showing that Enzastaurin can reverse lung tissue damage associated with emphysema.

Supplemental Examples

Example S1

Fhit−/− C57BL/6 vs. littermate wildtype (C57) mice were housed for three weeks in normoxic (Nx, 20% $O_2$), hypoxic (Hx, 10% $O_2$) conditions, a hypoxia-recovery (Rec, 3 weeks Hx/4 weeks Nx) period for 4 weeks, compared to 7 weeks Nx controls. Representative densitometric analysis of FHIT protein expression in lung tissue normalised to a β-actin housekeeping control (male, C57 n=3, Fhit−/− Nx n=3, Fhit−/− Hx n=5, Fhit−/− Rec n=4). All bars denote Mean±SEM. ****$p<0.0001$ vs. C57 control, Two Way ANOVA, Turkey's post-test. Data for this experiment are summarized in FIG. 12.

Example S2

Figure 13A:
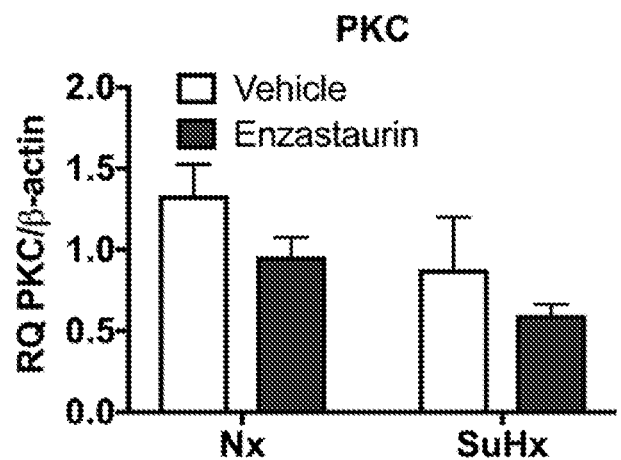
FIGS. 13A-13D: PKC and p-PKC protein expression in Sprague Dawley rat lungs, comparing Normoxia and Sugen/Hypoxia conditions after 3 weeks of Enzastaurin treatment.
Figure 13B:
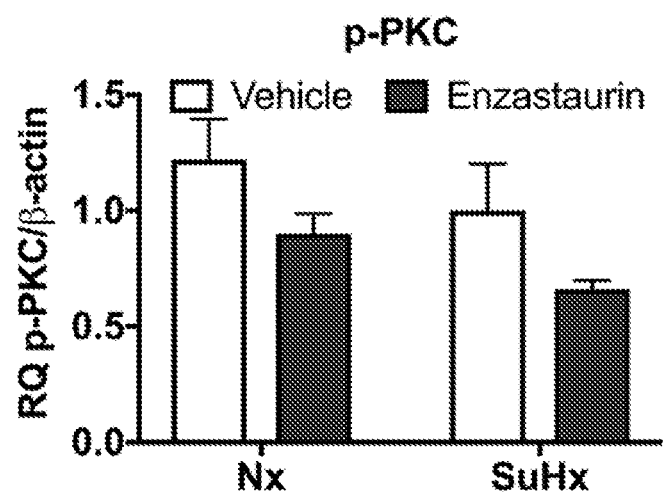
Figure 13C:
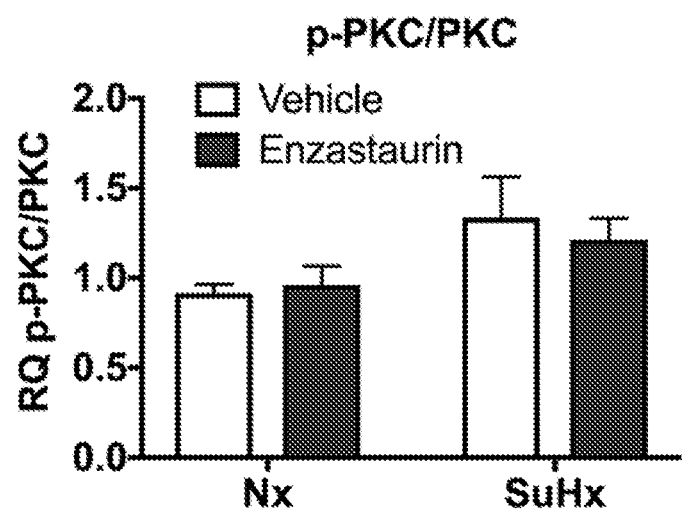
Figure 13D:
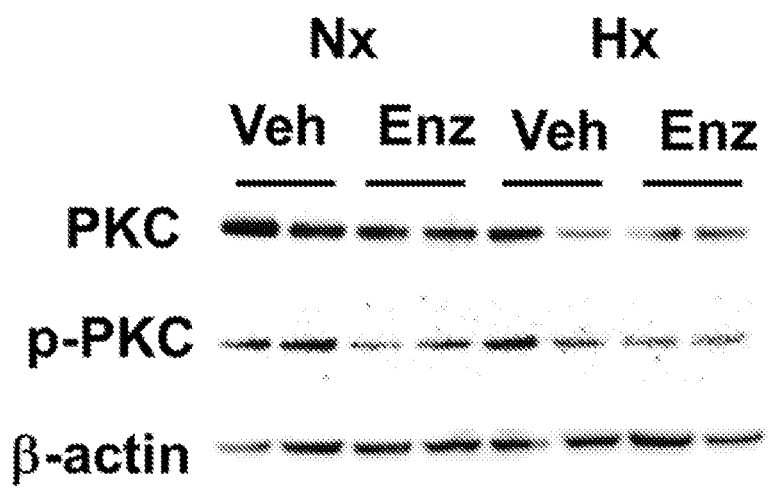
Figure 14A:
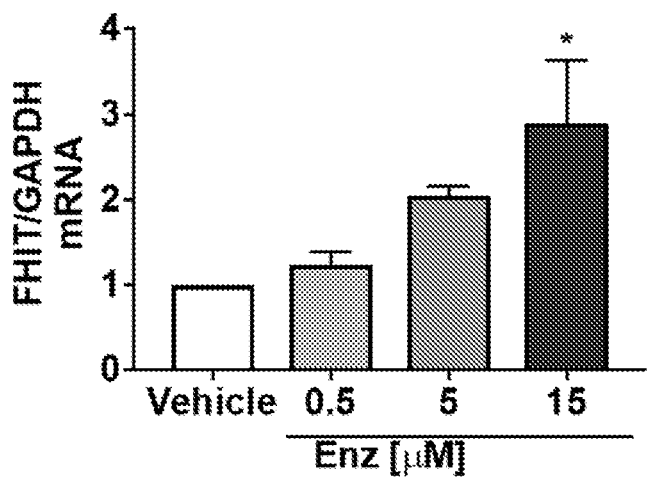
Figure 14B:
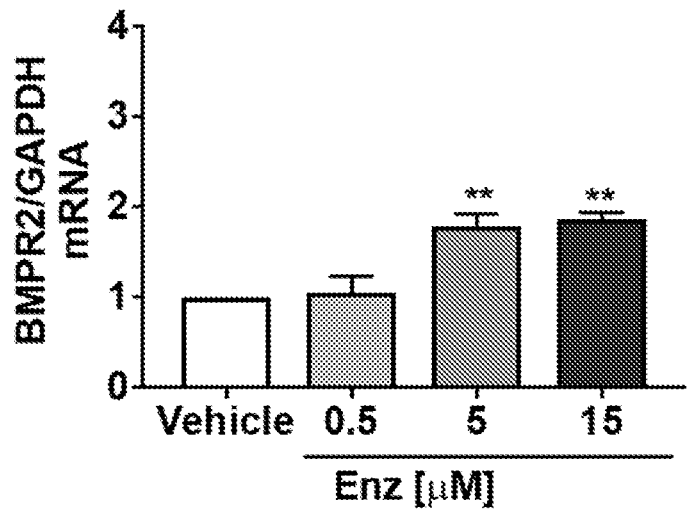
Figure 14C:
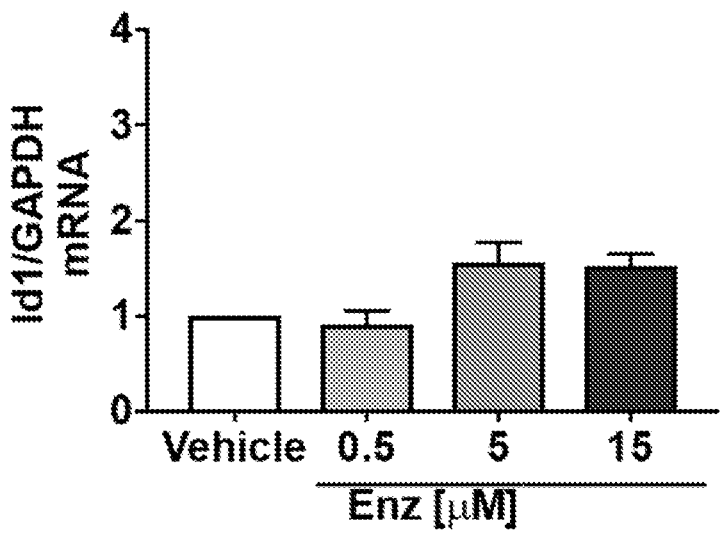

Experimental PAH was induced in male Sasco Sprague Dawley rats by subcutaneous injection of 20 mg/kg body weight SU5416. Animals were housed for 3 weeks in hypoxic (Hx, 10% $O_2$) conditions, followed by a 5 week period in normoxia (Nx, 20% $O_2$), following daily administration of 5 mg/kg body weight Enzastaurin or vehicle control by oral gavage. Densitometric analysis of PKC (FIG. 13A) and p-PKC (FIG. 13B) protein expression in lung tissue normalised to a β-actin housekeeping control (male, Nx n=4, Nx Enz n=4, SuHx n=3, SuHx Enz n=5) and p-PKC normalised to PKC (FIG. 13C). Representative blots of PKC, p-PKC and β-actin (FIG. 13D). All bars denote Mean±SEM. Two Way ANOVA, Turkey's post-test.

Example S3

Human PAEC were plated on 6 well plates. When being 70-80% confluent, cells were treated with Enzastaurin at 0.5 mM, 5 mM and 15 mM respectively for 24 hours. RNA was isolated by RNeasy® Plus Mini Kit (Qiagen) and Fhit, BMPR2 and Id1 gene expression was measured by Taqman® gene expression assay. (FIG. 14A) Relative expression of FHIT (FIG. 14B) BMPR2, (FIG. 14C) ID1. All bars denote Mean±SEM., n=3, One Way ANOVA, Dunnet's comparison test *$p<0.05$, **$p<0.01$ compared to control.

Example S4

Figure 15A:
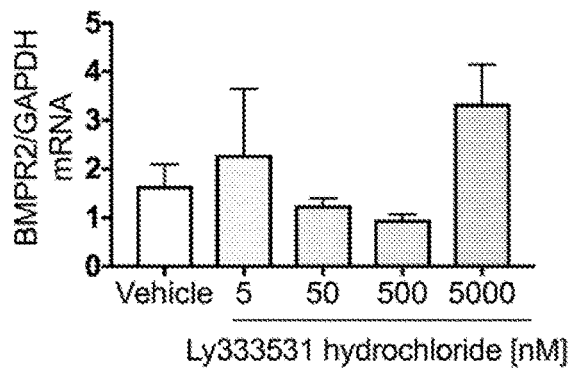
FIGS. 15A-15F: PKC inhibition by pharmaceutical PKC inhibitors, other than Enzastaurin, does not increase BMPR2-signaling and FHIT expression.
Figure 15B:
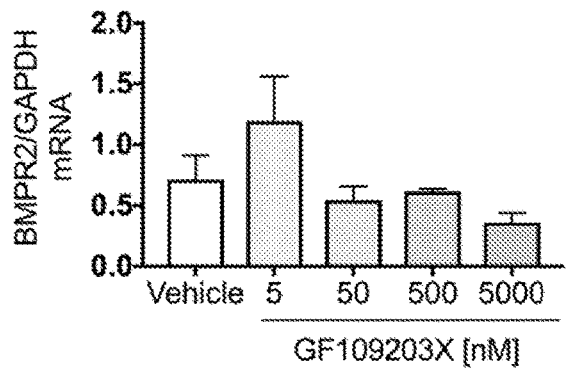
Figure 15C:
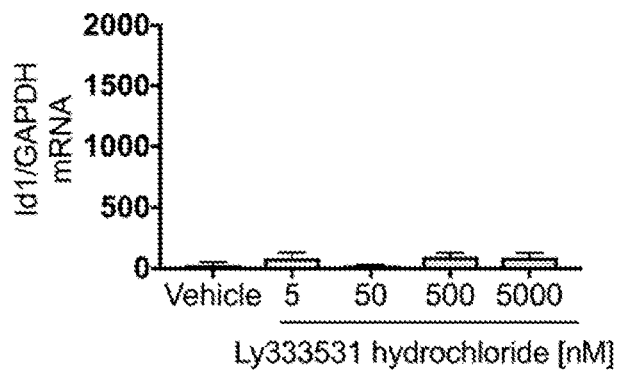
Figure 15D:
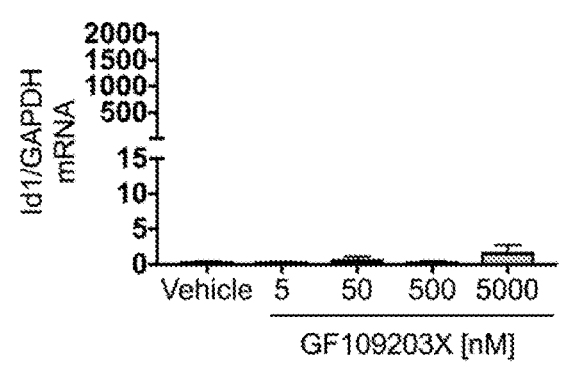
Figure 15E:
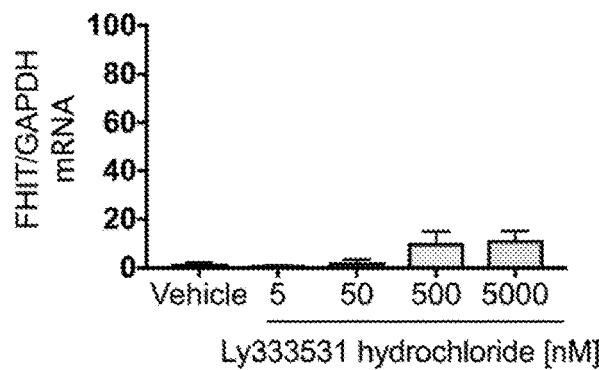
Figure 15F:
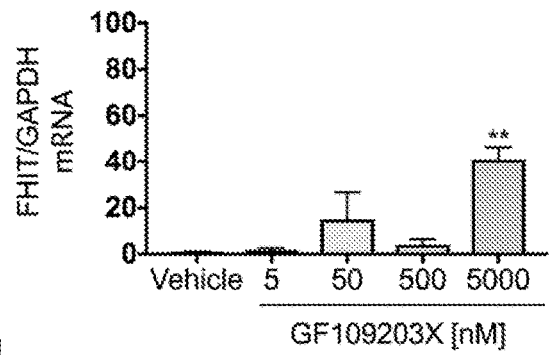
Figure 16:
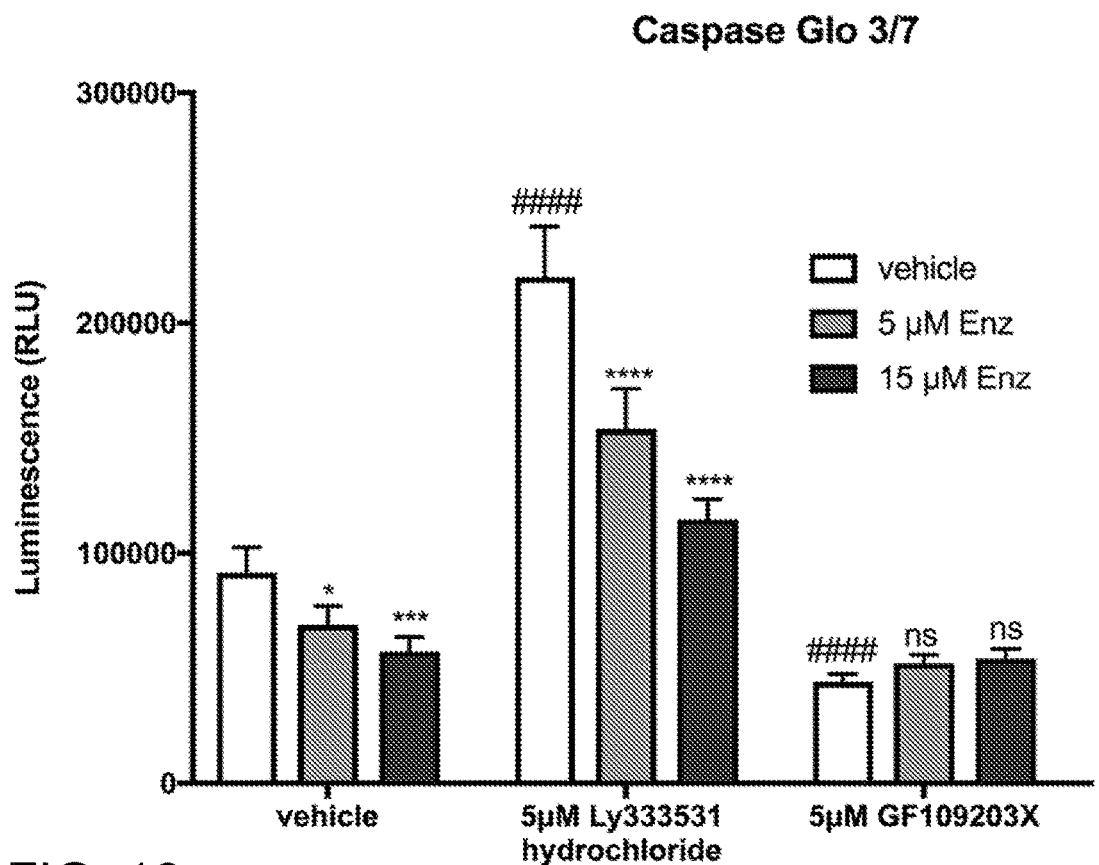
FIG. 16: Enzastaurin, but not PKCβ inhibitor Ly333531, decreases Caspase 3/7-mediated apoptosis in PAECs.

FIGS. 15A-15B, Relative mRNA expression of BMPR2 normalised to GAPDH in synchronised PAECs incubated for 24 hours with varying concentrations (5 nM -5 µM) of (FIG. 15A) the selective PKCβ inhibitor Ly333531 hydrochloride (FIG. 15B) or the non-selective PKC-inhibitor GF109203X (qPCR, t=24h, n=3, Mean±SEM, One Way ANOVA, Dunnett's post-test, NS). FIGS. 15C-15D, Relative mRNA expression of Id1 normalised to GAPDH in synchronised PAECs incubated for 24 hours with varying concentrations (5 nM-5 M) of (FIG. 15C), the selective PKCβ inhibitor Ly333531 hydrochloride (FIG. 15D) or the non-selective PKC-inhibitor GF109203X (FIG. 15F) (qPCR, t=24h, n=3, Mean±SEM, One Way ANOVA, Dunnett's post-test, NS). FIGS. 15E-15F, Relative mRNA expression of FHIT normalised to GAPDH in synchronised PAECs incubated for 24 hours with varying concentrations (5 nM-5 µM) of (FIG. 15E), the selective PKCβ inhibitor Ly333531 hydrochloride (FIG. 15F) or the non-selective PKC-inhibitor GF109203X (I) (qPCR, t=24h, n=3, Mean±SEM, **$p<0.01$, vs. vehicle control, One Way ANOVA, Dunnett's post-test).

Example S5

Caspase 3/7 luminescence in synchronised PAECs incubated for 24 hours with 5 µM or 15 µM of Enzastaurin (shaded bars) and/or 5 µM of the selective PKCβ inhibitor Ly333531 hydrochloride or 5 µM of the non-selective PKC-inhibitor GF109203X (t=24 h, Caspase-Glo® 3/7 Assay, n=3, Mean±SEM, *$p<0.05$, *$p<0.001$, **$p<0.0001$ vs. non-Enzastaurin treated control, ####$p<0.0001$ vs. untreated vehicle control, Two-Way ANOVA, Dunnett's post-test). See FIG. 16.

Example S6

Representative Immunohistochemistry slides from IPAH patient (without a BMPR2 mutation). FIG. 17A: BMPR2 expression, FIG. 17B: FHIT expression. FHIT reduction is mainly localized in neointima.

Example S7

Figure 18A:
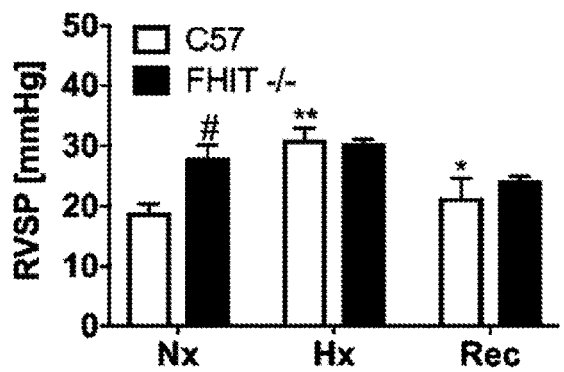
FIGS. 18A-18F: Fhit−/− C57BL/6 mice develop experimental PAH after chronic exposure to Hypoxia.
Figure 18B:
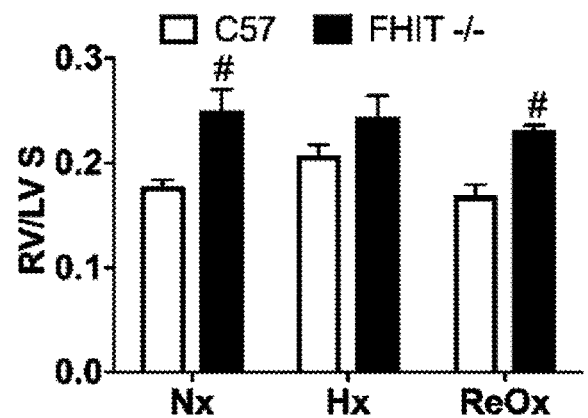
Figure 18C:
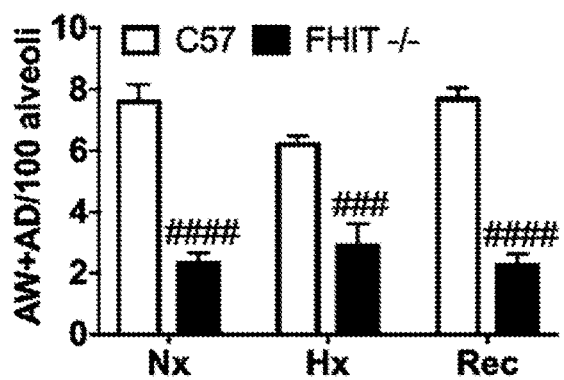
Figure 18D:
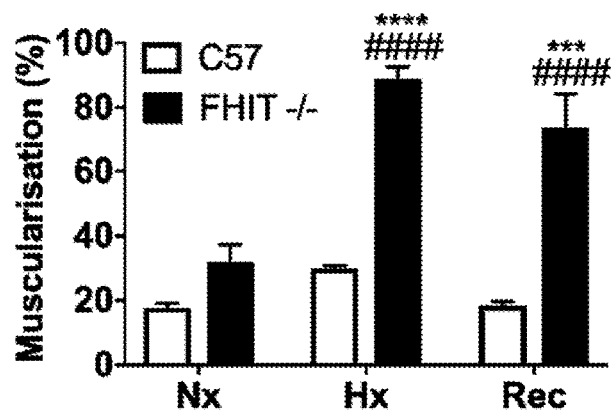
Figure 18E:
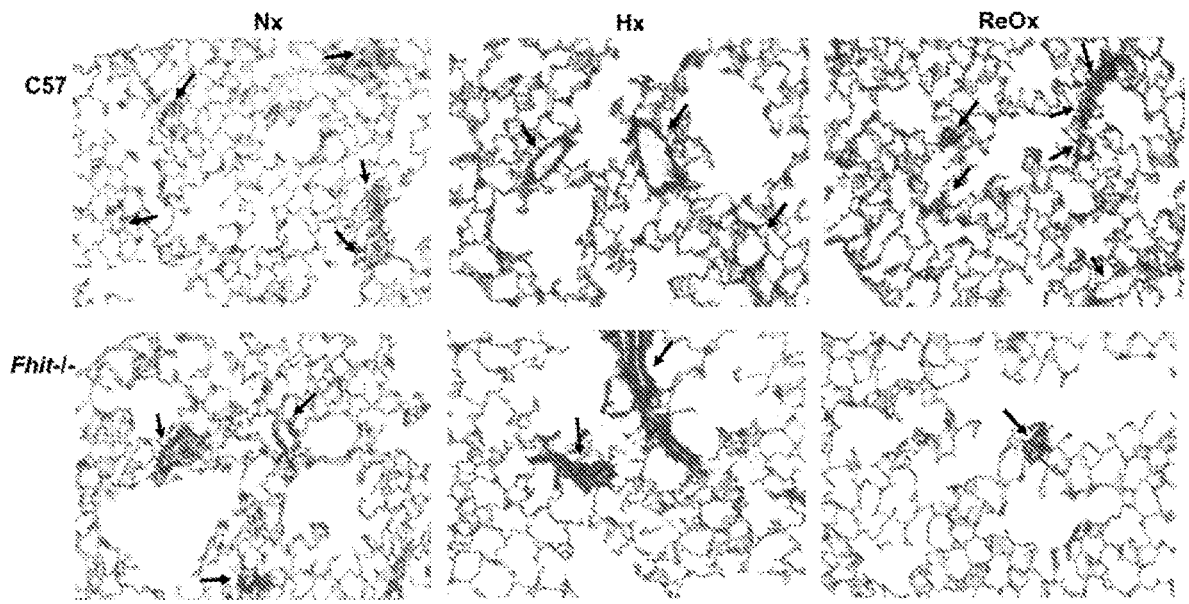
Figure 18F:
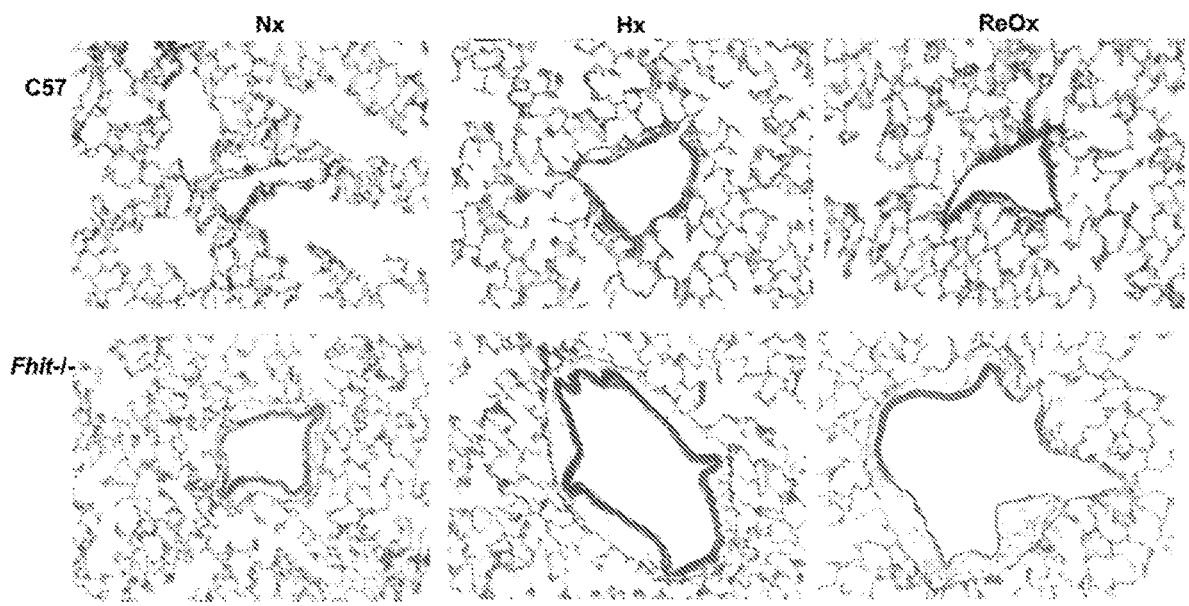

Female Fhit−/− C57BL/6 vs. littermate wildtype (C57) mice were housed for three weeks in normoxic (Nx, 20% $O_2$), hypoxic (Hx, 10% $O_2$) conditions, a hypoxia-recovery (Rec, 3 weeks Hx/4 weeks Nx) period for 4 weeks, compared to 7 weeks Nx controls. Data are shown in FIGS. 18A-18F: FIG. 18A, Right ventricle systolic pressure (RVSP) was measured by pulmonary artery catheterisation (female, C57 n=3, FHIT −/− Nx n=4, FHIT −/− Hx Rec n=3). FIG. 18B, Right ventricle (RV) hypertrophy is demonstrated by the weight ratio of RV to left ventricle and septum (RV/LV+S) (female, C57 n=3, Fhit−/− Nx n=4, FHIT −/− Hx n=3, Fhit−/− Rec n=5). FIG. 18C, Loss of alveolar wall (AW) and alveolar duct (AD) pulmonary vessels. FIG. 18D, Full or partial muscularization (%) of AW or AD vessels was assessed in MOVAT stained lung sections (female, C57 n=3, Fhit−/− Nx n=4, Fhit−/− Hx Rec n=3). FIGS. 18E-18F, Representative MOVAT lung histology representing vessel loss of small distal vessels (FIG. 18E) or vessel muscularization (FIG. 18F). Arrows indicate vessel position. *$p<0.05$, $p<0.01$, *$p<0.001$, ****$p<0.0001$ vs. Nx control, #$p<0.05$, ###$p<0.001$, ####$p<0.0001$ vs. C57 control, Two Way ANOVA, Turkey's post-test.

Figure 19A:
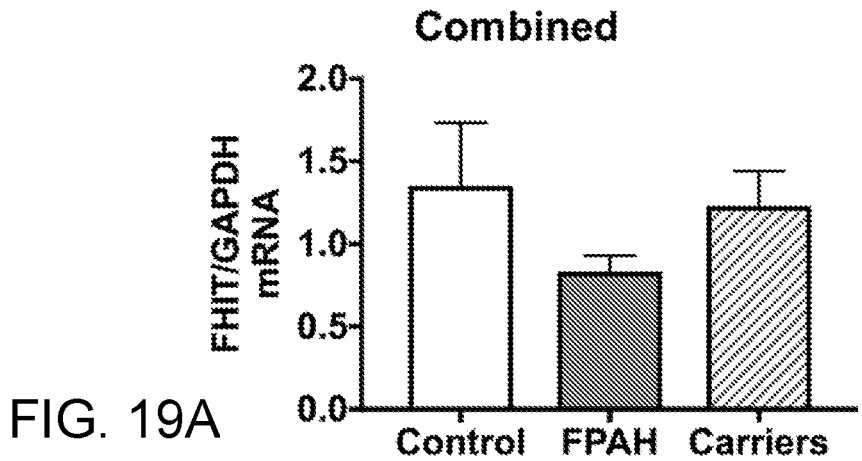
FIGS. 19A-19H: Sex difference in BMPR2 expression in FPAH and Carriers versus healthy controls.
Figure 19B:
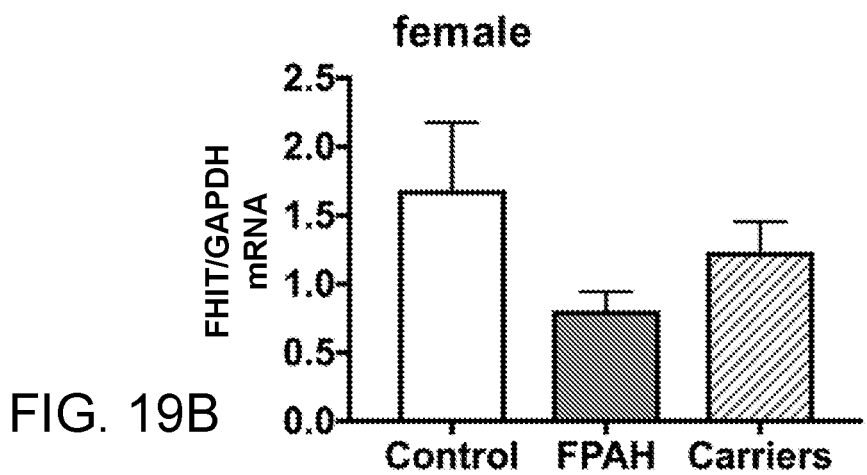
Figure 19C:
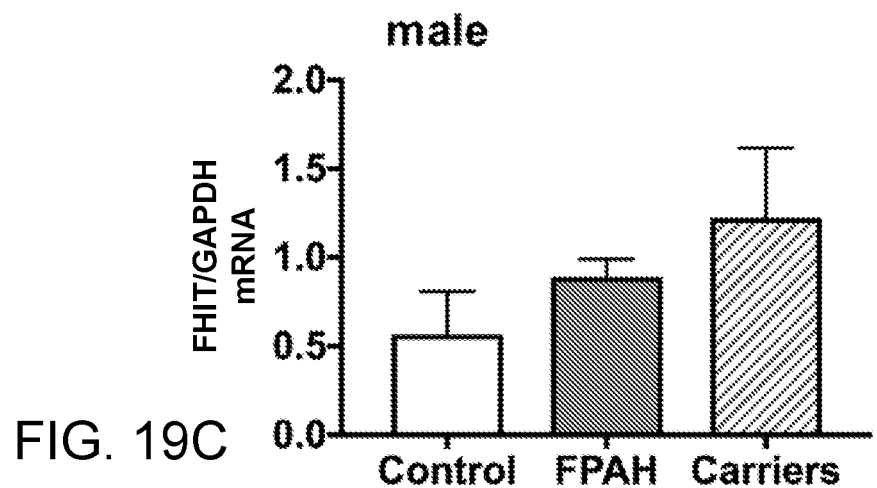
Figure 19D:
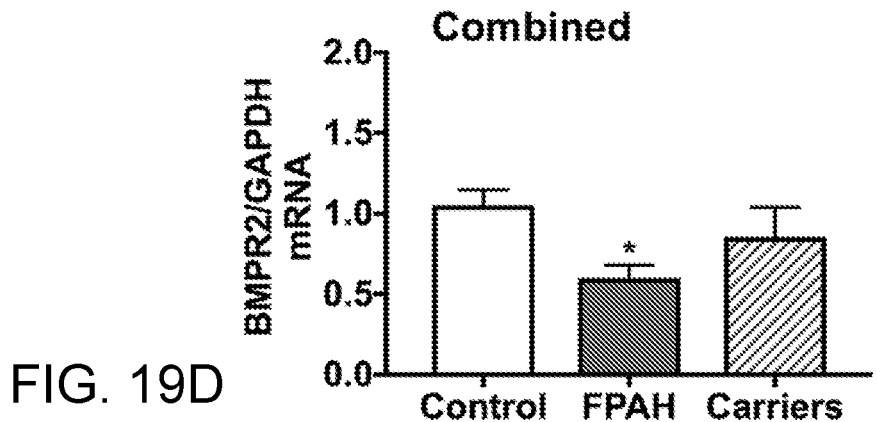
Figure 19E:
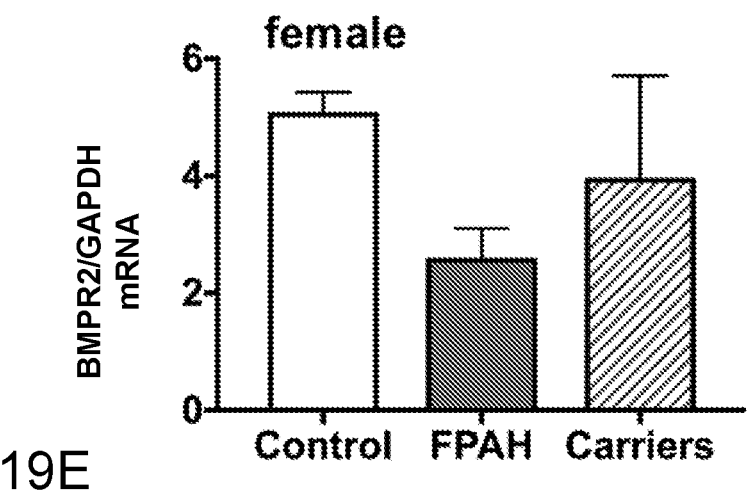
Figure 19F:
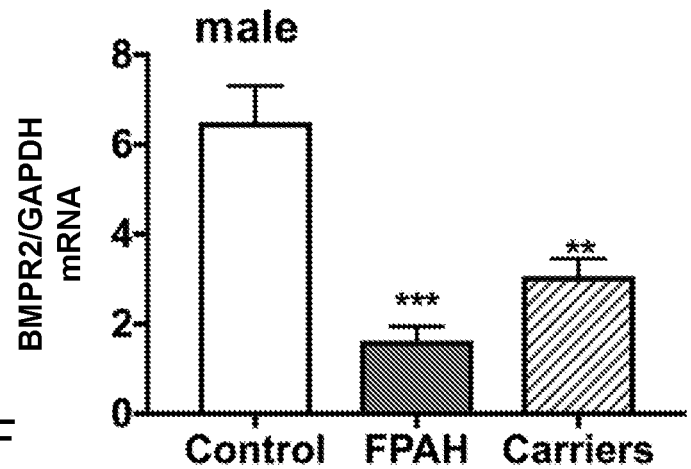
Figure 19G:
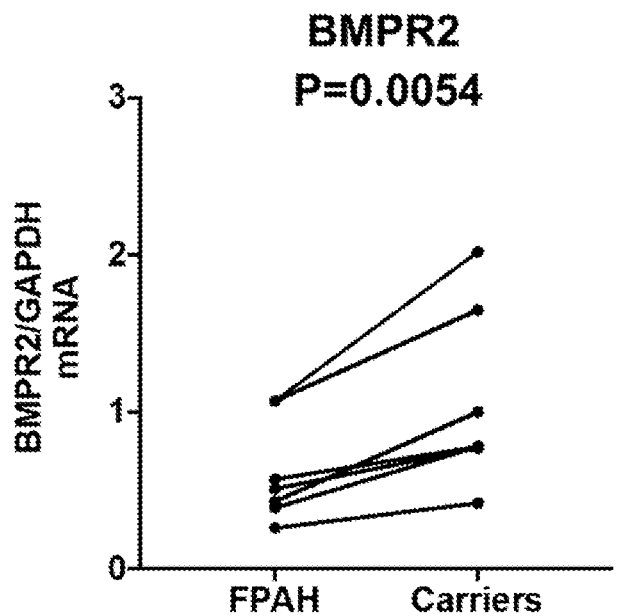
Figure 19H:
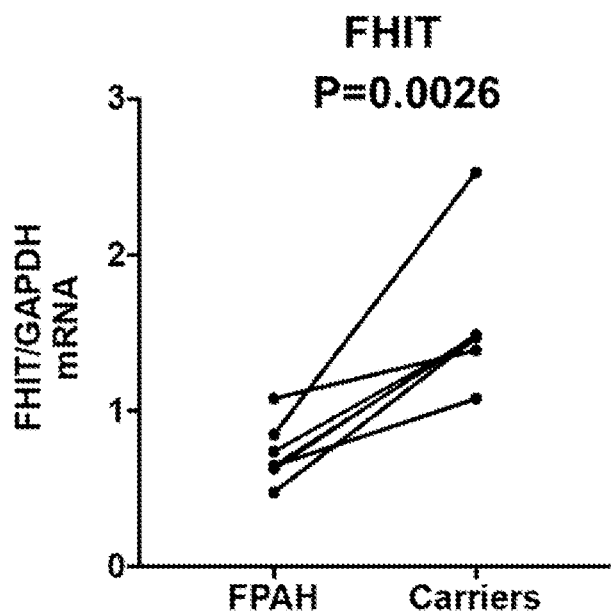

Example S8 qPCR mRNA analysis of FHIT is summarized in FIGS. 19A-19H: (FIGS. 19A-19C) and BMPR2 (FIGS. 19D-F) expression in transformed lymphocytes from selected families with FPAH patients and healthy mutation carrier compared to healthy controls analyzed for females (FIGS. 19B, 19E), males (FIGS. 19C, 19F) and combined subjects (FIGS. 19A,19D). N=10, Mean±SEM, *$p<0.05$, One-Way ANOVA, Dunnett's post-test, for patient demographics see Table 1. (FIGS. 19G, 19H) Graphic display of BMPR2 and FHIT expression in FPAH patients compared to the carriers of the same family. Paired t-test p=0.0054 BMPR2, p=0.0026 FHIT.

Example S9

Human PAEC were plated on the 6 well plates ($0.5 \times 10^6$ cells/well) and transfected with siFhit (Ambion Silencer®

Figure 20A:
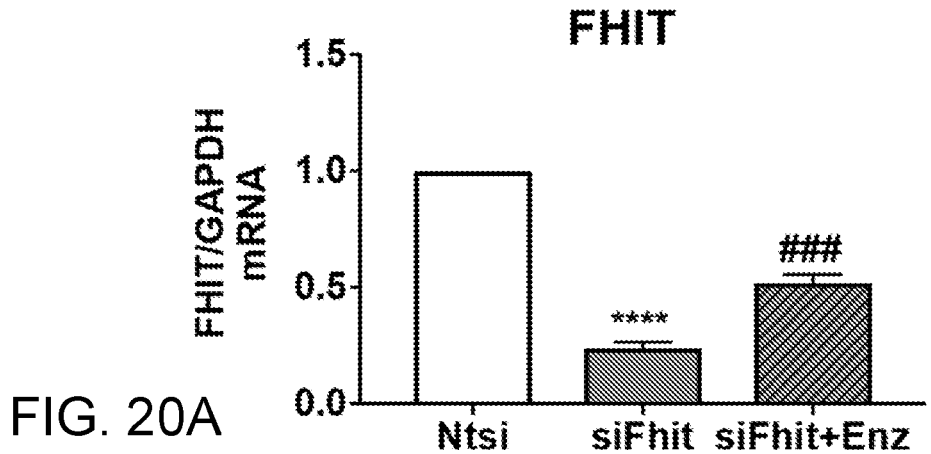
FIGS. 20A-20C: 24 h treatment with Enzastaurin increases FHIT, BMPR2 and Id1 expression in PAECs in which FHIT is reduced by siRNA.
Figure 20B:
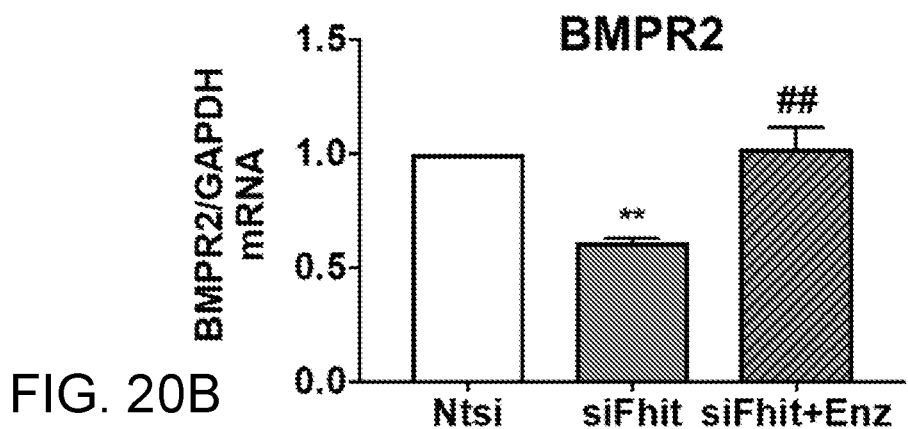
Figure 20C:
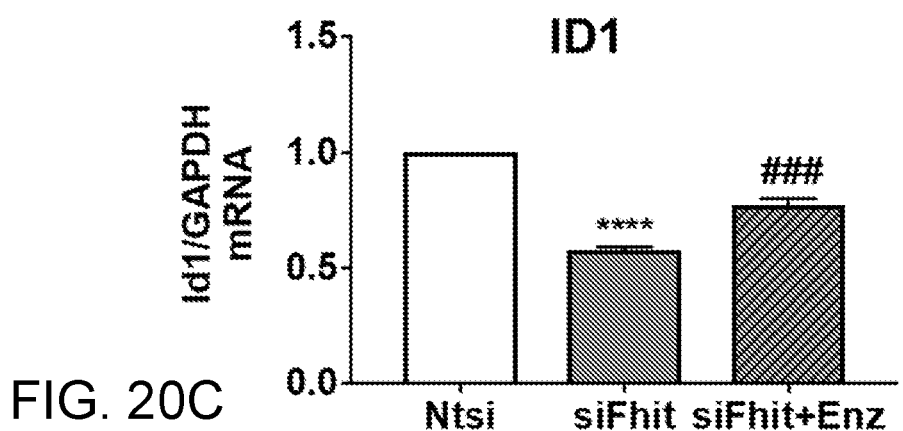

Select, P/N 4392420) 100 nM and then treated with Non-targeting siRNA 100 nM by RNAiMax (Invitrogen) for 48 hours. Cells were then treated with Enzastaurin 15 uM for 24 hours. RNA was isolated by RNeasy® Plus Mini Kit (Qiagen) and analyze Fhit, BMPR2 and Id1 gene expression by Taqman® gene expression assay (Invitrogen. Fhit, BMPR2 and Id1 gene expression was measured using Taqman® gene expression assay). FIG. 20A: Relative expression of FHIT, FIG. 20B: BMPR2, FIG. 20C: ID1. All bars denote Mean±SEM., n=3, One Way ANOVA, Sidack's multi comparison test **$p<0.0001$, $p<0.01$ Ntsi vs siFHIT, ###$p<0.0005$, ## $P<0.01$ siFHIT vs siFHIT+Enz.

Example S10

Reduction of BMPR2 and ID1 in PAEC by FHIT knockdown is in part miR17-5 dependent. Human PAEC were plated on the 6 well plates ($0.5 \times 10^6$ cells/well) and transfected with siFhit (Ambion Silencer® Select, P/N 4392420) 100 nM and anti-miR 17-5 inhibitor (AM12412, Ambion) by RNAiMax for 48 hours. Anti-miR MiRNA inhibitor was used as the negative control (AM17010, Ambion)l. MiRNA was isolated by TaqMan® miRNA ABC purification kit and the isolated miRNA was analyzed using Taqman® MicroRNA assays. Fhit, BMPR2 and Id1 gene expression was measured using Taqman® gene expression assay; data are shown in FIG. 21A: Relative expression of miR17.5; FIG. 21B: FHIT; FIG. 21C: BMPR2; and FIG. 21D: ID1. All bars denote Mean±SEM., n=3, *$p<0.05$, $p<0.01$, *$p<0.001$ vs. Ntsi, One Way ANOVA, Turkey's post-test, #$p<0.05$ vs. NtMir, unpaired Student's t test,

Example S11

WT and FHIT −/− C57BL/6 mice do not develop RV fibrosis following hypoxic treatment. Male Wildtype and FHIT−/− C57BL/6 (C57) mice were housed for three weeks in hypoxic (Hx, 10% $O_2$) conditions and a hypoxia-recovery (Rec, 3 weeks Hx/4 weeks Nx) period for 4 weeks. Representative Trichrome heart histology is shown. Fibrosis is indicated by the blue colour. The RV and LV+Septum had to be separated from each other for weight RV/LV+Septum assessment. See FIG. 22.

Example S12

Figure 23C:
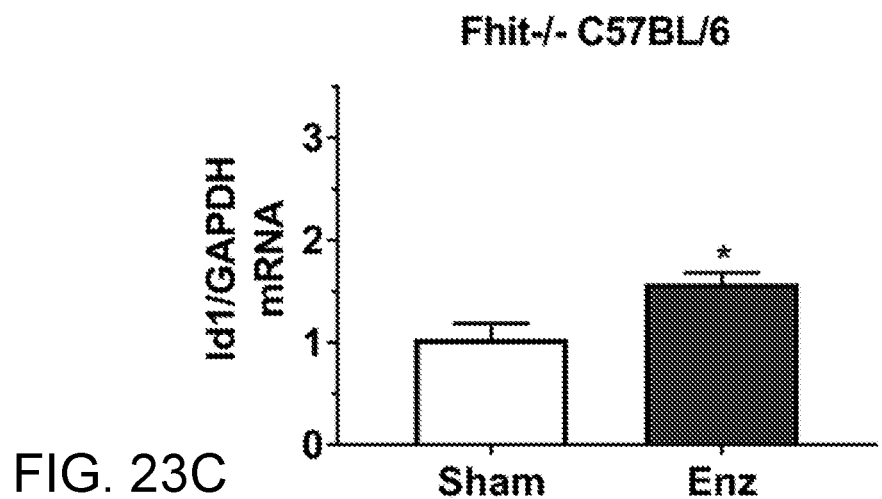

Enzastaurin protects from increased RVSP and up-regulates BMPR2/Id1 mRNA in hypoxia in FHIT −/− mice. Male FHIT−/− C57BL/6 (C57) mice were exposed to three weeks in hypoxic (Hx, 10% $O_2$), treated with Enzastaurin or vehicle (saline) control at a concentration of 5 mg/kg body weight by mini-osmotic pump (Alzet model 2004). See FIG. 23A, Right ventricle systolic pressure (RVSP) was measured by pulmonary artery catheterisation (n=3, Mean±SEM, *$p<0.05$ vs. Sham control, unpaired Student's t test). FIGS. 23B-23C, ΔΔCt analysis of mRNA expression in lung tissue. (n=3, Mean±SEM, *$p<0.05$, **$p<0.01$ vs. Sham control, unpaired Student's t test). Abbreviations: Enz —Enzastaurin

Example S13

Figure 24A:
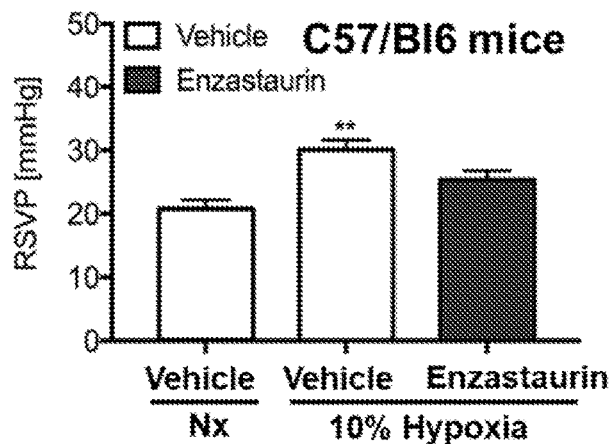
FIGS. 24A-24G: Enzastaurin prevents the development of hypoxia-induced experimental PAH in C57BL/6 mice.
Figure 24B:
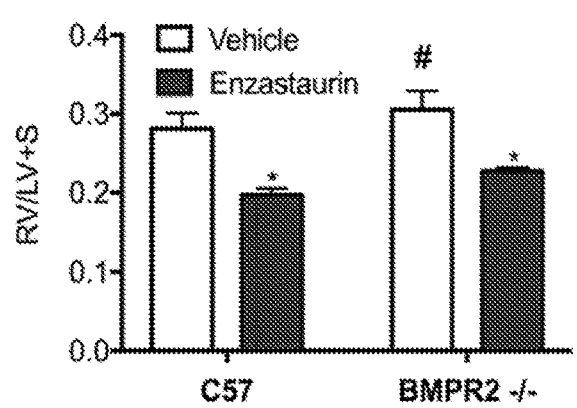
Figure 24C:
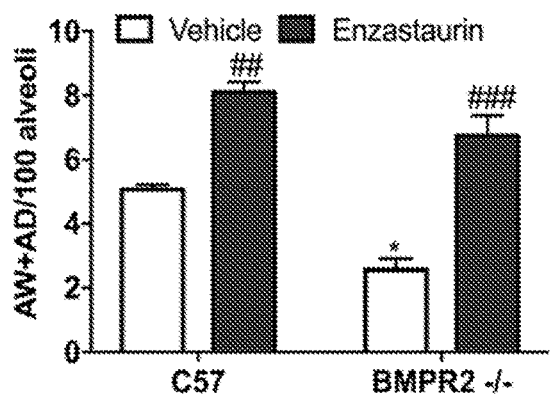
Figure 24D:
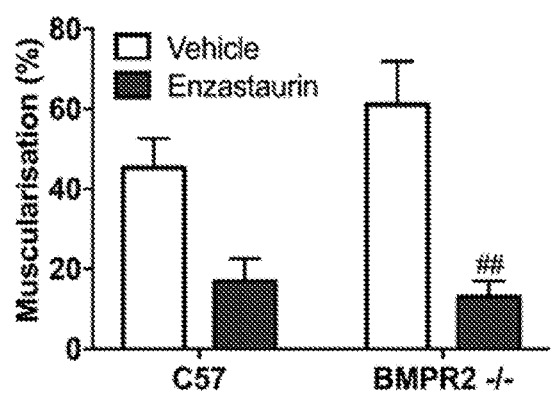
Figure 24E:
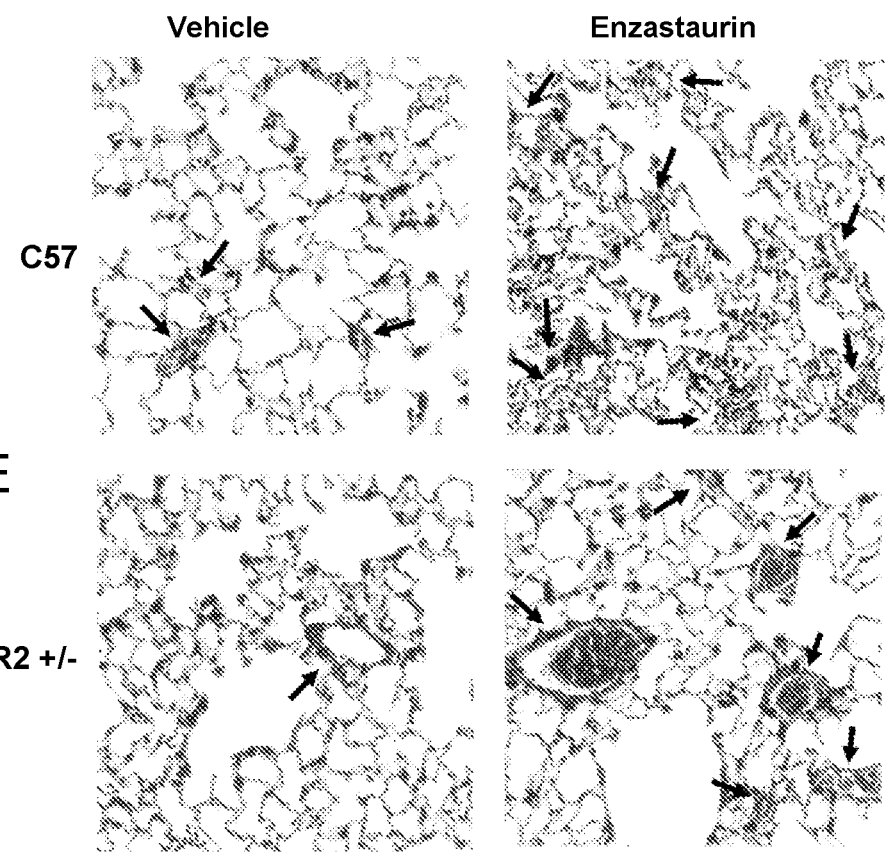
Figure 24F:
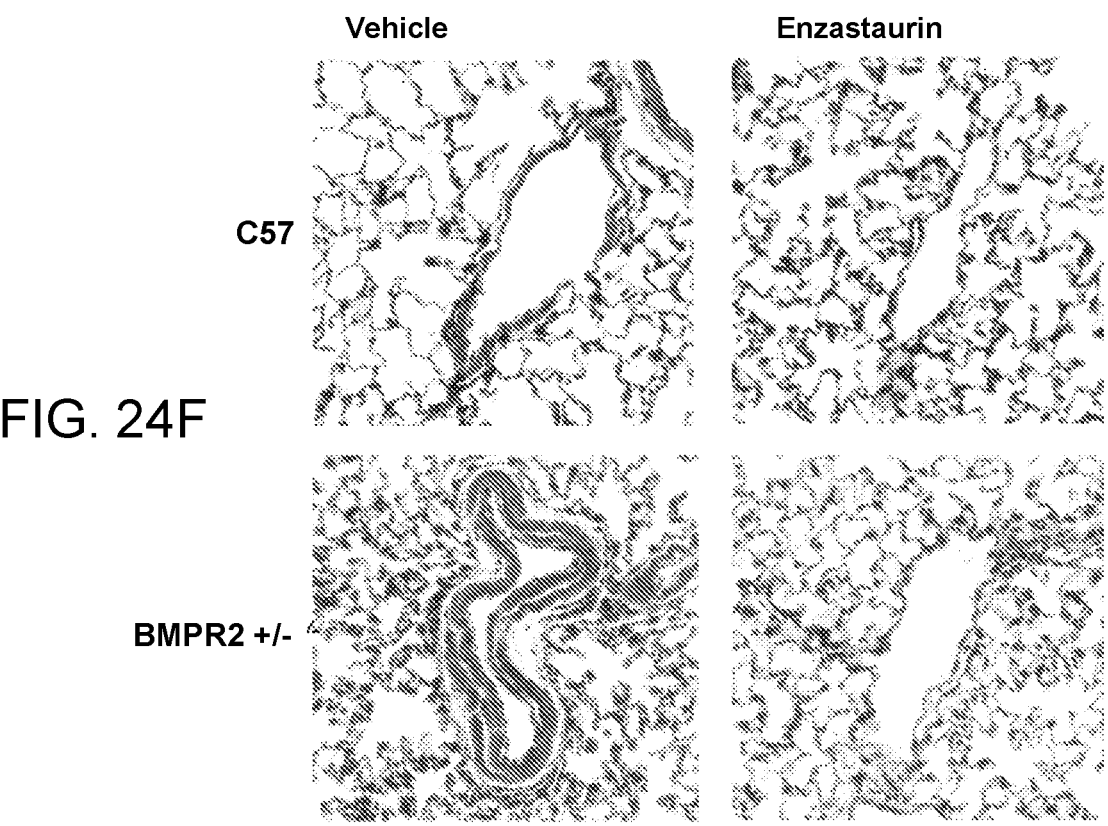
Figure 24G:
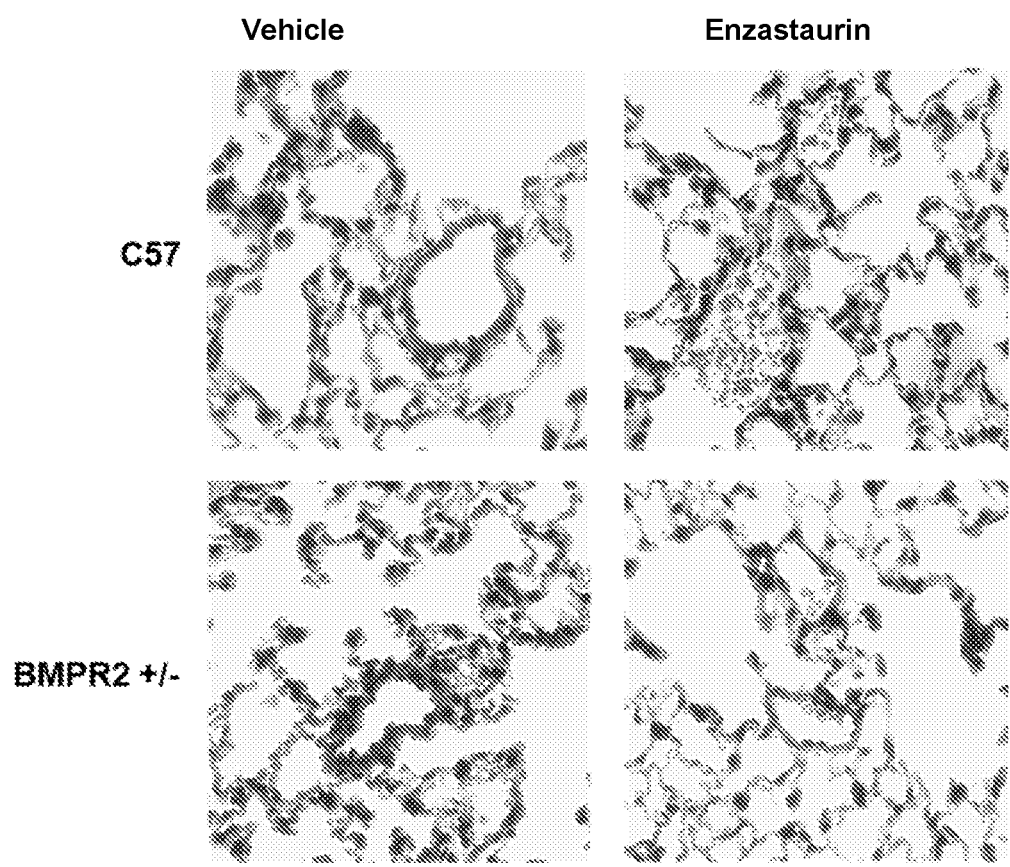

Enzastaurin prevents the development of hypoxia-induced experimental PAH in C57BL/6 mice. Male Wildtype and Bmpr2+/−C57BL/6 (C57) mice were housed for three weeks in normoxic (Nx, 20% $O_2$) and hypoxic (Hx, 10% $O_2$) conditions, treated with or without daily administration of 5 mg/kg Enzastaurin by oral gavage/Alzet mini-osmotic pump model 2006. Data are summarized in FIGS. 24A-24G: FIG. 24A, Right ventricle systolic pressure (RVSP) was measured by pulmonary artery catheterisation (n=3, Mean±SEM, **$p<0.01$ vs. Nx control, One Way ANOVA, Sidak's post-test). FIG. 24B, Right ventricle (RV) hypertrophy is demonstrated by the weight ratio of RV to left ventricle and septum (n=3, Mean±SEM, #$p<0.05$ vs. vehicle control, Two Way ANOVA, Turkey's post-test). FIG. 24C, Loss of alveolar wall (AW) and alveolar duct (AD) pulmonary vessels and FIG. 24D, their full or partial muscularization (%) was assessed in MOVAT stained lung sections (n=3, Mean±SEM, *$p<0.05$ vs. C57 control, ##$p<0.01$, ###$p<0.001$ vs. vehicle control, Two Way ANOVA, Turkey's post-test). FIG. 24E, Representative MOVAT lung histology. Arrows indicate vessel position. FIGS. 24F-24G, Representative MOVAT lung histology of large (FIG. 24F) and small vessels (FIG. 24G) respectively. Arrows indicate vessel position.

Example S14

Figure 25A:
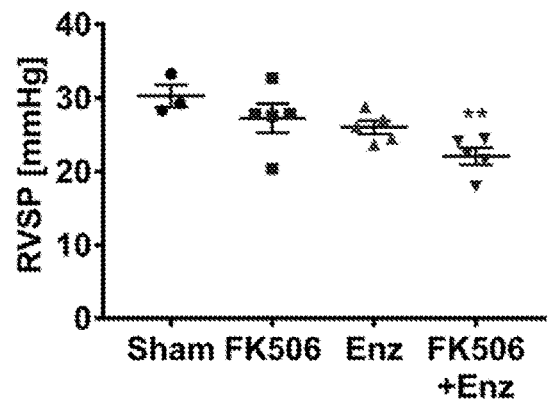
FIGS. 25A-25D: FK506 and Enzastaurin have additional effects on BMPR2/Id1, but not FHIT mRNA in wildtype C57BL/6 mice in hypoxia, protecting from increases in RVSP.
Figure 25B:
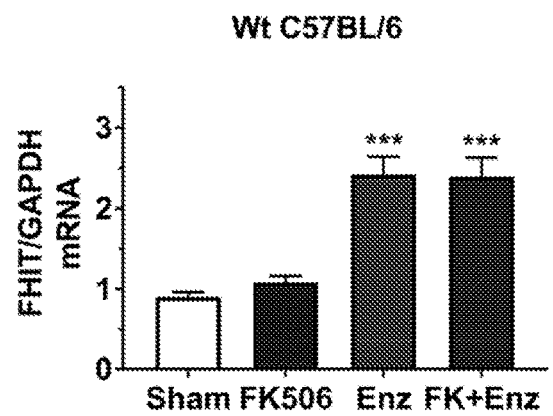
Figure 25C:
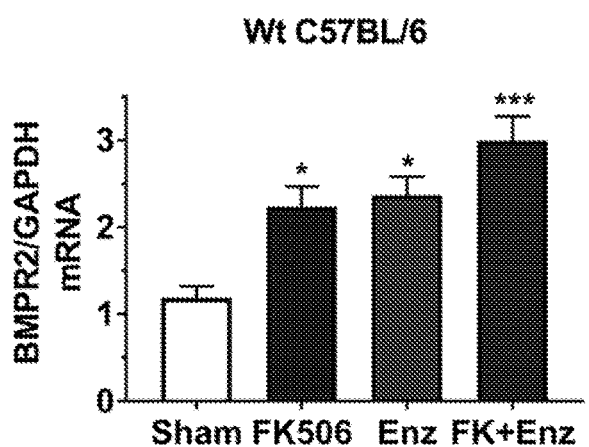
Figure 25D:
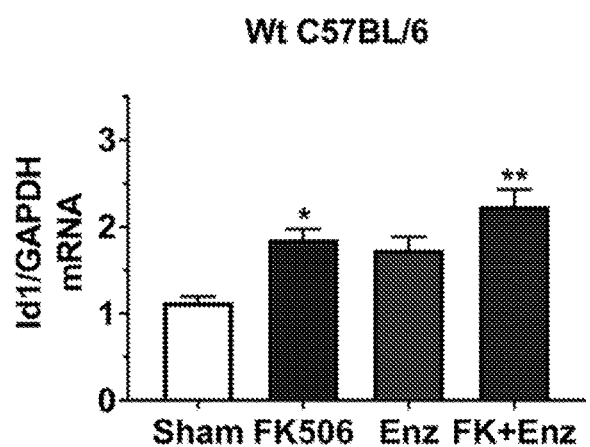

FK506 and Enzastaurin have additional effects on BMPR2/Id1, but not FHIT mRNA in wildtype C57BL/6 mice in hypoxia, protecting from increases in RVSP. Male Wildtype C57BL/6 (C57) mice were exposed to three weeks in hypoxic (Hx, 10% $O_2$), and treated with 5 mg/kg body weight Enzastaurin or vehicle control (saline) with or without 0.05 mg/kg/d FK506 by mini-osmotic pump (Alzet model 2004). Results are depicted in FIGS. 25A-25D: FIG. 25A, Right ventricle systolic pressure (RVSP) was measured by pulmonary artery catheterisation (n=3, Mean±SEM, **$p<0.01$ vs. Sham control, One Way ANOVA, Dunnett's post-test). FIGS. 25B-25D, ΔΔCt analysis of mRNA expression in lung tissue. (n=3, Mean±SEM, *$p<0.05$, $p<0.01$, *$p<0.001$ vs. Sham control, One Way ANOVA, Dunnett's post-test). Abbreviations: FK—FK506, Enz—Enzastaurin.

Example S15

Representative MOVAT lung histology in Sprague Dawley rat lungs, comparing Normoxia and Sugen/Hypoxia conditions after 3 weeks of Enzastaurin treatment.

Figure 26:
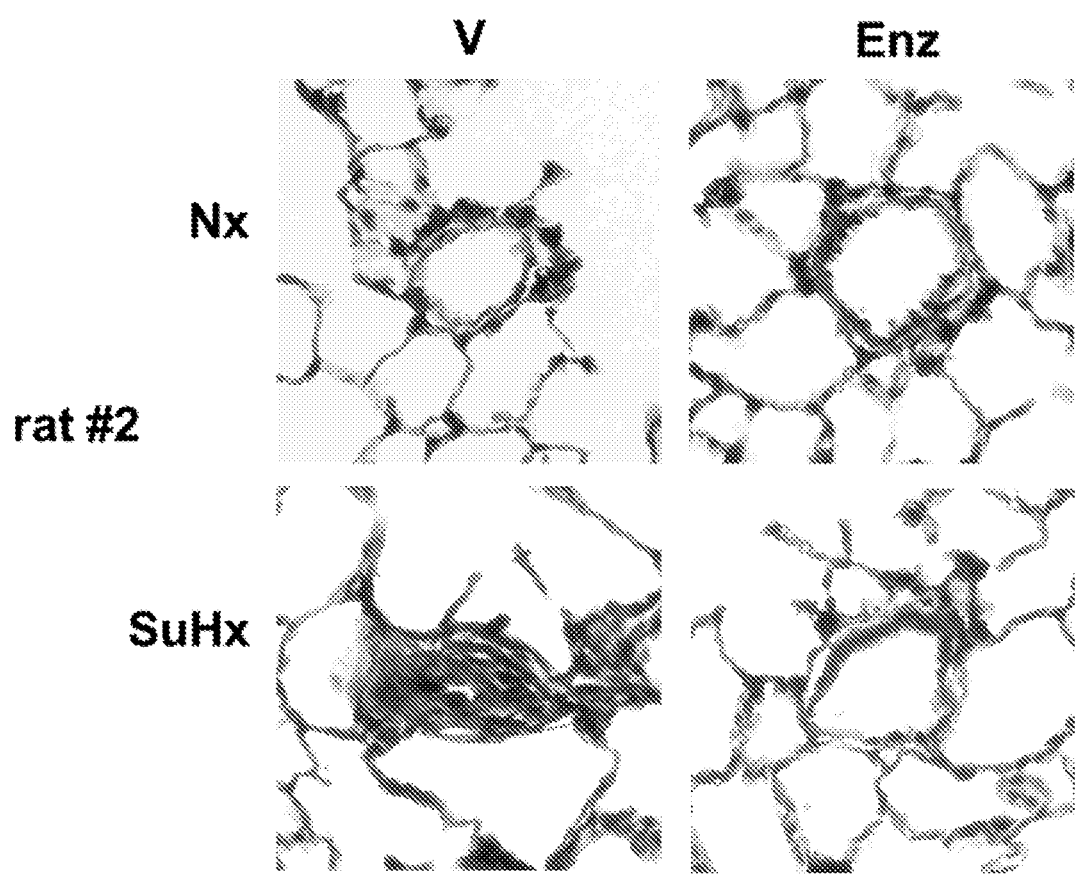
FIG. 26: Representative MOVAT lung histology in Sprague Dawley rat lungs, comparing Normoxia and Sugen/Hypoxia conditions after 3 weeks of Enzastaurin treatment.

Experimental PAH was induced in male Sasco Sprague Dawley rats by subcutaneous injection of 20 mg/kg body weight SU5416. Animals were housed for 3 weeks in hypoxic (Hx, 10% $O_2$) conditions, followed by a 5 week period in normoxia (Nx, 20% $O_2$), following daily administration of 5 mg/kg body weight Enzastaurin or vehicle control by oral gavage. Representative MOVAT lung histology of small pulmonary vessels are shown in FIG. 26.

REFERENCES

1. Austin E D, Loyd J E, Phillips J A. Heritable Pulmonary Arterial Hypertension. In: Pagon R A A M, Ardinger H H, et al., editors., editor. GeneReviews [Internet]. Seattle (Wash.): University of Washington, Seattle; ; 2015.
2. Lane K B, Machado R D, Pauciulo M W, Thomson J R, Phillips J A, Loyd J E, Nichols W C, Trembath R C, Consortium I P. Heterozygous germline mutations in BMPR2, encoding a TGF-beta receptor, cause familial primary pulmonary hypertension. *Nat Genet* 2000; 26: 81-84.
3. Fessel J P, Loyd J E, Austin E D. The genetics of pulmonary arterial hypertension in the post-BMPR2 era. *Pulm Circ* 2011; 1: 305-319.

4. Atkinson C, Stewart S, Upton P D, Machado R, Thomson J R, Trembath R C, Morrell N W. Primary pulmonary hypertension is associated with reduced pulmonary vascular expression of type II bone morphogenetic protein receptor. *Circulation* 2002; 105: 1672-1678.
5. Rich J D, Shah S J, Swamy R S, Kamp A, Rich S. Inaccuracy of Doppler echocardiographic estimates of pulmonary artery pressures in patients with pulmonary hypertension: implications for clinical practice. *Chest* 2011; 139: 988-993.
6. Long L, Ormiston M L, Yang X, Southwood M, Gräf S, Machado R D, Mueller M, Kinzel B, Yung L M, Wilkinson J M, Moore S D, Drake K M, Aldred M A, Yu P B, Upton P D, Morrell N W. Selective enhancement of endothelial BMPR-II with BMP9 reverses pulmonary arterial hypertension. *Nat Med* 2015; 21: 777-785.
7. Long L, Yang X, Southwood M, Lu J, Marciniak S J, Dunmore B J, Morrell N W. Chloroquine prevents progression of experimental pulmonary hypertension via inhibition of autophagy and lysosomal bone morphogenetic protein type II receptor degradation. *Circ Res* 2013; 112: 1159-1170.
8. Brittain E L, Thenappan T, Maron B A, Chan S Y, Austin E D, Spiekerkoetter E, Bogaard H J, Guignabert C, Paulin R, Machado R F, Yu P B. Update in Pulmonary Vascular Disease 2016 and 2017. *Am J Respir Crit Care Med* 2018.
9. Liu D, Yan Y, Chen J W, Yuan P, Wang X J, Jiang R, Wang L, Zhao Q H, Wu W H, Simonneau G, Qu J M, Jing Z C. Hypermethylation of BMPR2 Promoter Occurs in Patients with Heritable Pulmonary Arterial Hypertension and Inhibits BMPR2 Expression. *Am J Respir Crit Care Med* 2017; 196: 925-928.
10. Spiekerkoetter E, Sung Y K, Sudheendra D, Scott V, Del Rosario P, Bill M, Haddad F, Long-Boyle J, Hedlin H, Zamanian R T. Randomised placebo-controlled safety and tolerability trial of FK506 (tacrolimus) for pulmonary arterial hypertension. *Eur Respir J* 2017; 50.
11. Spiekerkoetter E, Sung Y K, Sudheendra D, Bill M, Aldred M A, van de Veerdonk M C, Vonk Noordegraaf A, Long-Boyle J, Dash R, Yang P C, Lawrie A, Swift A J, Rabinovitch M, Zamanian R T. Low-Dose FK506 (Tacrolimus) in End-Stage Pulmonary Arterial Hypertension. *Am J Respir Crit Care Med* 2015; 192: 254-257.
12. Spiekerkoetter E, Tian X, Cai J, Hopper R K, Sudheendra D, Li C G, El-Bizri N, Sawada H, Haghighat R, Chan R, Haghighat L, de Jesus Perez V, Wang L, Reddy S, Zhao M, Bernstein D, Solow-Cordero D E, Beachy P A, Wandless T J, Ten Dijke P, Rabinovitch M. FK506 activates BMPR2, rescues endothelial dysfunction, and reverses pulmonary hypertension. *J Clin Invest* 2013; 123: 3600-3613.
13. Huebner K, Garrison P N, Barnes L D, Croce C M. The role of the FHIT/FRA3B locus in cancer. *Annu Rev Genet* 1998; 32: 7-31.
14. Sozzi G, Sard L, De Gregorio L, Marchetti A, Musso K, Buttitta F, Tornielli S, Pellegrini S, Veronese M L, Manenti G, Incarbone M, Chella A, Angeletti C A, Pastorino U, Huebner K, Bevilaqua G, Pilotti S, Croce C M, Pierotti M A. Association between cigarette smoking and FHIT gene alterations in lung cancer. *Cancer Res* 1997; 57: 2121-2123.
15. Thavathiru E, Ludes-Meyers J H, MacLeod M C, Aldaz C M. Expression of common chromosomal fragile site genes, WWOX/FRA16D and FHIT/FRA3B is downregulated by exposure to environmental carcinogens, UV, and BPDE but not by IR. *Mol Carcinog* 2005; 44: 174-182.
16. Kujan O, Abuderman A, Al-Shawaf A Z. Immunohistochemical characterization of FHIT expression in normal human tissues. *Interv Med Appl Sci* 2016; 8: 7-13.
17. Sozzi G, Pastorino U, Moiraghi L, Tagliabue E, Pezzella F, Ghirelli C, Tornielli S, Sard L, Huebner K, Pierotti M A, Croce C M, Pilotti S. Loss of FHIT function in lung cancer and preinvasive bronchial lesions. *Cancer Res* 1998; 58: 5032-5037.
18. Campiglio M, Pekarsky Y, Menard S, Tagliabue E, Pilotti S, Croce C M. FHIT loss of function in human primary breast cancer correlates with advanced stage of the disease. *Cancer Res* 1999; 59: 3866-3869.
19. Toledo G, Sola J J, Lozano M D, Soria E, Pardo J. Loss of FHIT protein expression is related to high proliferation, low apoptosis and worse prognosis in non-small-cell lung cancer. *Mod Pathol* 2004; 17: 440-448.
20. Huang Q, Liu Z, Xie F, Liu C, Shao F, Zhu C L, Hu S. Fragile histidine triad (FHIT) suppresses proliferation and promotes apoptosis in cholangiocarcinoma cells by blocking PI3K-Akt pathway. *Scientific World Journal* 2014; 2014: 179698.
21. Robertson M J, Kahl B S, Vose J M, de Vos S, Laughlin M, Flynn P J, Rowland K, Cruz J C, Goldberg S L, Musib L, Darstein C, Enas N, Kutok J L, Aster J C, Neuberg D, Savage K J, LaCasce A, Thornton D, Slapak C A, Shipp M A. Phase II study of enzastaurin, a protein kinase C beta inhibitor, in patients with relapsed or refractory diffuse large B-cell lymphoma. *J Clin Oncol* 2007; 25: 1741-1746.
22. Dannewitz Prosseda S, Suheendra D, Tian X, Kung J, Bohm M, Kumamoto K, Solow-Cordero D, Saldivar J, Austin E, Loyd J E, Huber K, Khatri, Purvesh., Spiekerkoetter E. Enzastaurin Reverses Pulmonary Arterial Hypertension by Targeting the Novel BMPR2 Modifier FHIT. ATS Conference. Washington D.C.: American Journal of Respiratory and Critical Care Medicine; 2017. p. A4228.
23. Austin E D, Hamid R, Hemnes A R, Loyd J E, Blackwell T, Yu C, Phillips Iii J A, Gaddipati R, Gladson S, Gu E, West J, Lane K B. BMPR2 expression is suppressed by signaling through the estrogen receptor. *Biol Sex Differ* 2012; 3: 6.
24. Khatri P, Roedder S, Kimura N, De Vusser K, Morgan A A, Gong Y, Fischbein M P, Robbins R C, Naesens M, Butte A J, Sarwal M M. A common rejection module (CRM) for acute rejection across multiple organs identifies novel therapeutics for organ transplantation. *J Exp Med* 2013; 210: 2205-2221.
25. Sweeney T E, Haynes W A, Vallania F, Ioannidis J P, Khatri P. Methods to increase reproducibility in differential gene expression via meta-analysis. *Nucleic Acids Res* 2017; 45: el.
26. Li M D, Burns T C, Morgan A A, Khatri P. Integrated multi-cohort transcriptional meta-analysis of neurodegenerative diseases. *Acta Neuropathol Commun* 2014; 2: 93.
27. Lee K C, Ouwehand I, Giannini A L, Thomas N S, Dibb N J, Bijlmakers M J. Lck is a key target of imatinib and dasatinib in T-cell activation. *Leukemia* 2010; 24: 896-900.
28. Montani D, Bergot E, Günther S, Savale L, Bergeron A, Bourdin A, Bouvaist H, Canuet M, Pison C, Macro M, Poubeau P, Girerd B, Natali D, Guignabert C, Perros F, O'Callaghan D S, Jaïs X, Tubert-Bitter P, Zalcman G, Sitbon O, Simonneau G, Humbert M. Pulmonary arterial hypertension in patients treated by dasatinib. *Circulation* 2012; 125: 2128-2137.

29. Hamid R, Cogan J D, Hedges L K, Austin E, Phillips J A, Newman J H, Loyd J E. Penetrance of pulmonary arterial hypertension is modulated by the expression of normal BMPR2 allele. *Hum Mutat* 2009; 30: 649-654.
30. Drake K M, Zygmunt D, Mavrakis L, Harbor P, Wang L, Comhair S A, Erzurum S C, Aldred M A. Altered MicroRNA processing in heritable pulmonary arterial hypertension: an important role for Smad-8. *Am J Respir Crit Care Med* 2011; 184: 1400-1408.
31. Caruso P, MacLean M R, Khanin R, McClure J, Soon E, Southgate M, MacDonald R A, Greig J A, Robertson K E, Masson R, Denby L, Dempsie Y, Long L, Morrell N W, Baker A H. Dynamic changes in lung microRNA profiles during the development of pulmonary hypertension due to chronic hypoxia and monocrotaline. *Arterioscler Thromb Vasc Biol* 2010; 30: 716-723.
32. Thompson A A, Lawrie A. Targeting Vascular Remodeling to Treat Pulmonary Arterial Hypertension. *Trends Mol Med* 2017; 23: 31-45.
33. Hislop A, Reid L. New findings in pulmonary arteries of rats with hypoxia-induced pulmonary hypertension. *Br J Exp Pathol* 1976; 57: 542-554.
34. Meloche J, Pflieger A, Vaillancourt M, Paulin R, Potus F, Zervopoulos S, Graydon C, Courboulin A, Breuils-Bonnet S, Tremblay E, Couture C, Michelakis E D, Provencher S, Bonnet S. Role for DNA damage signaling in pulmonary arterial hypertension. *Circulation* 2014; 129: 786-797.
35. Federici C, Drake K M, Rigelsky C M, McNelly L N, Meade S L, Comhair S A, Erzurum S C, Aldred M A. Increased Mutagen Sensitivity and DNA Damage in Pulmonary Arterial Hypertension. *Am J Respir Crit Care Med* 2015; 192: 219-228.
36. de Jesus Perez V A, Alastalo T P, Wu J C, Axelrod J D, Cooke J P, Amieva M, Rabinovitch M. Bone morphogenetic protein 2 induces pulmonary angiogenesis via Wnt-beta-catenin and Wnt-RhoA-Rac1 pathways. *J Cell Biol* 2009; 184: 83-99.
37. Chen P I, Cao A, Miyagawa K, Tojais N F, Hennigs J K, Li C G, Sweeney N M, Inglis A S, Wang L, Li D, Ye M, Feldman B J, Rabinovitch M. Amphetamines promote mitochondrial dysfunction and DNA damage in pulmonary hypertension. *JCI Insight* 2017; 2: e90427.
38. Fong L Y, Fidanza V, Zanesi N, Lock L F, Siracusa L D, Mancini R, Siprashvili Z, Ottey M, Martin S E, Druck T, McCue P A, Croce C M, Huebner K. Muir-Torre-like syndrome in Fhit-deficient mice. *Proc Natl Acad Sci USA* 2000; 97: 4742-4747.
39. Zanesi N, Fidanza V, Fong L Y, Mancini R, Druck T, Valtieri M, Rtidiger T, McCue P A, Croce C M, Huebner K. The tumor spectrum in FHIT-deficient mice. *Proc Natl Acad Sci USA* 2001; 98: 10250-10255.
40. Metzger R J, Klein O D, Martin G R, Krasnow M A. The branching programme of mouse lung development. *Nature* 2008; 453: 745-750.
41. Abe K, Toba M, Alzoubi A, Ito M, Fagan K A, Cool C D, Voelkel N F, McMurtry I F, Oka M. Formation of plexiform lesions in experimental severe pulmonary arterial hypertension. *Circulation* 2010; 121: 2747-2754.
42. Meyrick B O, Friedman D B, Billheimer D D, Cogan J D, Prince M A, Phillips J A, Loyd J E. Proteomics of transformed lymphocytes from a family with familial pulmonary arterial hypertension. *Am J Respir Crit Care Med* 2008; 177: 99-107.
43. Gu M, Shao N Y, Sa S, Li D, Termglinchan V, Ameen M, Karakikes I, Sosa G, Grubert F, Lee J, Cao A, Taylor S, Ma Y, Zhao Z, Chappell J, Hamid R, Austin E D, Gold J D, Wu J C, Snyder M P, Rabinovitch M. Patient-Specific iPSC-Derived Endothelial Cells Uncover Pathways that Protect against Pulmonary Hypertension in BMPR2 Mutation Carriers. *Cell Stem Cell* 2017; 20: 490-504.e495.
44. Nicolls M R, Taraseviciene-Stewart L, Rai P R, Badesch D B, Voelkel N F. Autoimmunity and pulmonary hypertension: a perspective. *Eur Respir J* 2005; 26: 1110-1118.
45. Rabinovitch M, Guignabert C, Humbert M, Nicolls M R. Inflammation and immunity in the pathogenesis of pulmonary arterial hypertension. *Circ Res* 2014; 115: 165-175.
46. Hemnes A R, Trammell A W, Archer S L, Rich S, Yu C, Nian H, Penner N, Funke M, Wheeler L, Robbins I M, Austin E D, Newman J H, West J. Peripheral blood signature of vasodilator-responsive pulmonary arterial hypertension. *Circulation* 2015; 131: 401-409; discussion 409.
47. Silva Soares E W, de Lima Santos S C, Bueno A G, Cavalli I J, Cavalli L R, Fouto Matias J E, de Souza Fonseca Ribeiro E M. Concomitant loss of heterozygosity at the BRCA1 and FHIT genes as a prognostic factor in sporadic breast cancer. *Cancer Genet Cytogenet* 2010; 199: 24-30.
48. Andriani F, Roz E, Caserini R, Conte D, Pastorino U, Sozzi G, Roz L. Inactivation of both FHIT and p53 cooperate in deregulating proliferation-related pathways in lung cancer. *J Thorac Oncol* 2012; 7: 631-642.
49. Pekarsky Y, Zanesi N, Palamarchuk A, Huebner K, Croce C M. FHIT: from gene discovery to cancer treatment and prevention. *Lancet Oncol* 2002; 3: 748-754.
50. Paisie C A, Schrock M S, Karras J R, Zhang J, Miuma S, Ouda I M, Waters C E, Saldivar J C, Druck T, Huebner K. Exome-wide single-base substitutions in tissues and derived cell lines of the constitutive Fhit knockout mouse. *Cancer Sci* 2016; 107: 528-535.
51. Schiess R, Senn O, Fischler M, Huber L C, Vatandaslar S, Speich R, Ulrich S. Tobacco smoke: a risk factor for pulmonary arterial hypertension? A case-control study. *Chest* 2010; 138: 1086-1092.
52. Huebner K, Croce C M. FRA3B and other common fragile sites: the weakest links. *Nat Rev Cancer* 2001; 1: 214-221.
53. Yoo Y G, Christensen J, Huang L E. HIF-1α confers aggressive malignant traits on human tumor cells independent of its canonical transcriptional function. *Cancer Res* 2011; 71: 1244-1252.
54. Michael D, Rajewsky M F. Induction of the common fragile site FRA3B does not affect FHIT expression. *Oncogene* 2001; 20: 1798-1801.
55. Jacquin S, Rincheval V, Mignotte B, Richard S, Humbert M, Mercier O, Londofio-Vallejo A, Fadel E, Eddahibi S. Inactivation of p53 Is Sufficient to Induce Development of Pulmonary Hypertension in Rats. *PLoS One* 2015; 10: e0131940.
56. Yan W, Xu N, Han X, Zhou X M, He B. The clinico-pathological significance of FHIT hypermethylation in non-small cell lung cancer, a meta-analysis and literature review. *Sci Rep* 2016; 6: 19303.
57. Wali A. FHIT: doubts are clear now. *ScientificWorldJournal* 2010; 10: 1142-1151.
58. Guler G, Iliopoulos D, Han S Y, Fong L Y, Lubet R A, Grubbs C J, Huebner K. Hypermethylation patterns in the Fhit regulatory region are tissue specific. *Mol Carcinog* 2005; 43: 175-181.
59. Tanaka H, Shimada Y, Harada H, Shinoda M, Hatooka S, Imamura M, Ishizaki K. Methylation of the 5' CpG 59. island of the FHIT gene is closely associated with transcriptional inactivation in esophageal squamous cell carcinomas. *Cancer Res* 1998; 58: 3429-3434.
60. Zöchbauer-Muiller S, Fong K M, Maitra A, Lam S, Geradts J, Ashfaq R, Virmani A K, Milchgrub S, Gazdar A F, Minna J D. 5' CpG island methylation of the FHIT gene is correlated with loss of gene expression in lung and breast cancer. *Cancer Res* 2001; 61: 3581-3585.
61. Yang Q, Nakamura M, Nakamura Y, Yoshimura G, Suzuma T, Umemura T, Shimizu Y, Mori I, Sakurai T, Kakudo K. Two-hit inactivation of FHIT by loss of heterozygosity and hypermethylation in breast cancer. *Clin Cancer Res* 2002; 8: 2890-2893.
62. Dhillon V S, Shahid M, Husain S A. CpG methylation of the FHIT, FANCF, cyclin-D2, BRCA2 and RUNX3 genes in Granulosa cell tumors (GCTs) of ovarian origin. *Mol Cancer* 2004; 3: 33.
63. Kim J S, Kim H, Shim Y M, Han J, Park J, Kim D H. Aberrant methylation of the FHIT gene in chronic smokers with early stage squamous cell carcinoma of the lung. *Carcinogenesis* 2004; 25: 2165-2171.
64. Körner A, Mudduluru G, Manegold C, Allgayer H. Enzastaurin inhibits invasion and metastasis in lung cancer by diverse molecules. *Br J Cancer* 2010; 103: 802-811.
65. Zeng Y, Qu X, Li H, Huang S, Wang S, Xu Q, Lin R, Han Q, Li J, Zhao R C. MicroRNA-100 regulates osteogenic differentiation of human adipose-derived mesenchymal stem cells by targeting BMPR2. *FEBS Lett* 2012; 586: 2375-2381.
66. Sun Q, Mao S, Li H, Zen K, Zhang C Y, Li L. Role of miR-17 family in the negative feedback loop of bone morphogenetic protein signaling in neuron. *PLoS One* 2013; 8: e83067.
67. Brock M, Trenkmann M, Gay R E, Michel B A, Gay S, Fischler M, Ulrich S, Speich R, Huber L C. Interleukin-6 modulates the expression of the bone morphogenic protein receptor type II through a novel STAT3-microRNA cluster 17/92 pathway. *Circ Res* 2009; 104: 1184-1191.
68. Hansmann G, de Jesus Perez V A, Alastalo T P, Alvira C M, Guignabert C, Bekker J M, Schellong S, Urashima T, Wang L, Morrell N W, Rabinovitch M. An antiproliferative BMP-2/PPARgamma/apoE axis in human and murine SMCs and its role in pulmonary hypertension. *J Clin Invest* 2008; 118: 1846-1857.
69. Brock M, Samillan V J, Trenkmann M, Schwarzwald C, Ulrich S, Gay R E, Gassmann M, Ostergaard L, Gay S, Speich R, Huber L C. AntagomiR directed against miR-20a restores functional BMPR2 signalling and prevents vascular remodelling in hypoxia-induced pulmonary hypertension. *Eur Heart J* 2014; 35: 3203-3211.
70. Diebold I, Hennigs J K, Miyagawa K, Li C G, Nickel N P, Kaschwich M, Cao A, Wang L, Reddy S, Chen P I, Nakahira K, Alcazar M A, Hopper R K, Ji L, Feldman B J, Rabinovitch M. BMPR2 preserves mitochondrial function and DNA during reoxygenation to promote endothelial cell survival and reverse pulmonary hypertension. *Cell Metab* 2015; 21: 596-608.
71. Rabinovitch M. Molecular pathogenesis of pulmonary arterial hypertension. J Clin Invest 2012; 122: 4306-4313.
72. Aldred M A, Comhair S A, Varella-Garcia M, Asosingh K, Xu W, Noon G P, Thistlethwaite P A, Tuder R M, Erzurum S C, Geraci M W, Coldren C D. Somatic chromosome abnormalities in the lungs of patients with pulmonary arterial hypertension. *Am J Respir Crit Care Med* 2010; 182: 1153-1160.
73. Cirombella R, Montrone G, Stoppacciaro A, Giglio S, Volinia S, Graziano P, Huebner K, Vecchione A. Fhit loss in lung preneoplasia: relation to DNA damage response checkpoint activation. *Cancer Lett* 2010; 291: 230-236.
74. Drake K M, Dunmore B J, McNelly L N, Morrell N W, Aldred M A. Correction of nonsense BMPR2 and SMAD9 mutations by ataluren in pulmonary arterial hypertension. *Am J Respir Cell Mol Biol* 2013; 49: 403-409.
75. Betapudi V, Shukla M, Alluri R, Merkulov S, McCrae K R. Novel role for p56/Lck in regulation of endothelial cell survival and angiogenesis. *FASEB J* 2016; 30: 3515-3526.
76. Joannes A, Grelet S, Duca L, Gilles C, Kileztky C, Dalstein V, Birembaut P, Polette M, Nawrocki-Raby B. Fhit regulates EMT targets through an EGFR/Src/ERK/Slug signaling axis in human bronchial cells. *Mol Cancer Res* 2014; 12: 775-783.
77. Joannes A, Bonnomet A, Bindels S, Polette M, Gilles C, Burlet H, Cutrona J, Zahm J M, Birembaut P, Nawrocki-Raby B. Fhit regulates invasion of lung tumor cells. *Oncogene* 2010; 29: 1203-1213.
78. Suh S S, Yoo J Y, Cui R, Kaur B, Huebner K, Lee T K, Aqeilan R I, Croce C M. FHIT suppresses epithelial-mesenchymal transition (EMT) and metastasis in lung cancer through modulation of microRNAs. *PLoS Genet* 2014; 10: e1004652.
79. Smadja D M, Mauge L, Sanchez O, Silvestre J S, Guerin C, Godier A, Henno P, Gaussem P, Israel-Biet D. Distinct patterns of circulating endothelial cells in pulmonary hypertension. *Eur Respir J* 2010; 36: 1284-1293.
80. Vitali S H, Hansmann G, Rose C, Fernandez-Gonzalez A, Scheid A, Mitsialis S A, Kourembanas S. The Sugen 5416/hypoxia mouse model of pulmonary hypertension revisited: long-term follow-up. *Pulm Circ* 2014; 4: 619-629.
81. Gomez-Arroyo J G, Farkas L, Alhussaini A A, Farkas D, Kraskauskas D, Voelkel N F, Bogaard H J. The monocrotaline model of pulmonary hypertension in perspective. *Am J Physiol Lung Cell Mol Physiol* 2012; 302: L363-369.
82. Dean A, Nilsen M, Loughlin L, Salt I P, MacLean M R. Metformin Reverses Development of Pulmonary Hypertension via Aromatase Inhibition. *Hypertension* 2016; 68: 446-454.
83. Savai R, Al-Tamari H M, Sedding D, Kojonazarov B, Muecke C, Teske R, Capecchi M R, Weissmann N, Grimminger F, Seeger W, Schermuly R T, Pullamsetti S S. Pro-proliferative and inflammatory signaling converge on FoxO1 transcription factor in pulmonary hypertension. *Nat Med* 2014; 20: 1289-1300.
84. Nwankwo N, Zhang Z, Wang T, Collins C, Resta L, Ermisch S, Day J, Decker R, Kornberg L, Nicol S, Thornton D, Armstrong D K, Carducci M A. Phase I study of enzastaurin and bevacizumab in patients with advanced cancer: safety, efficacy and pharmacokinetics. *Invest New Drugs* 2013; 31: 653-660.
85. Schmidinger M, Szczylik C, Sternberg C N, Kania M, Kelly C S, Decker R, Hamid O, Faelker T, Escudier B. Dose escalation and pharmacokinetics study of enzastaurin and sunitinib versus placebo and sunitinib in patients with metastatic renal cell carcinoma. *Am J Clin Oncol* 2012; 35: 493-497.
86. Teicher B A, Alvarez E, Menon K, Esterman M A, Considine E, Shih C, Faul M M. Antiangiogenic effects of a protein kinase Cbeta-selective small molecule. *Cancer Chemother Pharmacol* 2002; 49: 69-77.

87. Podar K, Raab M S, Zhang J, McMillin D, Breitkreutz I, Tai Y T, Lin B K, Munshi N, Hideshima T, Chauhan D, Anderson K C. Targeting PKC in multiple myeloma: in vitro and in vivo effects of the novel, orally available small-molecule inhibitor enzastaurin (LY317615.HCl). *Blood* 2007; 109: 1669-1677.

88. Bianchi F, Magnifico A, Olgiati C, Zanesi N, Pekarsky Y, Tagliabue E, Croce C M, Menard S, Campiglio M. FHIT-proteasome degradation caused by mitogenic stimulation of the EGF receptor family in cancer cells. *Proc Natl Acad Sci USA* 2006; 103: 18981-18986.

89. Pichiorri F, Okumura H, Nakamura T, Garrison P N, Gasparini P, Suh S S, Druck T, McCorkell K A, Barnes L D, Croce C M, Huebner K. Correlation of fragile histidine triad (Fhit) protein structural features with effector interactions and biological functions. *J Biol Chem* 2009; 284: 1040-1049.

90. Hao et al., Cell Communication and Signaling, 11(1):59, August 2013.

E1. Spiekerkoetter E, Tian X, Cai J, Hopper R K, Sudheendra D, Li C G, El-Bizri N, Sawada H, Haghighat R, Chan R, Haghighat L, de Jesus Perez V, Wang L, Reddy S, Zhao M, Bernstein D, Solow-Cordero D E, Beachy P A, Wandless T J, Ten Dijke P, Rabinovitch M. FK506 activates BMPR2, rescues endothelial dysfunction, and reverses pulmonary hypertension. *J Clin Invest* 2013; 123: 3600-3613.

E2. Chen R, Khatri P, Mazur P K, Polin M, Zheng Y, Vaka D, Hoang C D, Shrager J, Xu Y, Vicent S, Butte A J, Sweet-Cordero E A. A meta-analysis of lung cancer gene expression identifies PTK7 as a survival gene in lung adenocarcinoma. *Cancer Res* 2014; 74: 2892-2902.

E3. Khatri P, Roedder S, Kimura N, De Vusser K, Morgan A A, Gong Y, Fischbein M P, Robbins R C, Naesens M, Butte A J, Sarwal M M. A common rejection module (CRM) for acute rejection across multiple organs identifies novel therapeutics for organ transplantation. *J Exp Med* 2013; 210: 2205-2221.

E4. Li M D, Burns T C, Morgan A A, Khatri P. Integrated multi-cohort transcriptional meta-analysis of neurodegenerative diseases. *Acta Neuropathol Commun* 2014; 2: 93.

E5. Lee K C, Ouwehand I, Giannini A L, Thomas N S, Dibb N J, Bijlmakers M J. Lck is a key target of imatinib and dasatinib in T-cell activation. *Leukemia* 2010; 24: 896-900.

E6. Drăghici S, Sellamuthu S, Khatri P. Babel's tower revisited: a universal resource for cross-referencing across annotation databases. *Bioinformatics* 2006; 22: 2934-2939.

E7. Benjamini Y, Drai D, Elmer G, Kafkafi N, Golani I. Controlling the false discovery rate in behavior genetics research. *Behav Brain Res* 2001; 125: 279-284.

E8. Spiekerkoetter E, Sung Y K, Sudheendra D, Scott V, Del Rosario P, Bill M, Haddad F, Long-Boyle J, Hedlin H, Zamanian R T. Randomised placebo-controlled safety and tolerability trial of FK506 (tacrolimus) for pulmonary arterial hypertension. *Eur Respir J* 2017; 50.

E9. Chen P I, Cao A, Miyagawa K, Tojais N F, Hennigs J K, Li C G, Sweeney N M, Inglis A S, Wang L, Li D, Ye M, Feldman B J, Rabinovitch M. Amphetamines promote mitochondrial dysfunction and DNA damage in pulmonary hypertension. *JCI Insight* 2017; 2: e90427.

E10. Metzger R J, Klein O D, Martin G R, Krasnow M A. The branching programme of mouse lung development. *Nature* 2008; 453: 745-750.

E11. Sheikh A Q, Misra A, Rosas I O, Adams R H, Greif D M. Smooth muscle cell progenitors are primed to muscularize in pulmonary hypertension. *Sci Transl Med* 2015; 7: 308ra159.

E12. Austin E D, Lahm T, West J, Tofovic S P, Johansen A K, Maclean M R, Alzoubi A, Oka M. Gender, sex hormones and pulmonary hypertension. *Pulm Circ* 2013; 3: 294-314.

E13. Hansmann G, Wagner R A, Schellong S, Perez V A, Urashima T, Wang L, Sheikh A Y, Suen R S, Stewart D J, Rabinovitch M. Pulmonary arterial hypertension is linked to insulin resistance and reversed by peroxisome proliferator-activated receptor-gamma activation. *Circulation* 2007; 115: 1275-1284.

E14. Said S I, Hamidi S A, Dickman K G, Szema A M, Lyubsky S, Lin R Z, Jiang Y P, Chen J J, Waschek J A, Kort S. Moderate pulmonary arterial hypertension in male mice lacking the vasoactive intestinal peptide gene. *Circulation* 2007; 115: 1260-1268.

E15. Dempsie Y, MacLean M R. The influence of gender on the development of pulmonary arterial hypertension. *Exp Physiol* 2013; 98: 1257-1261.

E16. Czarnecka K H, Migdalska-Sęk M, Domańska D, Pastuszak-Lewandoska D, Dutkowska A, Kordiak J, Nawrot E, Kiszalkiewicz J, Antczak A, Brzeziafiska-Lasota E. FHIT promoter methylation status, low protein and high mRNA levels in patients with non-small cell lung cancer. *Int J Oncol* 2016; 49: 1175-1184.

E17. Zheng H, Tsuneyama K, Takahashi H, Miwa S, Nomoto K, Saito H, Masuda S, Takano Y. Expression of PTEN and FHIT is involved in regulating the balance between apoptosis and proliferation in lung carcinomas. *Anticancer Res* 2007; 27: 575-581.

E18. Pugh M E, Hemnes A R. Pulmonary hypertension in women. *Expert Rev Cardiovasc Ther* 2010; 8: 1549-1558.

E19. Rabelo R A, Antunes L M, Etchebehere R M, Nomelini R S, Nascentes G A, Murta E F, Pedrosa A L. Loss of heterozygosity in the fragile histidine triad (FHIT) locus and expression analysis of FHIT protein in patients with breast disorders. *Clin Exp Obstet Gynecol* 2013; 40: 89-94.

The invention claimed is:

1. A method for preventing and/or treating pulmonary hypertension and/or emphysema in a subject in need of prevention and/or treatment, which method comprises administering an effective amount of Enzastaurin, wherein the effective amount of Enzastaurin is administered to a subject to reduce systemic blood pressure of said subject or the treatment reduces meanPAP pulmonary artery pressure (PAPm) below 20 mmHg, PVR below 3 WU, and/or PAWP (pulmonary artery wedge pressure) above 15 in said subject.

2. The method of claim 1, wherein the pulmonary hypertension belongs to WHO Group I, pulmonary arterial hypertension (PAH); WHO Group I', pulmonary veno-occlusive disease (PVOD) or pulmonary capillary hemangiornatosis (PCH); WHO Group I", persistent pulmonary hypertension of the newborn; WHO Group II, pulmonary hypertension secondary to left heart disease; WHO Group III, pulmonary hypertension due to lung disease or chronic hypoxia, WHO Group IV, chronic arterial obstruction; or WHO Group V, pulmonary hypertension with unclear or multifactorial mechanisms.

3. The method of claim 1, wherein the pulmonary hypertension or emphysema develops spontaneously in a subject, the pulmonary hypertension or emphysema develops based on the genetic background of a subject or the pulmonary hypertension or emphysema develops due to or in association with another disease or disorder, such as secondary to chronic obstructive pulmonary disease (COPD).

4. The method of claim 1, wherein the Enzastaurin up-regulates FHIT and/or bone morphogenetic protein receptor type-2 (BMPR2) in a subject.

5. The method of claim 1, wherein the Enzastaurin prevents and/or treats pulmonary hypertension and/or emphysema independent of PKC inhibition in a subject.

6. The method of claim 1, wherein the Enzastaurin prevents and/or treats pulmonary hypertension and/or emphysema by improving right ventricular systolic pressure (RVSP), RV hypertrophy, cardiac fibrosis and/or vascular remodeling in a subject.

7. The method of claim 1, wherein the Enzastaurin prevents and/or treats pulmonary hypertension and/or emphysema by preventing or reducing RVSP increase, RVH increase, vascular rarefaction, muscularization and/or neointima formation of distal vessels in a subject.

8. The method of claim 1, wherein the effective amount of Enzastaurin is administered to a subject having or suspected of having an end-stage PH.

9. The method of claim 1, wherein the subject having or suspected of having a low level of BMPR2 or having or suspected of having a BMPR2 mutation.

10. The method of claim 1, wherein the subject has or is suspected of having a low level of FHIT or having or suspected of having a FHIT mutation.

11. The method of claim 1, wherein the Enzastaurin is administered at a dosage ranging from about 5 mg/day to about 1,000 mg/day or the Enzastaurin is administered at a dosage to obtain an in vivo level ranging from about 20 nmol/L to about 6,000 nmol/L.

12. The method of claim 1, which further comprises administering an effective amount of a second prophylactic or therapeutic agent for preventing and/or treating pulmonary hypertension and/or emphysema in a subject, wherein the second prophylactic or therapeutic agent for preventing and/or treating pulmonary hypertension is a vasoactive substance, a prostaglandin, an endothelin receptor antagonist, a phosphodiesterase type 5 inhibitor or an activator of soluble guanylate cyclase, and the second prophylactic or therapeutic agent for preventing and/or treating emphysema is a bronchodilating medication, a steroid medication or an antibiotic.

13. The method of claim 1, wherein the subject is a human.

* * * * *